United States Patent
Lindqvist et al.

(10) Patent No.: US 12,357,689 B2
(45) Date of Patent: Jul. 15, 2025

(54) METHODS OF TREATING OR PREVENTING A CARDIOVASCULAR SYSTEM COMPLICATION OF SICKLE CELL DISEASE WITH AN ANTI-G-CSFR ANTIBODY

(71) Applicant: CSL Innovation Pty Ltd, Melbourne (AU)

(72) Inventors: Lisa Margareta Lindqvist, Melbourne (AU); Andreas Gille, King of Prussia, PA (US); Paolo Rossato, Marburg (DE); Markus Brechmann, Marburg (DE); John Davis Belcher, Minneapolis, MN (US); Gregory M. Vercellotti, Stillwater, MN (US)

(73) Assignee: CSL Innovation Pty Ltd, Melbourne (AU)

( * ) Notice: Subject to any disclaimer, the term of this patent is extended or adjusted under 35 U.S.C. 154(b) by 0 days.

(21) Appl. No.: 18/909,225

(22) Filed: Oct. 8, 2024

(65) Prior Publication Data
US 2025/0026822 A1 Jan. 23, 2025

Related U.S. Application Data

(63) Continuation of application No. PCT/AU2024/050734, filed on Jul. 5, 2024.

(60) Provisional application No. 63/635,186, filed on Apr. 17, 2024, provisional application No. 63/511,983, filed on Jul. 5, 2023.

(51) Int. Cl.
| | | |
|---|---|---|
| *A61K 39/395* | (2006.01) | |
| *A61P 7/06* | (2006.01) | |
| *A61P 9/10* | (2006.01) | |
| A61K 35/18 | (2015.01) | |
| C07K 14/535 | (2006.01) | |
| C07K 14/715 | (2006.01) | |
| C07K 16/28 | (2006.01) | |

(52) U.S. Cl.
CPC ............ *A61K 39/3955* (2013.01); *A61P 7/06* (2018.01); *A61P 9/10* (2018.01); A61K 35/18 (2013.01); C07K 14/535 (2013.01); C07K 14/7153 (2013.01); C07K 16/2866 (2013.01); C07K 2317/56 (2013.01); C07K 2317/565 (2013.01); C07K 2317/622 (2013.01); C07K 2317/626 (2013.01); C07K 2317/76 (2013.01)

(58) Field of Classification Search
CPC ............ A61K 39/3955; C07K 16/2866; C07K 14/7153; A61P 7/06; A61P 9/10
See application file for complete search history.

(56) References Cited

U.S. PATENT DOCUMENTS

| | | |
|---|---|---|
| 4,196,265 A | 4/1980 | Koprowski |
| 4,676,980 A | 6/1987 | Segal et al. |
| 4,816,567 A | 3/1989 | Cabilly et al. |
| 5,225,539 A | 7/1993 | Winter |
| 5,270,163 A | 12/1993 | Gold et al. |
| 5,422,248 A | 6/1995 | Smith et al. |
| 5,475,096 A | 12/1995 | Gold et al. |
| 5,530,101 A | 6/1996 | Queen et al. |
| 5,585,089 A | 12/1996 | Queen et al. |
| 5,589,456 A | 12/1996 | Smith et al. |
| 5,731,168 A | 3/1998 | Carter et al. |
| 5,807,715 A | 9/1998 | Morrison et al. |
| 5,885,793 A | 3/1999 | Griffiths et al. |
| 6,248,516 B1 | 6/2001 | Winter et al. |
| 6,300,064 B1 | 10/2001 | Knappik et al. |
| 7,083,784 B2 | 8/2006 | Dall'Acqua et al. |
| 7,108,852 B2 | 9/2006 | Devalaraja et al. |
| 7,250,297 B1 | 7/2007 | Beste et al. |
| 7,871,979 B2 | 1/2011 | Yorke-Smith et al. |
| 9,193,793 B2 | 11/2015 | Nash et al. |
| 9,382,538 B2 | 7/2016 | Collard et al. |
| 9,649,356 B2 | 5/2017 | Seelen |
| 2004/0132028 A1 | 7/2004 | Stumpp et al. |
| 2007/0059280 A1 | 3/2007 | Devalaraja et al. |
| 2007/0135620 A1 | 6/2007 | Chamberlain et al. |
| 2007/0224633 A1 | 9/2007 | Skerra et al. |
| 2008/0139791 A1 | 6/2008 | Lipovsek et al. |
| 2008/0199426 A1 | 8/2008 | Sukhatme et al. |
| 2009/0324591 A1 | 12/2009 | Crump et al. |
| 2010/0004167 A1 | 1/2010 | Yorke-Smith et al. |
| 2011/0110934 A1 | 5/2011 | Wicks et al. |

(Continued)

FOREIGN PATENT DOCUMENTS

| | | |
|---|---|---|
| CN | 107106681 A | 8/2017 |
| CN | 109310884 A | 2/2019 |

(Continued)

OTHER PUBLICATIONS

Benjamini et al, 1991. Immunology: A Short Course, 2nd edition, p. 40 only.*
Ferrara et al (2015. mAbs. 7(1): 32-41.*
Aggarwal, A. et al., "G-CSF and IL-8 but not GM-CSF correlate with severity of pulmonary neutrophilia in acute respiratory distress syndrome," Eur. Respir. J., vol. 15, pp. 895-901 (2000).

(Continued)

*Primary Examiner* — Zachary C Howard
(74) *Attorney, Agent, or Firm* — FINNEGAN, HENDERSON, FARABOW, GARRETT & DUNNER, LLP

(57) ABSTRACT

The present disclosure relates to methods for treating or preventing or delaying progression or reducing or inhibiting or hindering development of a complication associated with sickle cell disease in a subject suffering from sickle cell disease, the method comprising administering to the subject a compound that inhibits granulocyte colony stimulating factor (G-CSF) signaling and/or G-CSF activity.

13 Claims, 21 Drawing Sheets

Specification includes a Sequence Listing.

(56) References Cited

U.S. PATENT DOCUMENTS

| | | |
|---|---|---|
| 2012/0321630 A1 | 12/2012 | Nash et al. |
| 2013/0259824 A1 | 10/2013 | Wu et al. |

FOREIGN PATENT DOCUMENTS

| | | |
|---|---|---|
| EP | 0569141 A2 | 10/1993 |
| EP | 1167390 A1 | 2/2002 |
| EP | 1641818 B2 | 5/2006 |
| WO | 9404678 | 3/1994 |
| WO | 9407921 | 4/1994 |
| WO | 9521867 | 8/1995 |
| WO | 9749805 | 12/1997 |
| WO | 9844001 | 10/1998 |
| WO | 9932619 | 7/1999 |
| WO | 9945110 | 9/1999 |
| WO | 9949029 | 9/1999 |
| WO | 9953050 | 10/1999 |
| WO | 9957134 | 11/1999 |
| WO | 0034317 A2 | 6/2000 |
| WO | 0134815 A1 | 5/2001 |
| WO | 02080967 A1 | 10/2002 |
| WO | 02088171 A2 | 11/2002 |
| WO | 02098216 A1 | 12/2002 |
| WO | 2004064724 A2 | 8/2004 |
| WO | 2004108158 A1 | 12/2004 |
| WO | 2005056764 A2 | 6/2005 |
| WO | 2005118629 A1 | 12/2005 |
| WO | 2006033386 A1 | 3/2006 |
| WO | 2007025166 A2 | 3/2007 |
| WO | 2008003763 A1 | 1/2008 |
| WO | 2008017126 A1 | 2/2008 |
| WO | 2009039337 A2 | 3/2009 |
| WO | 2010080538 A1 | 7/2010 |
| WO | 2010085682 A2 | 7/2010 |
| WO | 2011032204 A1 | 3/2011 |
| WO | 2011051489 A2 | 5/2011 |
| WO | 2011103076 A1 | 8/2011 |
| WO | 2011107595 A1 | 9/2011 |
| WO | 2012017057 A1 | 2/2012 |
| WO | 2012112188 A1 | 8/2012 |
| WO | 2012171057 A1 | 12/2012 |
| WO | 2013075066 A2 | 5/2013 |
| WO | 2014072481 A1 | 5/2014 |
| WO | 2014179657 A1 | 11/2014 |
| WO | 2015063611 A2 | 5/2015 |
| WO | 2015127405 A2 | 8/2015 |
| WO | 2019104385 A1 | 6/2019 |
| WO | 2019124666 A2 | 6/2019 |
| WO | 2019178645 A1 | 9/2019 |
| WO | 2020248024 A1 | 12/2020 |

OTHER PUBLICATIONS

Akihama, Susumu et al., "Bone Marrow-Derived Cells Mobilized by Granulocyte-Colony Stimulating Factor Facilitate Vascular Regeneration in Mouse Kidney after Ischaemia/Reperfusion Injury," Tohoku J. Esp. Med., vol. 213, pp. 341-349 (2007).

Australian New Zealand Clinical Trials Registry (ANZCTR), Trial Review, "Dose escalation, placebo-controlled phase 1 study to assess the safety and tolerability of CSL324 in healthy adults." 6 pages (2016).

Ashchyan, Hovik J., Ba et al., "Pyoderma gangrenosum and other bowel- and arthritis-associated neutrophilic dermatoses," J Am Acad Dermatol, pp. 1009-1022 (2018).

Banuelos, Jesus et al., "Granulocyte colony-stimulating factor blockade enables dexamethasone to inhibit lipopolysaccharide-induced murine lung neutrophils," PLOS ONE, pp. 1-16 (2017).

Bendele, A.M., "Animal models of rheumatoid arthritis," J. Musculoskel Neuron Interact., vol. 1, No. 4, pp. 377-385 (2001).

Bidyasar, "Sweet Syndrome Associated With Granulocyte Colony-Stimulating Factor," Diagnosis in Oncology, American Society of Clinical Oncology, pp. 4355-4356 (2008).

Bostanci, Mehmet Suhha et al., "The protective effect of G-CSF on experimental ischemia/reperfusion injury in rat ovary," Arch. Gynecol. Obstet., vol. 293; pp. 789-795 (2016).

Bozinovski, Steven et al., "Granulocyte/Macrophase-Colony-stimulating Factor (GM-CSF) Regulates Lung Innate Immunity to Lipopolysaccharide through Akt/Erk Activation of NFkB AP-1 in Vivo*," The Journal of Biological Chemistry, vol. 277, No. 45, pp. 42808-42814 (2002).

Butler, Daniel BS et al., "What Do Autoinflammatory Syndromes Teach About Common Cutaneous Diseases Such as Pyoderma Gangrenosum? A Commentary," Dermatol. Clin., vol. 31, pp. 427-435 (2013).

Campbell, Ian K. et al., "Therapeutic Targeting of the G-CSF Receptor Reduces Neutrophil Trafficking and Joint Inflammation in Antibody-Mediated Inflammatory Arthritis," J Immunol, pp. 1-15 (2016).

Cugno, Massimo et al., "Inflammatory Joint Disorders and Neutrophilic Dermatoses: a Comprehensive Review," Clinic. Rev. Allerg. Immunol., vol. 54, pp. 269-281 (2018).

DeBruin, Cortney et al., "Most purported antibodies to the human granulocyte colony-stimulating factor receptor are not specific," Experimental Hematology, vol. 38, pp. 1022-1035 (2010).

Perez De La Lastra, J.M. et al., "Epitope mapping of 10 monoclonal antibodies against the plg analogue of human membrane cofactor protein (MCP)," Immunology, vol. 96, pp. 663-670 (1999).

De Bries, Bart et al., "Complement Factor C5a Mediates Renal Ischemia-Reperfusion Injury Independent from Neutrophils," J Immunol, pp. 3883-3889 (2003).

Dondelinger, Mathieu et al., "Understanding the Significance and Implications of Antibody Numbering and Antigen-Binding Surface/Residue Definition," Frontiers in Immunology, vol. 9, pp. 1-15 (2018).

Draper, Bradley, et al., "Bullous Sweet's syndrome in congenital neutropenia: Association with pegfilgrastim," J. Am. Acad. Dermatol., vol. 52, No. 5, pp. 901-905 (2005).

Elsasser, Annika et al., "The fusion protein AML1-ETO in acute myeloid leukemia with translocation t(8;21) induces c-jun protein expression via the proximal AP-1 site of the c-jun promoter in an indirect, JNK-dependent manner," Oncogene, vol. 22, pp. 5646-5657 (2003).

Fujii, Asami et al., "Sweet's Syndrome Successfully Treated with Granulocyte and Monocyte Adsorption Apheresis," Case Rep Dermatol, vol. 9, pp. 13-18 (2017).

Fukunaga, Rikiro et al., "Three different mRNAs encoding human granulocyte colony-stimulating factor receptor," Proc. Natl. Acad. Sci. USA, vol. 87, pp. 8702-8706 (1990).

Goldberg, Gabrielle L. et al., "G-CSF and Neutrophils are Nonredundant Mediators of Murine Experimental Autoimmune Uveoretinitis," The American Journal of Pathology, vol. 186, No. 1, pp. 172-184 (2016).

Guo, Yan-Rong et al., "The origin, transmission and clinical therapies on coronavirus disease 2019 (COVID-19) outbreak—an update on the status," Military medical Research, vol. 7, No. 11, pp. 1-10 (2020).

Higuchi, Takuya MD et al., "Granulocyte Colony-Stimulating Factor Prevents Reperfusion Injury After Heart Preservation," Ann Thorac Surg, 85:1367-1373 (2008).

Huang, Chaolin et al., "Clinical features of patients infected with 2019 novel coronavirus in Wuhan," The Lancet, vol. 395, pp. 497-506 (2020).

Jiang, Hui-Min et al., "Role for Granulocyte Colony Stimulating Factor in Angiotensin II-Induced Neutrophil Recruitment and Cardiac Fibrosis in Mice," American Journal of Hypertension, vol. 26, No. 10, pp. 1224-1233 (2013).

Kang, Jichao et al., "Rapid Formulation Development for Monoclonal Antibodies," Biopharmaceutical Fill and Finish. 6 pages (2016).

Kawakami, Tamihiro et al., "Elevated Serum Granulocyte Colony-Stimulating Factor Levels in Patients With Active Phase of Sweet Syndrome and Patients With Active Behcet Disease," Arch. Dermatol., vol. 140, pp. 570-574 (2004).

(56) References Cited

OTHER PUBLICATIONS

Ko, Bong-Kook et al., "Affinity Maturation of Monoclonal Antibody 1E11 by Targeted Randomization in CDR3 Regions Optimizes Therapeutic Antibody Targeting of HER2-Positive Gastric Cancer," PLOS ONE, pp. 1-16 (2015).
Lama, Vibha N. et al., "Models of Lung Transplant Research: a consensus statement from the National Heart, Lung, and Blood Institute workshop," JCI Insight, pp. 1-15 (2017).
Layton, Judith E., et al., "Neutralising Antibodies to the Granulocyte Colony-stimulating Factor Receptor Recognise both the Immunoglobulin-like Domain and the Cytokine Receptor Homologous Domain," Growth Factors, vol. 14, pp. 117-130 (1997).
Layton, Judith, et al., "Interaction of Granulocyte Colony-stimulating Factor (G-CSF) with Its Receptor," J Biol Chem, vol. 274, No. 25, pp. 17445-17451 (1999).
Layton, Judith E., et al., "Identification of Ligand-binding Site III on the Immunoglobulin-like Domain of the Granulocyte Colony-stimulating Factor Receptor*," J Biol Chem, vol. 276, No. 39, pp. 36779-36787 (2001).
Layton, Juidth E., et al., "The interaction of G-CSF with its receptor," Frontiers in Bioscience, vol. 11, pp. 3181-3189 (2006).
Layton, Judity E., et al., "Identification of a Ligand-binding Site on the Granulocyte Colony-stimulating Factor Receptor by Molecular Modeling and Mutagenesis*," J Biol Chem, vol. 272, No. 49, pp. 29735-29741 (1997).
Lescure, Francois-Xavier et al., "Clinical and virological data of the first cases of COVID-19 in Europe: a case series," Lancet Infect Dis, 20:1-10 (2020).
Li, Yiwen et al., "Pretreatment with granulocyte colony-stimulating factor attenuated renal ischaemia and reperfusion injury via activation of PI3/Akt signal pathway," Nephrology, vol. 13, pp. 508-516 (2008).
Li, Yili et al., "X-ray snapshots of the maturation of an antibody response to a protein antigen," Nature Structural Biology, vol. 10, No. 6, pp. 482-488 (2003).
Liao, Juan et al., "Progress on role of cytokine storm in exacerbation of coronavirus disease," Abstract, one page (2019).
Lloyd, C. et al., "Modelling the human immune responses performance of a 10^11 human antibody repertoire against a broad panel of therapeutically relevant antigens," Protein Engineering, Design & Selection, vol. 22, No. 3, pp. 159-168 (2009).
Lu, Chuan-Zhen et al., "Neuroprotection of G-CSF in cerebral ischemia," Frontiers in Bioscience, vol. 12, pp. 2869-2875 (2007).
Navarini, Alexander A. et al., "Neutrophilic dermatoses and autoinflammatory diseases with skin involvement-innate immune disorders," Semin Immunopathol, vol. 38, pp. 45-56 (2016).
Nelson, Caroline A. et al., "Pathogenesis, Sweet syndrome, neutrophilic eccrine hidradenitis, and Behcet disease," J. Am. Acad. Dermatol., pp. 987-1006 (2018).
Nishida, Masashi et al., "How Does G-CSF Act on the Kidney during Acute Tubular Injury?," Nephron Exp. Nephrol., vol. 104, pp. e123-e128 (2006).
Nogueira, Breno Valentim, et al., "Granulocyte Colony Stimulating Factor Prevents Kidney Infarction and Attenuates Renovascular Hypertension," Cell Physiol Biochem, vol. 29, pp. 143-152 (2012).
Prendiville, Julie, et al., "Neutrophilic Dermatoses in Two Children with Idiopathic Neutropenia: Association with Granulocyte Colony-Stimulating Factor (G-CSF) Therapy," Pediatric Dermatology, vol. 18, No. 5, pp. 417-421 (2001).
Qin, Chuan, et al. "Dysregulation of immune response in patients with COVID-19 in Wuhan, China," Clinical Infectious Diseases, vol. 71, Iss. 15, pp. 1-24 (2020).
Queto, Tulio et al., "G-CSF suppresses allergic pulmonary inflammation, downmodulating cytokine, chemokine and eosinophil production," Life Sciences, vol. 88, pp. 830-838 (2011).
Rajpal, Arvind et al., "A general method for greatly improving the affinity of antibodies by using combinatorial libraries," PNAS, vol. 102, No. 24, pp. 8466-8471 (2005).
Salvadori, Maurizio et al., "Update on ischemia-reperfusion injury in kidney transplantation: Pathogenesis and treatment," World J Transplant, vol. 5, Issue 2, pp. 52-67 (2015).
Belcher, John D. et al., "Anti-G-CSFR Monoclonal Antibodies to Treat Sickle Cell Disease," Experts@Minnesota, https://experts.umn.edu/en/projects/anti-g-csfr-monoclonal-antibodies-to-treat-sickle-cell-disease.
Scalzo-Inguanti, Karen et al., "A neutralizing anti-G-CSFR antibody blocks G-CSF-induced neutrophilia without inducing neutropenia in nonhuman primates," Journal of Leukocyte Biology, vol. 102, pp. 537-549 (2017).
Scozzi, D., et al., "The Role of Neutrophils in Transplanted Organs," American Journal of Transplantation, vol. 17, pp. 328-335 (2017).
Shima, Chieko et al., "Neuroprotective Effects of Granulocyte Colony-Stimulating Factor on Ischemia-Reperfusion Injury of the Retina," Ophthalmic Res, vol. 48, pp. 199-207 (2012).
Steinberg, Kenneth P., et al., "Evolution of Bronchoalveolar Cell Populations in the Adult Respiratory Distress Syndrome," Am J Respir Crit Care Med, vol. 150, pp. 113-122 (1994).
Uchiyama, Susumu, "Liquid formulation for antbody drugs," Biochimica et Biophysica Acta., vol. 1844, pp. 2041-2052 (2014).
Tian, Sufang, et al., "Pulmonary Pathology of Early-Phase 2019 Novel Coronavirus (COVID-19) Pneumonia in Two Patients With Lung Cancer," Journal of Thoracic Oncology, pp. 1-5 (2020).
Toussaint, Marie et al., "Host DNA released by NETosis promotes rhinovirus-induced type-2 allergic asthma exacerbation," Nature Medicine, vol. 23, No. 6, pp. 681-694 (2017).
Ueda, Kazutaka et al., "Granulocyte Colony Stimulating Factor Directly Inhibits Myocardial Ischemia-Reperfusion Injury Through Akt-Endothelial NO Synthase Pathway," Asterioscler. Thromb. Vase Biol., pp e108-e113 (2006).
Uhara, Hisashi, et al., "Neutrophilic dermatoses with acute myeloid leukemia associated with an increase of serum colony-stimulating factor," J. Am. Acad. Dermatol., vol. 59, No. 2, pp. S10-S12 (2008).
Viola, Margarida et al., "Subcutaneous delivery of monoclonal antibodies: How do we get there?," Journal of Controlled Release, vol. 286, pp. 301-314 (2018).
Wang, H., et al., "Anti G-CSFR Antibody Treatment Suppresses Neutrophilic and Type-2 Lung Inflammation in an Allergic Asthma Model Worsened by Neonatal Coinfection," TSANZ Oral Presentations, p. 26 (2018).
Wang, Hao et al., "G-CSFR antagonism reduces neutrophilic inflammation during pneumococcal and influenza respiratory infections without compromising clearance," Scientific Reports, vol. 9, pp. 1-12 (2019).
Whitaker, Neal et al., "A Formulation Development Approach to Identify and Select Stable Ultra-High-Concentration Monoclonal Antibody Formulations With Reduced Viscosities," Journal of Pharmaceutical Sciences, vol. 106, pp. 3230-3241 (2017).
Yan, Ji-Jing et al., "Granulocyte Colony-Stimulating Factor Attenuates Renal Ischemia-Reperfusion Injury by Inducing Myeloid-Derived Suppressor Cells," JASN, vol. 31, pp. 731-746 (2020).
Yao, Xianglan, "The A's Have It: Developing Apolipoprotein A-I Mimetic Peptides Into a Novel Treatment for Asthma," Chest, pp. 283-288 (2016).
Zhang, Ying et al., "Ischemia-reperfusion induces G-CSF gene expression by renal medullary thick ascending limb cells in vivo and in vitro," Am. J. Physiol. Renal Physiol., vol. 286, pp. F1193-F1201 (2004).

* cited by examiner

B

C

I

J

A

B

G

H  I

A

B

Vehicle, VR81 or IgG control was admininstered 40 minutes after mG-CSF

SEQUENCE LISTING

```
Sequence total quantity: 28
SEQ ID NO: 1          moltype = AA  length = 319
FEATURE               Location/Qualifiers
source                1..319
                      mol_type = protein
                      organism = synthetic construct
SEQUENCE: 1
ECGHISVSAP IVHLGDPITA SCIIKQNCSH LDPEPQILWR LGAELQPGGR QQRLSDGTQE    60
SIITLPHLNH TQAFLSCALN WGNSLQILDQ VELRAGYPPA IPHNLSCLMN LTTSSLICQW   120
EPGPETHLPT SFTLKSFKSR GNCQTQGDSI LDCVPKDGQS HCSIPRKHLL LYQNMGIWVQ   180
AENALGTSMS PQLCLDPMDV VKLEPPMLRT MDPSPEAAPP QAGCLQLSWE PWQPGLHINQ   240
KCELRHKPQR GEASWALVGP LPLEALQYEL CGLLPATAYT LQIRCIRWPL PGHWSDWSPS   300
LELRTTERAP THHHHHHHH                                                319

SEQ ID NO: 2          moltype = AA  length = 118
FEATURE               Location/Qualifiers
source                1..118
                      mol_type = protein
                      organism = synthetic construct
SEQUENCE: 2
EVQLLESGGG LVQPGGSLRL SCAASGFTFS LYWMGWVRQA PGKGLEWVSS ISSSGGVTPY    60
ADSVKGRFTI SRDNSKNTLY LQMNSLRAED TAVYYCAMLG ELGWFDPWGQ GTLVTVSS    118

SEQ ID NO: 3          moltype = AA  length = 107
FEATURE               Location/Qualifiers
source                1..107
                      mol_type = protein
                      organism = synthetic construct
SEQUENCE: 3
DIQMTQSPSA LSASVGDRVT ITCRASQGIS SYLNWYQQKP GKAPKLLIYY ASNLQNGIPS    60
```

```
RFSGSGSGTD FTLTISSLQP EDFATYHCQQ SYSTPLTFGG GTNVEIR                  107

SEQ ID NO: 4              moltype = AA   length = 118
FEATURE                   Location/Qualifiers
source                    1..118
                          mol_type = protein
                          organism = synthetic construct
SEQUENCE: 4
EVQLLESGGG LVQPGGSLRL SCAASGFTFS LYWMGWVRQA PGKGLEWVSS ISSSGGVTPY    60
ADSVKGRFTI SRDNSKNTLY LQMNSLRAED TAVYYCAKLG ELGWFDPWGQ GTLVTVSS     118

SEQ ID NO: 5              moltype = AA   length = 107
FEATURE                   Location/Qualifiers
source                    1..107
                          mol_type = protein
                          organism = synthetic construct
SEQUENCE: 5
DIQMTQSPSS LSASVGDRVT ITCRASQGIS SYLNWYQQKP GKAPKLLIYY ASNLQNGVPS    60
RFSGSGSGTD FTLTISSLQP EDFATYYCQQ SYSTPLTFGG GTKVEIK                 107

SEQ ID NO: 6              moltype = AA   length = 5
FEATURE                   Location/Qualifiers
source                    1..5
                          mol_type = protein
                          organism = synthetic construct
SEQUENCE: 6
LYWMG                                                                 5

SEQ ID NO: 7              moltype = AA   length = 17
FEATURE                   Location/Qualifiers
source                    1..17
                          mol_type = protein
                          organism = synthetic construct
SEQUENCE: 7
SISSSGGVTP YADSVKG                                                   17

SEQ ID NO: 8              moltype = AA   length = 9
FEATURE                   Location/Qualifiers
source                    1..9
                          mol_type = protein
                          organism = synthetic construct
SEQUENCE: 8
LGELGWFDP                                                             9

SEQ ID NO: 9              moltype = AA   length = 11
FEATURE                   Location/Qualifiers
source                    1..11
                          mol_type = protein
                          organism = synthetic construct
SEQUENCE: 9
RASQGISSYL N                                                         11

SEQ ID NO: 10             moltype = AA   length = 6
FEATURE                   Location/Qualifiers
source                    1..6
                          mol_type = protein
                          organism = synthetic construct
SEQUENCE: 10
ASNLQN                                                                6

SEQ ID NO: 11             moltype = AA   length = 9
FEATURE                   Location/Qualifiers
source                    1..9
                          mol_type = protein
                          organism = synthetic construct
SEQUENCE: 11
QQSYSTPLT                                                             9

SEQ ID NO: 12             moltype = AA   length = 8
FEATURE                   Location/Qualifiers
VARIANT                   5
                          note = X is an amino acid selected from the group
                            consisting of tryptophan, glutamine, methionine, serine,
                            phenylalanine, glutamic acid and histidine
VARIANT                   6
                          note = X iis an amino acid selected from the group
                            consisting of phenylalanine, tyrosine, methionine, serine,
                            glycine and isoleucine
VARIANT                   7
```

```
                            note = X is an amino acid selected from the group
                             consisting of aspartic acid, methionine, glutamine,
                             serine, leucine, valine, arginine and histidine
VARIANT                 8
                            note = X is an amino acid selected from the group
                             consisting of proline gltuamic acid, alanine, leucine,
                             phenylalanine, tyronis, threonine, asparagine, aspartic
                             acid, serine , glycine, arginine, lysine
source                  1..8
                            mol_type = protein
                            organism = synthetic construct
SEQUENCE: 12
LGELXXXX                                                                         8

SEQ ID NO: 13           moltype =    length =
SEQUENCE: 13
000

SEQ ID NO: 14           moltype = AA   length = 445
FEATURE                 Location/Qualifiers
source                  1..445
                            mol_type = protein
                            organism = synthetic construct
SEQUENCE: 14
EVQLLESGGG LVQPGGSLRL SCAASGFTFS LYWMGWVRQA PGKGLEWVSS ISSSGGVTPY    60
ADSVKGRFTI SRDNSKNTLY LQMNSLRAED TAVYYCAKLG ELGWFDPWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGK                                        445

SEQ ID NO: 15           moltype = AA   length = 214
FEATURE                 Location/Qualifiers
source                  1..214
                            mol_type = protein
                            organism = synthetic construct
SEQUENCE: 15
DIQMTQSPSS LSASVGDRVT ITCRASQGIS SYLNWYQQKP GKAPKLLIYY ASNLQNGVPS    60
RFSGSGSGTD FTLTISSLQP EDFATYYCQQ SYSTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 16           moltype = AA   length = 836
FEATURE                 Location/Qualifiers
source                  1..836
                            mol_type = protein
                            organism = Homo sapiens
SEQUENCE: 16
MARLGNCSLT WAALIILLLP GSLEECGHIS VSAPIVHLGD PITASCIIKQ NCSHLDPEPQ    60
ILWRLGAELQ PGGRQQRLSD GTQESIITLP HLNHTQAFLS CCLNWGNSLQ ILDQVELRAG   120
YPPAIPHNLS CLMNLTTSSL ICQWEPGPET HLPTSFTLKS FKSRGNCQTQ GDSILDCVPK   180
DGQSHCCIPR KHLLLYQNMG IWVQAENALG TSMSPQLCLD PMDVVKLEPP MLRTMDPSPE   240
AAPPQAGCLQ LCWEPWQPGL HINQKCELRH KPQRGEASWA LVGPLPLEAL QYELCGLLPA   300
TAYTLQIRCI RWPLPGHWSD WSPSLELRTT ERAPTVRLDT WWRQRQLDPR TVQLFWKPVP   360
LEEDSGRIQG YVVSWRPSGQ AGAILPLCNT TELSCTFHLP SEAQEVALVA YNSAGTSRPT   420
PVVFSESRGP ALTRLHAMAR DPHSLWVGWE PPNPWPQGYV IEWGLGPPSA SNSNKTWRME   480
QNGRATGFLL KENIRPFQLY EIIVTPLYQD TMGPSQHVYA YSQEMAPSHA PELHLKHIGK   540
TWAQLEWVPE PPELGKSPLT HYTIFWTNAQ NQSFSAILNA SSRGFVLHGL EPASLYHIHL   600
MAASQAGATN STVLTLMTLT PEGSELHIIL GLFGLLLLLT CLCGTAWLCC SPNRKNPLWP   660
SVPDPAHSSL GSWVPTIMEE DAFQLPGLGT PPITKLTVLE EDEKKPVPWE SHNSSETCGL   720
PTLVQTYVLQ GDPRAVSTQP QSQSGTSDQV LYGQLLGSPT SPGPGHYLRC DSTQPLLAGL   780
TPSPKSYENL WFQASPLGTL VTPAPSQEDD CVFGPLLNFP LLQGIRVHGM EALGSF       836

SEQ ID NO: 17           moltype = AA   length = 319
FEATURE                 Location/Qualifiers
source                  1..319
                            mol_type = protein
                            organism = synthetic construct
SEQUENCE: 17
ECGHISVSAP IVHLGDPITA SCIIKQNCSH LDLEPQILWR LGAELQPGGR QQRLSDGSQQ    60
STITLPHLNH TRAFLSCALN WGNSLQILDQ VELRAGYPPA VPRNLSCLMN LTTSSLICQW   120
EPGPETHLPT SFTLKSFKSR GNCQTQGDSI MDCVPEDGQS HCSIPRRHLL LYQNMGIWVQ   180
AENALGTSMS PQLCLEPMDV VKLEPPMLRT MDPSPEAAPP QAGCLQLSWE PWQPALHINQ   240
KCELRHKPQS GEASWALVGP LPLEALRYEL CGLLPATAYT LQIRCIRWPL PGHWSNWSPS   300
LELRTTERAP THHHHHHHH                                                319

SEQ ID NO: 18           moltype = AA   length = 444
```

```
FEATURE                 Location/Qualifiers
source                  1..444
                        mol_type = protein
                        organism = synthetic construct
SEQUENCE: 18
EVQLLESGGG  LVQPGGSLRL  SCAASGFTFS  LYWMGWVRQA  PGKGLEWVSS  ISSSGGVTPY   60
ADSVKGRFTI  SRDNSKNTLY  LQMNSLRAED  TAVYYCAKLG  ELGWFDPWGQ  GTLVTVSSAS  120
TKGPSVFPLA  PCSRSTSEST  AALGCLVKDY  FPEPVTVSWN  SGALTSGVHT  FPAVLQSSGL  180
YSLSSVVTVP  SSSLGTKTYT  CNVDHKPSNT  KVDKRVESKY  GPPCPPCPAP  EFLGGPSVFL  240
FPPKPKDTLM  ISRTPEVTCV  VVDVSQEDPE  VQFNWYVDGV  EVHNAKTKPR  EEQFNSTYRV  300
VSVLTVLHQD  WLNGKEYKCK  VSNKGLPSSI  EKTISKAKGQ  PREPQVYTLP  PSQEEMTKNQ  360
VSLTCLVKGF  YPSDIAVEWE  SNGQPENNYK  TTPPVLDSDG  SFFLYSRLTV  DKSRWQEGNV  420
FSCSVMHEAL  HNHYTQKSLS  LSLG                                            444

SEQ ID NO: 19           moltype = DNA  length = 1335
FEATURE                 Location/Qualifiers
source                  1..1335
                        mol_type = other DNA
                        organism = synthetic construct
SEQUENCE: 19
gaggtgcagc tgctggaatc tggcggaggg ctggtgcagc aggcggcag cctgaggctg     60
tcctgcgccg ccagcggctt cacccttcag ctgtactgga tgggctgggt ccggcaggct    120
ccaggcaagg gcctggaatg ggtgtccagc atcagcagca gcggcggagt gacccctac    180
gccgacagcg tgaagggcag gttcaccatc agcagggaca acagcaagaa caccctgtac   240
ctgcagatga acagcctgag ggccgaggac accgccgtgt actactgcgc caagctgggc   300
gagctggggct ggttcgaccc ctggggccag ggcaccctgg tgaccgtgag cagcgccgag   360
accaagggcc caagcgtgtt ccccctggcc cctgctcca gaagcaccag cgagagcaca   420
gccgccctgg gctgcctggt gaaggactac ttccccgagc ccgtgaccgt gtcctggaac   480
agcggagccc tgaccagcgg cgtgcacacc ttccccgccg tgctgcagag cagcggcctg   540
tacagcctga gcagcgtgtg gaccgtgccc agcagcagc tgggcaccaa gacctacacc   600
tgtaacgtgg accacaagcc cagcaacacc aaggtggaca gagggtgga gagcaagtac   660
ggcccaccct gccccccctg cccagccccc gagttcctgg gcggaccag cgtgttcctg   720
ttcccccca agcccaagga caccctgatg atcagcagaa cccccgaggt gacctgtgtg   780
gtggtggacg tgtcccagga ggaccccgag gtccagttca actggtacgt ggacggcgtg   840
gaggtgcaca acgccaagac caagcccaga gaggagcagt ttaacagcac ctaccgggtg   900
gtgtccgtgc tgaccgtgct gcaccaggac tggctgaacg gcaaagagta caagtgtaag   960
gtctccaaca agggcctgcc aagcagcatc gaaaagacca tcagcaaggc caagggccag  1020
cctagagagc cccaggtcta caccctgcca ccagccaag aggagatgac caagaaccag  1080
gtgtccctga cctgtctggt gaagggcttc tacccaagcg acatcgccgt ggagtgggag  1140
agcaacggcc agcccgagaa caactacaag accacccccc cagtgctgga cagcgacggc  1200
agcttcttcc tgtacagcag gctgaccgtg gacaagtcca gatggcagga gggcaacgtc  1260
tttagctgct ccgtgatgca cgaggccctg cacaaccact acacccagaa gagcctgagc  1320
ctgtccctgg gcaag                                                    1335

SEQ ID NO: 20           moltype = DNA  length = 642
FEATURE                 Location/Qualifiers
source                  1..642
                        mol_type = other DNA
                        organism = Synthetic construct
SEQUENCE: 20
gacatccaga tgacccagag ccccagcagc ctgagcgcca gcgtgggcga cagggtgacc    60
atcacctgca gggccagcca gggcatcagc agctacctga actggtatca gcagaagccc   120
ggcaaggccc ccaagctgct gatctactac gccagcaacc tgcagaacgg cgtgcccagc   180
aggttcagcg gcagcggctc cggcaccgac ttcaccctga ccatcagcag cctgcagccc   240
gaggacttcg ccacctacta ctgccagcag agctacagca cccccctgac cttcggcgga   300
gggaccaagg tggagatcaa gcgtacggtg gccgctccca gcgtgttcat cttcccccca   360
agcgacgagc agctgaagag cggcaccgcc agcgtggtgt gtctgctgaa caacttctac   420
cccagggagg ccaaggtgca gtggaaggtg gacaacgccc tgcagagcgg caacagccag   480
gagagcgtca ccgagcagga cagcaaggac tccacctaca gcctgagcag cacccctgacc   540
ctgagcaagg ccgactacga aagcacaag gtgtacgcct gtgaggtgac ccaccaggg c   600
ctgtccagcc ccgtgaccaa gagcttcaac aggggcgagt gc                      642

SEQ ID NO: 21           moltype = DNA  length = 354
FEATURE                 Location/Qualifiers
source                  1..354
                        mol_type = other DNA
                        organism = synthetic construct
SEQUENCE: 21
gaggtgcagc tgctggaatc tggcggaggg ctggtgcagc aggcggcag cctgaggctg     60
tcctgcgccg ccagcggctt cacccttcag ctgtactgga tgggctgggt ccggcaggct   120
ccaggcaagg gcctggaatg ggtgtccagc atcagcagca gcggcggagt gacccctac   180
gccgacagcg tgaagggcag gttcaccatc agcagggaca acagcaagaa caccctgtac  240
ctgcagatga acagcctgag ggccgaggac accgccgtgt actactgcgc caagctgggc  300
gagctggggct ggttcgaccc ctggggccag ggcaccctgg tgaccgtgag cagc        354

SEQ ID NO: 22           moltype = DNA  length = 321
FEATURE                 Location/Qualifiers
source                  1..321
                        mol_type = other DNA
```

```
                                      organism = Synthetic construct
SEQUENCE: 22
gacatccaga tgacccagag ccccagcagc ctgagcgcca gcgtgggcga cagggtgacc        60
atcacctgca gggccagcca gggcatcagc agctacctga actggtatca gcagaagccc       120
ggcaaggccc ccaagctgct gatctactac gccagcaacc tgcagaacgg cgtgcccagc       180
aggttcagcg gcagcggctc cggcaccgac ttcaccctga ccatcagcag cctgcagccc       240
gaggacttcg ccacctacta ctgccagcag agctacagca cccccctgac cttcggcgga       300
gggaccaagg tggagatcaa g                                                 321

SEQ ID NO: 23           moltype = DNA  length = 15
FEATURE                 Location/Qualifiers
source                  1..15
                        mol_type = other DNA
                        organism = synthetic construct
SEQUENCE: 23
ctgtactgga tgggc                                                         15

SEQ ID NO: 24           moltype = DNA  length = 51
FEATURE                 Location/Qualifiers
source                  1..51
                        mol_type = other DNA
                        organism = synthetic construct
SEQUENCE: 24
agcatcagca gcagcggcgg agtgaccccc tacgccgaca gcgtgaaggg c                 51

SEQ ID NO: 25           moltype = DNA  length = 27
FEATURE                 Location/Qualifiers
source                  1..27
                        mol_type = other DNA
                        organism = synthetic construct
SEQUENCE: 25
ctgggcgagc tgggctggtt cgacccc                                            27

SEQ ID NO: 26           moltype = DNA  length = 33
FEATURE                 Location/Qualifiers
source                  1..33
                        mol_type = other DNA
                        organism = synthetic construct
SEQUENCE: 26
agggccagcc agggcatcag cagctacctg aac                                     33

SEQ ID NO: 27           moltype = DNA  length = 18
FEATURE                 Location/Qualifiers
source                  1..18
                        mol_type = other DNA
                        organism = synthetic construct
SEQUENCE: 27
gccagcaacc tgcagaac                                                      18

SEQ ID NO: 28           moltype = DNA  length = 27
FEATURE                 Location/Qualifiers
source                  1..27
                        mol_type = other DNA
                        organism = synthetic construct
SEQUENCE: 28
cagcagagct acagcacccc cctgacc                                            27
```

METHODS OF TREATING OR PREVENTING A CARDIOVASCULAR SYSTEM COMPLICATION OF SICKLE CELL DISEASE WITH AN ANTI-G-CSFR ANTIBODY

RELATED APPLICATION DATA

This application is a continuation of International Application No. PCT/AU2024/050734, filed 5 Jul. 2024, which claims priority from U.S. Patent Application No. 63/511,983 filed on 5 Jul. 2023 and entitled "Methods of treating or preventing a complication of sickle cell disease", and U.S. Patent Application No. 63/635,186 filed on 17 Apr. 2024 and entitled "Methods of treating or preventing a complication of sickle cell disease". The entire contents of these applications are hereby incorporated by reference.

SEQUENCE LISTING

The present application is filed together with a Sequence Listing in electronic XML format. The Sequence Listing is named 539919PCT Sequence Listing.xml, was created Jul. 5, 2024, and is 32,236 bytes in size. The entire contents of the Sequence Listing are hereby incorporated by reference.

FIELD

The present disclosure relates to methods for treating or preventing or delaying progression or reducing or inhibiting or hindering development of a complication associated with sickle cell disease in a subject suffering from sickle cell disease, the method comprising administering to the subject a compound that inhibits granulocyte colony stimulating factor (G-CSF) signaling and/or G-CSF activity.

BACKGROUND

Sickle cell disease (SCD) has a high prevalence and social impact worldwide. With about 300,000 babies born with SCD globally every year, SCD also has a high mortality within the first three years of birth.

SCD refers to a group of inherited erythrocyte disorders caused by a mutation in both of an individual's beta globin genes. Beta globin combines with alpha globin to form hemoglobin, required for blood oxygen transport. In SCD, beta globin mutations cause abnormal hemoglobin which polymerises to form hard, sticky red blood cells that are C- or sickle-shaped. The specific beta globin mutations inherited by an individual contribute to the severity of disease experienced. The most severe common SCD is sickle cell anaemia, caused by a homozygous glutamic acid-valine mutation in the sixth amino acid of the beta globin protein causing a mutant beta globin protein, HbS. Hemoglobin SC disease and HbS beta thalassemia are caused by compound heterozygous mutations of HbS together with either mutant beta globin HbC or a beta thalassemia gene respectively and are usually milder than sickle cell anaemia. Beta thalassemia has two forms, zero and plus; HbS beta0 usually results in severe SCD disease, while HbS beta+ usually results in milder SCD disease. Other, rare forms of SCD exist, with variable severity, wherein an HbS gene is inherited together with a different hemoglobin mutation, for example HbD, HbE or HbO.

Sickle cells are prone to hemolysis earlier than normal erythrocytes, resulting in a chronic depletion of red blood cells. Sickle cells are sometimes referred to as being "sticky" as they can also clog smaller blood vessels due to their rigidity and tendency to aggregate. In addition to shortened life expectancy, subjects with SCD suffer increased morbidity due to varied chronic and acute complications, including: acute chest syndrome, anaemia, aplastic crisis, avascular necrosis, blood clots, dactylitis, fever, hepatic crisis, hyperhemolytic crisis, infection, kidney disease, leg ulcers, liver disease, organ damage, pain crises, priapism, pulmonary hypertension, sleep-disordered breathing, splenic sequestration, stroke, proliferative retinopathy and vaso-occlusive crisis.

Currently, there are five major approaches for the general management of SCD and its complications. These include (i) symptomatic management, (ii) supportive management, (iii) preventive management, (iv) abortive management, and (v) curative therapy. A blood and bone marrow transplant is the only cure for SCD, is only effective for some types of SCD and is only available where a closely matched donor can be found. In addition, in certain patients it carries a significant risk of complications, including death. Treatments to alleviate complications arising from SCD include pharmaceuticals that: prevent the C-shaped deformation of erythrocytes, reduce vaso-occlusion and pain crises, reduce or prevent multiple or complex complications, treat pain, and reduce the risk of infection; and/or transfusions. Currently approved therapies include hydroxyurea, Endari® (L-glutamine), Adakveo® (crizanlizumab-tmca) and Oxbryta® (voxelotor). The currently available treatments each have a number of side-effects, availability restrictions and/or limited efficacy for different patient groups.

Accordingly, there remains a significant need for improved therapies for treating or reducing the severity or the development of complications associated with SCD.

SUMMARY

In producing the present invention, the inventors identified granulocyte colony stimulating factor (G-CSF) as a potential target for pharmacological intervention of complications associated with sickle cell disease. The inventors found that administering a compound that inhibits G-CSF binding to its receptor and/or inhibits G-CSF signaling successfully inhibited several measures of vaso-occlusion and vascular stasis in a mouse model of sickle cell disease (i.e., Townes mouse).

These findings by the inventors provide the basis for methods for treating or preventing or delaying progression or reducing or inhibiting or hindering development of a complication associated with sickle cell disease by inhibiting G-CSF binding to its receptor and/or inhibiting G-CSF signaling.

These findings by the inventors provide the basis for methods for treating or preventing or delaying progression or reducing or inhibiting or hindering development of a complication associated with sickle cell disease by inhibiting G-CSF signaling.

These findings by the inventors also provide the basis for methods for treating or preventing or delaying progression or reducing or inhibiting or hindering development of a complication associated with sickle cell disease by inhibiting G-CSF binding to its receptor.

These findings by the inventors additionally provide the basis for methods for treating or preventing or delaying progression or reducing or inhibiting or hindering development of a complication associated with sickle cell disease by inhibiting G-CSF receptor mediated signaling.

Accordingly, the present disclosure provides a method for treating or preventing or delaying progression or reducing or inhibiting or hindering development of a complication associated with sickle cell disease in a subject suffering from sickle cell disease, the method comprising administering to the subject a compound that inhibits granulocyte colony stimulating factor (G-CSF) signaling and/or G-CSF activity. The present disclosure also provides a compound that inhibits G-CSF signaling and/or G-CSF activity for use in treating or preventing or delaying progression or reducing or inhibiting or hindering development of a complication associated with sickle cell disease in a subject suffering from sickle cell disease. The present disclosure further provides use of a compound that inhibits G-CSF signaling and/or G-CSF activity in the manufacture of a medicament for treating or preventing or delaying progression or reducing or inhibiting or hindering development of a complication associated with sickle cell disease in a subject suffering from sickle cell disease.

The present disclosure provides a method for treating or preventing or delaying progression or reducing or inhibiting or hindering development of a complication associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in treating or preventing or delaying progression or reducing or inhibiting or hindering development of a complication associated with sickle cell disease in a subject suffering from sickle cell disease. The present disclosure further provides use of a compound that inhibits G-CSF signaling in the manufacture of a medicament for treating or preventing or delaying progression or reducing or inhibiting or hindering development of a complication associated with sickle cell disease in a subject suffering from sickle cell disease.

The present disclosure also provides a method for treating or preventing or delaying progression or reducing or inhibiting or hindering development of a complication associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in treating or preventing or delaying progression or reducing or inhibiting or hindering development of a complication associated with sickle cell disease in a subject suffering from sickle cell disease. The present disclosure further provides use of a compound that inhibits G-CSF activity in the manufacture of a medicament for treating or preventing or delaying progression or reducing or inhibiting or hindering development of a complication associated with sickle cell disease in a subject suffering from sickle cell disease.

The present disclosure provides a method for treating a complication associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in treating a complication associated with sickle cell disease in a subject suffering from sickle cell disease. The present disclosure further provides use of a compound that inhibits G-CSF signaling in the manufacture of a medicament for treating a complication associated with sickle cell disease in a subject suffering from sickle cell disease.

The present disclosure provides a method for treating a complication associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in treating a complication associated with sickle cell disease in a subject suffering from sickle cell disease. The present disclosure further provides use of a compound that inhibits G-CSF activity in the manufacture of a medicament for treating a complication associated with sickle cell disease in a subject suffering from sickle cell disease.

The present disclosure provides a method for preventing a complication associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in preventing a complication associated with sickle cell disease in a subject suffering from sickle cell disease. The present disclosure further provides use of a compound that inhibits G-CSF signaling in the manufacture of a medicament for preventing a complication associated with sickle cell disease in a subject suffering from sickle cell disease.

The present disclosure provides a method for preventing a complication associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in preventing a complication associated with sickle cell disease in a subject suffering from sickle cell disease. The present disclosure further provides use of a compound that inhibits G-CSF activity in the manufacture of a medicament for preventing a complication associated with sickle cell disease in a subject suffering from sickle cell disease.

The present disclosure provides a method for delaying progression of a complication associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in delaying progression of a complication associated with sickle cell disease in a subject suffering from sickle cell disease. The present disclosure further provides use of a compound that inhibits G-CSF signaling in the manufacture of a medicament for delaying progression of a complication associated with sickle cell disease in a subject suffering from sickle cell disease.

The present disclosure provides a method for delaying progression of a complication associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in delaying progression of a complication associated with sickle cell disease in a subject suffering from sickle cell disease. The present disclosure further provides use of a compound that inhibits G-CSF activity in the manufacture of a medicament for delaying progression of a complication associated with sickle cell disease in a subject suffering from sickle cell disease.

The present disclosure provides a method for reducing or inhibiting or hindering development of a complication associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in reducing or inhibiting or hindering development of a complication associated with sickle cell disease in a subject suffering from sickle cell disease. The present disclosure further provides use of a compound that inhibits G-CSF signaling in the manufacture of a medicament for reducing or inhibiting or hindering development of a complication associated with sickle cell disease in a subject suffering from sickle cell disease.

The present disclosure provides a method for reducing or inhibiting or hindering development of a complication associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in reducing or inhibiting or hindering development of a complication associated with sickle cell disease in a subject suffering from sickle cell disease. The present disclosure further provides use of a compound that inhibits G-CSF activity in the manufacture of a medicament for reducing or inhibiting or hindering development of a complication associated with sickle cell disease in a subject suffering from sickle cell disease.

In one example, the compound reduces and/or prevents and/or inhibits neutrophil activation, neutrophil extracellular trap (NET) activation and/or endothelial cell activation.

The present disclosure also provides a method of reducing and/or preventing and/or inhibiting neutrophil activation, neutrophil extracellular trap (NET) activation and/or endothelial cell activation in a subject suffering from sickle cell disease or a complication associated with sickle cell disease, the method comprising administering to the subject a compound that inhibits granulocyte colony stimulating factor (G-CSF) signaling and/or G-CSF activity. The present disclosure also provides a compound that inhibits G-CSF signaling and/or G-CSF activity for use in reducing and/or preventing and/or inhibiting neutrophil activation, neutrophil extracellular trap (NET) activation and/or endothelial cell activation in a subject suffering from sickle cell disease or a complication associated with sickle cell disease. The present disclosure further provides use of a compound that inhibits G-CSF signaling and/or G-CSF activity in the manufacture of a medicament for reducing and/or preventing and/or inhibiting neutrophil activation, neutrophil extracellular trap (NET) activation and/or endothelial cell activation in a subject suffering from sickle cell disease or a complication associated with sickle cell disease.

The present disclosure also provides a method of reducing and/or preventing and/or inhibiting neutrophil activation, neutrophil extracellular trap (NET) activation and/or endothelial cell activation in a subject suffering from sickle cell disease or a complication associated with sickle cell disease, the method comprising administering to the subject a compound that inhibits granulocyte colony stimulating factor (G-CSF) signaling. The present disclosure also provides a compound that inhibits G-CSF signaling for use in reducing and/or preventing and/or inhibiting neutrophil activation, neutrophil extracellular trap (NET) activation and/or endothelial cell activation in a subject suffering from sickle cell disease or a complication associated with sickle cell disease. The present disclosure further provides use of a compound that inhibits G-CSF signaling in the manufacture of a medicament for reducing and/or preventing and/or inhibiting neutrophil activation, neutrophil extracellular trap (NET) activation and/or endothelial cell activation in a subject suffering from sickle cell disease or a complication associated with sickle cell disease.

The present disclosure also provides a method of reducing and/or preventing and/or inhibiting neutrophil activation, neutrophil extracellular trap (NET) activation and/or endothelial cell activation in a subject suffering from sickle cell disease or a complication associated with sickle cell disease, the method comprising administering to the subject a compound that inhibits granulocyte colony stimulating factor (G-CSF) activity. The present disclosure also provides a compound that inhibits G-CSF activity for use in reducing and/or preventing and/or inhibiting neutrophil activation, neutrophil extracellular trap (NET) activation and/or endothelial cell activation in a subject suffering from sickle cell disease or a complication associated with sickle cell disease. The present disclosure further provides use of a compound that inhibits G-CSF activity in the manufacture of a medicament for reducing and/or preventing and/or inhibiting neutrophil activation, neutrophil extracellular trap (NET) activation and/or endothelial cell activation in a subject suffering from sickle cell disease or a complication associated with sickle cell disease.

The present disclosure also provides a method of reducing and/or preventing and/or inhibiting neutrophil activation in a subject suffering from sickle cell disease or a complication associated with sickle cell disease, the method comprising administering to the subject a compound that inhibits granulocyte colony stimulating factor (G-CSF) signaling. The present disclosure also provides a compound that inhibits G-CSF signaling for use in reducing and/or preventing and/or inhibiting neutrophil activation in a subject suffering from sickle cell disease or a complication associated with sickle cell disease. The present disclosure further provides use of a compound that inhibits G-CSF signaling in the manufacture of a medicament for reducing and/or preventing and/or inhibiting neutrophil activation in a subject suffering from sickle cell disease or a complication associated with sickle cell disease.

The present disclosure also provides a method of reducing and/or preventing and/or inhibiting neutrophil activation in a subject suffering from sickle cell disease or a complication associated with sickle cell disease, the method comprising administering to the subject a compound that inhibits granulocyte colony stimulating factor (G-CSF) activity. The present disclosure also provides a compound that inhibits G-CSF activity for use in reducing and/or preventing and/or inhibiting neutrophil activation in a subject suffering from sickle cell disease or a complication associated with sickle cell disease. The present disclosure further provides use of a compound that inhibits G-CSF activity in the manufacture of a medicament for reducing and/or preventing and/or inhibiting neutrophil activation in a subject suffering from sickle cell disease or a complication associated with sickle cell disease.

The present disclosure also provides a method of reducing and/or preventing and/or inhibiting neutrophil extracellular trap (NET) activation in a subject suffering from sickle cell disease or a complication associated with sickle cell disease, the method comprising administering to the subject a compound that inhibits granulocyte colony stimulating factor (G-CSF) signaling. The present disclosure also provides a compound that inhibits G-CSF signaling for use in reducing and/or preventing and/or inhibiting neutrophil extracellular trap (NET) activation in a subject suffering from sickle cell disease or a complication associated with sickle cell disease. The present disclosure further provides use of a compound that inhibits G-CSF signaling in the manufacture of a medicament for reducing and/or preventing and/or inhibiting neutrophil extracellular trap (NET) activation in a subject suffering from sickle cell disease or a complication associated with sickle cell disease.

The present disclosure also provides a method of reducing and/or preventing and/or inhibiting neutrophil extracellular trap (NET) activation in a subject suffering from sickle cell disease or a complication associated with sickle cell disease, the method comprising administering to the subject a compound that inhibits granulocyte colony stimulating factor (G-CSF) activity. The present disclosure also provides a compound that inhibits G-CSF activity for use in reducing and/or preventing and/or inhibiting neutrophil extracellular trap (NET) activation in a subject suffering from sickle cell disease or a complication associated with sickle cell disease. The present disclosure further provides use of a compound that inhibits G-CSF activity in the manufacture of a medicament for reducing and/or preventing and/or inhibiting neutrophil extracellular trap (NET) activation in a subject suffering from sickle cell disease or a complication associated with sickle cell disease.

The present disclosure also provides a method of reducing and/or preventing and/or inhibiting endothelial cell activation in a subject suffering from sickle cell disease or a complication associated with sickle cell disease, the method comprising administering to the subject a compound that inhibits granulocyte colony stimulating factor (G-CSF) signaling. The present disclosure also provides a compound that inhibits G-CSF signaling for use in reducing and/or preventing and/or inhibiting endothelial cell activation in a subject suffering from sickle cell disease or a complication associated with sickle cell disease. The present disclosure further provides use of a compound that inhibits G-CSF signaling in the manufacture of a medicament for reducing and/or preventing and/or inhibiting endothelial cell activation in a subject suffering from sickle cell disease or a complication associated with sickle cell disease.

The present disclosure also provides a method of reducing and/or preventing and/or inhibiting endothelial cell activation in a subject suffering from sickle cell disease or a complication associated with sickle cell disease, the method comprising administering to the subject a compound that inhibits granulocyte colony stimulating factor (G-CSF) activity. The present disclosure also provides a compound that inhibits G-CSF activity for use in reducing and/or preventing and/or inhibiting endothelial cell activation in a subject suffering from sickle cell disease or a complication associated with sickle cell disease. The present disclosure further provides use of a compound that inhibits G-CSF activity in the manufacture of a medicament for reducing and/or preventing and/or inhibiting endothelial cell activation in a subject suffering from sickle cell disease or a complication associated with sickle cell disease.

In one example, the complication associated with sickle cell disease is acute or chronic. For example, the complication associated with sickle cell disease is acute. In another example, the complication associated with sickle cell disease is chronic.

In one example, the complication associated with sickle cell disease affects the cardiovascular system, the central nervous system, the dental system, endocrine system, gallbladder and/or pancreas, gastrointestinal system, genitourinary system, hematopoietic system, hepatic system, immune system, ophthalmic system, pulmonary system, renal system, reproductive system, skin and/or spleen.

In one example, the subject has or is suffering from a complication associated with sickle cell disease (i.e., is in need of treatment).

In one example, the complication associated with sickle cell disease is selected from the group consisting of fatigue, dyspnea, syncope, relative systolic hypertension, myocardial infarction, acute myocardial infarction, tissue infarction, sickle cardiomyopathy, left ventricular hypertrophy, diastolic dysfunction, heart failure with preserved ejection fraction, iron-induced cardiomyopathy and dysrhythmias, endothelial dysfunction/autonomic dysfunction, prolonged QT interval, pulmonary hypertension, headache, infarctive stroke, hemorrhagic stroke, ischemic stroke, aneurysm, ruptured aneurysm, moyamoya syndrome, silent cerebral infarct, sino-venous thrombosis, ischemia-reperfusion injury, chronic headache, neurocognitive disorders due to silent cerebral infarcts/overt cerebrovascular accidents or strokes, intraparenchymal hemorrhage, subarachnoid hemorrhage, intraventricular hemorrhage, chronic anemia, anemia crisis, poor executive functioning, memory deficits, increased cerebral blood flow, blood transfusion requirement, organ damage, pain medicine requirement, vasculopathy, cerebral vasculopathy, microvascular stasis, vaso-occlusion, vaso-occlusive crisis (VOC), vascular stasis, venous stasis, moyamoya syndrome, cerebral aneurysm, dental abscess, dental crown fracture, dental pulp fracture, dental caries, gingivitis, cracked teeth, early dental loss, misaligned dentition, pain around menses, pregnancy, menopause, growth hormone deficiency, hypogonadism, disturbances in cortisol levels, delayed puberty, premature menopause, cholelithiasis, cholecystitis, common bile duct obstruction, acute pancreatitis, chronic gallbladder sludge, dyspepsia, chronic cholecystitis, chronic pancreatitis, mesenteric infarcts, chronic abdominal pain, constipation, irritable bowel syndrome, GERD, increased abdominal girth due to shortened trunk and barrel chest (sickle-habitus), priapism, enuresis, hematuria, menses-induced VOE, erectile (sexual) dysfunction, postcoital pain, enuresis/nocturia, hematuria, acute anemia, aplastic crisis, sequestration crises, splenic sequestration crisis, hyperhemolytic crisis, functional asplenia, indirect hyperbilirubinemia, scleral icterus, hemostatic activation, chronic hemolysis, chronic anemia, extramedullary hematopoiesis, leukocytosis, thrombocytosis, splenomegaly, hypersplenism, conjunctival pallor, scleral icterus, hemostatic activation, thrombophilia, hyperbilirubinemia, hepatic sequestration, hepatitis, acute intrahepatic cholelithiasis/cholestasis, acute and/or chronic renal failure, transaminitis, hepatic failure, hepatomegaly, hepatic congestion/chronic congestive hepatopathy, hepatic sequestration, portal hypertension, nephropathy, bacteremia/sepsis, iron overload, meningitis, hepatitis, osteomyelitis, pyelonephritis, influenza, osteomyelitis, hepatitis, dental abscesses, gingivitis, leg ulcer super infection, retinal detachment, retinal artery occlusion, vitreous hemorrhage, peripheral retinal ischemia, macular infarction, sickle retinopathy (proliferative and nonproliferative), maculopathy, chest syndrome, acute chest syndrome, pneumonia, pulmonary fat embolism syndrome, airway hyperreactivity, atelectasis from hypoventilation, pulmonary embolism, chronic lung disease, chronic hypoxemia/hypoxia, nocturnal hypoxemia, chronic pulmonary embolism, acute kidney injury (recurrent), hematuria, papillary necrosis, hypertension, thromboemboli, glomerular hyperfiltration, proteinuria/microalbuminuria, hyposthenuria, chronic kidney disease, end-stage renal disease, renal tubular acidosis, renal osteodystrophy, spontaneous abortion/miscarriages, intrauterine growth retardation, early fetal demise, pre- and post-eclampsia, severe dilutional anemia, other maternal-fetal complications, low sperm counts/poor sperm function, post-pregnancy chronic pain, leg ulcers, varicosity, acute splenic sequestration, acute splenic infarction, splenic abscesses, traumatic spleen rupture, functional asplenia or hyposplenia due to auto-infarction of spleen leading to increased risk for infection with encapsulated organisms, splenic infarction, hypersplenism, pain crisis and combinations thereof.

The present disclosure provides a method for treating or preventing or delaying progression or reducing or inhibiting or hindering development of a vasculopathy associated with sickle cell disease in a subject suffering from sickle cell disease, the method comprising administering to the subject a compound that inhibits granulocyte colony stimulating factor (G-CSF) signaling and/or activity. The present disclosure also provides a compound that inhibits G-CSF signaling and/or activity for use in treating or preventing or delaying progression or reducing or inhibiting or hindering development of a vasculopathy associated with sickle cell disease in a subject suffering from sickle cell disease. The present disclosure further provides use of a compound that inhibits G-CSF signaling and/or activity in the manufacture of a medicament for treating or preventing or delaying progression or reducing or inhibiting or hindering development of a vasculopathy associated with sickle cell disease in a subject suffering from sickle cell disease.

The present disclosure provides a method for treating or preventing or delaying progression or reducing or inhibiting or hindering development of a vasculopathy associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in treating or preventing or delaying progression or reducing or inhibiting or hindering development of a vasculopathy associated with sickle cell disease in a subject suffering from sickle cell disease. The present disclosure further provides use of a compound that inhibits G-CSF signaling in the manufacture of a medicament for treating or preventing or delaying progression or reducing or inhibiting or hindering development of a vasculopathy associated with sickle cell disease in a subject suffering from sickle cell disease.

The present disclosure provides a method for treating or preventing or delaying progression or reducing or inhibiting or hindering development of a vasculopathy associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in treating or preventing or delaying progression or reducing or inhibiting or hindering development of a vasculopathy associated with sickle cell disease in a subject suffering from sickle cell disease. The present disclosure further provides use of a compound that inhibits G-CSF activity in the manufacture of a medicament for treating or preventing or delaying progression or reducing or inhibiting or hindering development of a vasculopathy associated with sickle cell disease in a subject suffering from sickle cell disease.

The present disclosure provides a method for treating a vasculopathy associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in treating a vasculopathy associated with sickle cell disease in a subject suffering from sickle cell disease. The present disclosure further provides use of a compound that inhibits G-CSF signaling in the manufacture of a medicament for treating a vasculopathy associated with sickle cell disease in a subject suffering from sickle cell disease.

The present disclosure provides a method for treating a vasculopathy associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in treating a vasculopathy associated with sickle cell disease in a subject suffering from sickle cell disease. The present disclosure further provides use of a compound that inhibits G-CSF activity in the manufacture of a medicament for treating a vasculopathy associated with sickle cell disease in a subject suffering from sickle cell disease.

The present disclosure provides a method for preventing a vasculopathy associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in preventing a vasculopathy associated with sickle cell disease in a subject suffering from sickle cell disease. The present disclosure further provides use of a compound that inhibits G-CSF signaling in the manufacture of a medicament for preventing a vasculopathy associated with sickle cell disease in a subject suffering from sickle cell disease.

The present disclosure provides a method for preventing a vasculopathy associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in preventing a vasculopathy associated with sickle cell disease in a subject suffering from sickle cell disease. The present disclosure further provides use of a compound that inhibits G-CSF activity in the manufacture of a medicament for preventing a vasculopathy associated with sickle cell disease in a subject suffering from sickle cell disease.

The present disclosure provides a method for delaying progression of a vasculopathy associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in delaying progression of a vasculopathy associated with sickle cell disease in a subject suffering from sickle cell disease. The present disclosure further provides use of a compound that inhibits G-CSF signaling in the manufacture of a medicament for delaying progression of a vasculopathy associated with sickle cell disease in a subject suffering from sickle cell disease.

The present disclosure provides a method for delaying progression of a vasculopathy associated with sickle cell disease in a subject suffering from sickle cell disease, the method comprising administering to the subject a compound that inhibits granulocyte colony stimulating factor (G-CSF)

activity. The present disclosure also provides a compound that inhibits G-CSF activity for use in delaying progression of a vasculopathy associated with sickle cell disease in a subject suffering from sickle cell disease. The present disclosure further provides use of a compound that inhibits G-CSF activity in the manufacture of a medicament for delaying progression of a vasculopathy associated with sickle cell disease in a subject suffering from sickle cell disease.

The present disclosure provides a method for reducing or inhibiting or hindering development of a vasculopathy associated with sickle cell disease in a subject suffering from sickle cell disease, the method comprising administering to the subject a compound that inhibits granulocyte colony stimulating factor (G-CSF) signaling. The present disclosure also provides a compound that inhibits G-CSF signaling for use in reducing or inhibiting or hindering development of a vasculopathy associated with sickle cell disease in a subject suffering from sickle cell disease. The present disclosure further provides use of a compound that inhibits G-CSF signaling in the manufacture of a medicament for reducing or inhibiting or hindering development of a vasculopathy associated with sickle cell disease in a subject suffering from sickle cell disease.

The present disclosure provides a method for reducing or inhibiting or hindering development of a vasculopathy associated with sickle cell disease in a subject suffering from sickle cell disease, the method comprising administering to the subject a compound that inhibits granulocyte colony stimulating factor (G-CSF) activity. The present disclosure also provides a compound that inhibits G-CSF activity for use in reducing or inhibiting or hindering development of a vasculopathy associated with sickle cell disease in a subject suffering from sickle cell disease. The present disclosure further provides use of a compound that inhibits G-CSF activity in the manufacture of a medicament for reducing or inhibiting or hindering development of a vasculopathy associated with sickle cell disease in a subject suffering from sickle cell disease.

In one example, the vasculopathy is associated with vaso-occlusion or hemolysis-endothelial dysfunction. In one example, the vasculopathy is associated with vaso-occlusion. In one example, the vasculopathy is associated with hemolysis-endothelial dysfunction.

In one example, the subject has or is suffering from a complication of the vaso-occlusion (i.e., the subject is in need to treatment).

In one example, the subject is at risk of suffering from a complication of the vaso-occlusion. Risk factors for a subject at risk of a complication of the vaso-occlusion will be apparent to the skilled person and/or described herein. In one example, the subject has one or more risk factors of a complication of vaso-occlusion selected from the group consisting of infection, dehydration, hypoxia, emotional stress, pregnancy, alcohol intoxication, acidosis, plasma hypertonicity, excessive exercise or exertion, hypovolemia exposure to environmental heat or cold, fatigue vomiting, nausea, viral illness, asthma, infection, fat embolism, a history of pain episodes and combinations thereof.

In one example, the complication of the vaso-occlusion is a vaso-occlusive crisis, acute chest syndrome, osteonecrosis, progressive retinopathy, chronic renal failure, pulmonary hypertension, priapism, splenic sequestration and/or stroke. In one example, the complication of the vaso-occlusion is a vaso-occlusive crisis. In another example, the complication of the vaso-occlusion is acute chest syndrome. In a further example, the complication of the vaso-occlusion is osteonecrosis. In one example, the complication of the vaso-occlusion is progressive retinopathy. In another example, the complication of the vaso-occlusion is chronic renal failure. In a further example, the complication of the vaso-occlusion is pulmonary hypertension. In one example, the complication of the vaso-occlusion is priapism. In another example, the complication of the vaso-occlusion is splenic sequestration. In a further example, the complication of the vaso-occlusion is stroke.

The present disclosure also provides a method of treating or preventing or delaying progression or reducing or inhibiting or hindering development of a vaso-occlusive crisis and/or acute chest syndrome in a subject suffering from sickle cell disease, the method comprising administering to the subject a compound that inhibits granulocyte colony stimulating factor (G-CSF) signaling and/or activity. The present disclosure also provides a compound that inhibits G-CSF signaling and/or activity for use in treating or preventing or delaying progression or reducing or inhibiting or hindering development of a vaso-occlusive crisis and/or acute chest syndrome in a subject suffering from sickle cell disease. The present disclosure further provides use of a compound that inhibits G-CSF signaling and/or activity in the manufacture of a medicament for treating or preventing or delaying progression or reducing or inhibiting or hindering development of a vaso-occlusive crisis and/or acute chest syndrome in a subject suffering from sickle cell disease.

The present disclosure also provides a method of treating or preventing or delaying progression or reducing or inhibiting or hindering development of a vaso-occlusive crisis and/or acute chest syndrome in a subject suffering from sickle cell disease, the method comprising administering to the subject a compound that inhibits granulocyte colony stimulating factor (G-CSF) signaling. The present disclosure also provides a compound that inhibits G-CSF signaling for use in treating or preventing or delaying progression or reducing or inhibiting or hindering development of a vaso-occlusive crisis and/or acute chest syndrome in a subject suffering from sickle cell disease. The present disclosure further provides use of a compound that inhibits G-CSF signaling in the manufacture of a medicament for treating or preventing or delaying progression or reducing or inhibiting or hindering development of a vaso-occlusive crisis and/or acute chest syndrome in a subject suffering from sickle cell disease.

The present disclosure also provides a method of treating or preventing or delaying progression or reducing or inhibiting or hindering development of a vaso-occlusive crisis and/or acute chest syndrome in a subject suffering from sickle cell disease, the method comprising administering to the subject a compound that inhibits granulocyte colony stimulating factor (G-CSF) activity. The present disclosure also provides a compound that inhibits G-CSF activity for use in treating or preventing or delaying progression or reducing or inhibiting or hindering development of a vaso-occlusive crisis and/or acute chest syndrome in a subject suffering from sickle cell disease. The present disclosure further provides use of a compound that inhibits G-CSF activity in the manufacture of a medicament for treating or preventing or delaying progression or reducing or inhibiting or hindering development of a vaso-occlusive crisis and/or acute chest syndrome in a subject suffering from sickle cell disease.

The present disclosure also provides a method of treating or preventing or delaying progression or reducing or inhibiting or hindering development of a vaso-occlusive crisis in a subject suffering from sickle cell disease, the method comprising administering to the subject a compound that inhibits granulocyte colony stimulating factor (G-CSF) signaling. The present disclosure also provides a compound that inhibits G-CSF signaling for use in treating or preventing or delaying progression or reducing or inhibiting or hindering development of a vaso-occlusive crisis in a subject suffering from sickle cell disease. The present disclosure further provides use of a compound that inhibits G-CSF signaling in the manufacture of a medicament for treating or preventing or delaying progression or reducing or inhibiting or hindering development of a vaso-occlusive crisis in a subject suffering from sickle cell disease.

The present disclosure also provides a method of treating or preventing or delaying progression or reducing or inhibiting or hindering development of a vaso-occlusive crisis in a subject suffering from sickle cell disease, the method comprising administering to the subject a compound that inhibits granulocyte colony stimulating factor (G-CSF) activity. The present disclosure also provides a compound that inhibits G-CSF activity for use in treating or preventing or delaying progression or reducing or inhibiting or hindering development of a vaso-occlusive crisis in a subject suffering from sickle cell disease. The present disclosure further provides use of a compound that inhibits G-CSF activity in the manufacture of a medicament for treating or preventing or delaying progression or reducing or inhibiting or hindering development of a vaso-occlusive crisis in a subject suffering from sickle cell disease.

The present disclosure also provides a method of treating a vaso-occlusive crisis in a subject suffering from sickle cell disease, the method comprising administering to the subject a compound that inhibits granulocyte colony stimulating factor (G-CSF) signaling. The present disclosure also provides a compound that inhibits G-CSF signaling for use in treating a vaso-occlusive crisis in a subject suffering from sickle cell disease. The present disclosure further provides use of a compound that inhibits G-CSF signaling in the manufacture of a medicament for treating a vaso-occlusive crisis in a subject suffering from sickle cell disease.

The present disclosure also provides a method of treating a vaso-occlusive crisis in a subject suffering from sickle cell disease, the method comprising administering to the subject a compound that inhibits granulocyte colony stimulating factor (G-CSF) activity. The present disclosure also provides a compound that inhibits G-CSF activity for use in treating a vaso-occlusive crisis in a subject suffering from sickle cell disease. The present disclosure further provides use of a compound that inhibits G-CSF activity in the manufacture of a medicament for treating a vaso-occlusive crisis in a subject suffering from sickle cell disease.

The present disclosure also provides a method of preventing a vaso-occlusive crisis in a subject suffering from sickle cell disease, the method comprising administering to the subject a compound that inhibits granulocyte colony stimulating factor (G-CSF) signaling. The present disclosure also provides a compound that inhibits G-CSF signaling for use in preventing a vaso-occlusive crisis in a subject suffering from sickle cell disease. The present disclosure further provides use of a compound that inhibits G-CSF signaling in the manufacture of a medicament for preventing a vaso-occlusive crisis in a subject suffering from sickle cell disease.

The present disclosure also provides a method of preventing a vaso-occlusive crisis in a subject suffering from sickle cell disease, the method comprising administering to the subject a compound that inhibits granulocyte colony stimulating factor (G-CSF) activity. The present disclosure also provides a compound that inhibits G-CSF activity for use in preventing a vaso-occlusive crisis in a subject suffering from sickle cell disease. The present disclosure further provides use of a compound that inhibits G-CSF activity in the manufacture of a medicament for preventing a vaso-occlusive crisis in a subject suffering from sickle cell disease.

The present disclosure also provides a method of delaying progression of a vaso-occlusive crisis in a subject suffering from sickle cell disease, the method comprising administering to the subject a compound that inhibits granulocyte colony stimulating factor (G-CSF) signaling. The present disclosure also provides a compound that inhibits G-CSF signaling for use in delaying progression of a vaso-occlusive crisis in a subject suffering from sickle cell disease. The present disclosure further provides use of a compound that inhibits G-CSF signaling in the manufacture of a medicament for delaying progression of a vaso-occlusive crisis in a subject suffering from sickle cell disease.

The present disclosure also provides a method of delaying progression of a vaso-occlusive crisis in a subject suffering from sickle cell disease, the method comprising administering to the subject a compound that inhibits granulocyte colony stimulating factor (G-CSF) activity. The present disclosure also provides a compound that inhibits G-CSF activity for use in delaying progression of a vaso-occlusive crisis in a subject suffering from sickle cell disease. The present disclosure further provides use of a compound that inhibits G-CSF activity in the manufacture of a medicament for delaying progression of a vaso-occlusive crisis in a subject suffering from sickle cell disease.

The present disclosure also provides a method of reducing or inhibiting or hindering development of a vaso-occlusive crisis in a subject suffering from sickle cell disease, the method comprising administering to the subject a compound that inhibits granulocyte colony stimulating factor (G-CSF) signaling. The present disclosure also provides a compound that inhibits G-CSF signaling for use in reducing or inhibiting or hindering development of a vaso-occlusive crisis in a subject suffering from sickle cell disease. The present disclosure further provides use of a compound that inhibits G-CSF signaling in the manufacture of a medicament for reducing or inhibiting or hindering development of a vaso-occlusive crisis in a subject suffering from sickle cell disease.

The present disclosure also provides a method of reducing or inhibiting or hindering development of a vaso-occlusive crisis in a subject suffering from sickle cell disease, the method comprising administering to the subject a compound that inhibits granulocyte colony stimulating factor (G-CSF) activity. The present disclosure also provides a compound that inhibits G-CSF activity for use in reducing or inhibiting or hindering development of a vaso-occlusive crisis in a subject suffering from sickle cell disease. The present disclosure further provides use of a compound that inhibits G-CSF activity in the manufacture of a medicament for reducing or inhibiting or hindering development of a vaso-occlusive crisis in a subject suffering from sickle cell disease.

The present disclosure also provides a method of treating or preventing or delaying progression or reducing or inhibiting or hindering development of acute chest syndrome in a subject suffering from sickle cell disease, the method comprising administering to the subject a compound that inhibits granulocyte colony stimulating factor (G-CSF) signaling and/or activity. The present disclosure also provides a compound that inhibits G-CSF signaling and/or activity for use in treating or preventing or delaying progression or reducing or inhibiting or hindering development of acute chest syndrome in a subject suffering from sickle cell disease. The present disclosure further provides use of a compound that inhibits G-CSF signaling and/or activity in the manufacture of a medicament for treating or preventing or delaying progression or reducing or inhibiting or hindering development of acute chest syndrome in a subject suffering from sickle cell disease.

The present disclosure also provides a method of treating or preventing or delaying progression or reducing or inhibiting or hindering development of acute chest syndrome in a subject suffering from sickle cell disease, the method comprising administering to the subject a compound that inhibits granulocyte colony stimulating factor (G-CSF) signaling. The present disclosure also provides a compound that inhibits G-CSF signaling for use in treating or preventing or delaying progression or reducing or inhibiting or hindering development of acute chest syndrome in a subject suffering from sickle cell disease. The present disclosure further provides use of a compound that inhibits G-CSF signaling in the manufacture of a medicament for treating or preventing or delaying progression or reducing or inhibiting or hindering development of acute chest syndrome in a subject suffering from sickle cell disease.

The present disclosure also provides a method of treating or preventing or delaying progression or reducing or inhibiting or hindering development of acute chest syndrome in a subject suffering from sickle cell disease, the method comprising administering to the subject a compound that inhibits granulocyte colony stimulating factor (G-CSF) activity. The present disclosure also provides a compound that inhibits G-CSF activity for use in treating or preventing or delaying progression or reducing or inhibiting or hindering development of acute chest syndrome in a subject suffering from sickle cell disease. The present disclosure further provides use of a compound that inhibits G-CSF activity in the manufacture of a medicament for treating or preventing or delaying progression or reducing or inhibiting or hindering development of acute chest syndrome in a subject suffering from sickle cell disease.

The present disclosure also provides a method of treating acute chest syndrome in a subject suffering from sickle cell disease, the method comprising administering to the subject a compound that inhibits granulocyte colony stimulating factor (G-CSF) signaling. The present disclosure also provides a compound that inhibits G-CSF signaling for use in treating acute chest syndrome in a subject suffering from sickle cell disease. The present disclosure further provides use of a compound that inhibits G-CSF signaling in the manufacture of a medicament for treating acute chest syndrome in a subject suffering from sickle cell disease.

The present disclosure also provides a method of treating acute chest syndrome in a subject suffering from sickle cell disease, the method comprising administering to the subject a compound that inhibits granulocyte colony stimulating factor (G-CSF) activity. The present disclosure also provides a compound that inhibits G-CSF activity for use in treating acute chest syndrome in a subject suffering from sickle cell disease. The present disclosure further provides use of a compound that inhibits G-CSF activity in the manufacture of a medicament for treating acute chest syndrome in a subject suffering from sickle cell disease.

The present disclosure also provides a method of preventing acute chest syndrome in a subject suffering from sickle cell disease, the method comprising administering to the subject a compound that inhibits granulocyte colony stimulating factor (G-CSF) signaling. The present disclosure also provides a compound that inhibits G-CSF signaling for use in preventing acute chest syndrome in a subject suffering from sickle cell disease. The present disclosure further provides use of a compound that inhibits G-CSF signaling in the manufacture of a medicament for preventing acute chest syndrome in a subject suffering from sickle cell disease.

The present disclosure also provides a method of preventing acute chest syndrome in a subject suffering from sickle cell disease, the method comprising administering to the subject a compound that inhibits granulocyte colony stimulating factor (G-CSF) activity. The present disclosure also provides a compound that inhibits G-CSF activity for use in preventing acute chest syndrome in a subject suffering from sickle cell disease. The present disclosure further provides use of a compound that inhibits G-CSF activity in the manufacture of a medicament for preventing acute chest syndrome in a subject suffering from sickle cell disease.

The present disclosure also provides a method of delaying progression of acute chest syndrome in a subject suffering from sickle cell disease, the method comprising administering to the subject a compound that inhibits granulocyte colony stimulating factor (G-CSF) signaling. The present disclosure also provides a compound that inhibits G-CSF signaling for use in delaying progression of acute chest syndrome in a subject suffering from sickle cell disease. The present disclosure further provides use of a compound that inhibits G-CSF signaling in the manufacture of a medicament for delaying progression of acute chest syndrome in a subject suffering from sickle cell disease.

The present disclosure also provides a method of delaying progression of acute chest syndrome in a subject suffering from sickle cell disease, the method comprising administering to the subject a compound that inhibits granulocyte colony stimulating factor (G-CSF) activity. The present disclosure also provides a compound that inhibits G-CSF activity for use in delaying progression of acute chest syndrome in a subject suffering from sickle cell disease. The present disclosure further provides use of a compound that inhibits G-CSF activity in the manufacture of a medicament for delaying progression of acute chest syndrome in a subject suffering from sickle cell disease.

The present disclosure also provides a method of reducing or inhibiting or hindering development of acute chest syndrome in a subject suffering from sickle cell disease, the method comprising administering to the subject a compound that inhibits granulocyte colony stimulating factor (G-CSF) signaling. The present disclosure also provides a compound that inhibits G-CSF signaling for use in reducing or inhibiting or hindering development of acute chest syndrome in a subject suffering from sickle cell disease. The present disclosure further provides use of a compound that inhibits G-CSF signaling in the manufacture of a medicament for reducing or inhibiting or hindering development of acute chest syndrome in a subject suffering from sickle cell disease.

The present disclosure also provides a method of reducing or inhibiting or hindering development of acute chest syndrome in a subject suffering from sickle cell disease, the method comprising administering to the subject a compound that inhibits granulocyte colony stimulating factor (G-CSF) activity. The present disclosure also provides a compound that inhibits G-CSF activity for use in reducing or inhibiting or hindering development of acute chest syndrome in a subject suffering from sickle cell disease. The present disclosure further provides use of a compound that inhibits G-CSF activity in the manufacture of a medicament for reducing or inhibiting or hindering development of acute chest syndrome in a subject suffering from sickle cell disease.

In one example, the compound that inhibits G-CSF signaling is administered in an amount sufficient to reduce the frequency and/or severity of or prevent onset of a complication of sickle cell disease and/or one or more symptoms of a complication associated with sickle cell disease.

In one example of any method described herein, the method reduces the frequency and/or severity of a complication of sickle cell disease. In one example, the method reduces the frequency and/or severity of a vaso-occlusive crisis. In one example, the method reduces the frequency and/or severity of pain associated with vaso-occlusive crisis. In one example, the method reduces the frequency and/or severity of acute chest syndrome. In another example, the method reduces the frequency and/or severity of pain associated with acute chest syndrome.

In one example, the method reduces the frequency of hospitalisations associated with a complication of sickle cell disease. For example, the method reduces the frequency of hospitalisations associated with a vaso-occlusion in a subject suffering from sickle cell disease. In one example, the method reduces the frequency of hospitalisations associated with a vaso-occlusive crisis in a subject suffering from sickle cell disease. For example, the method reduces the frequency of hospitalisations of a subject with sickle cell disease suffering from pain associated with a vaso-occlusive crisis. In another example, the method reduces the frequency of hospitalisations associated with acute chest syndrome in a subject suffering from sickle cell disease. For example, the method reduces the frequency of hospitalisations of a subject with sickle cell disease suffering from pain associated with acute chest syndrome.

In one example, the subject has or is suffering from pain associated with vaso-occlusive crisis and/or pain associated with acute chest syndrome. For example, the subject has or is suffering from pain associated with vaso-occlusive crisis. In one example, the subject has or is suffering from pain associated with acute chest syndrome.

In one example, the pain is mild, moderate or severe pain. In one example, the pain is mild. In another example, the pain is moderate. In a further example, the pain is severe.

In one example, the sickle cell disease is selected from the group consisting of sickle cell anemia (HbSS), hemoglobin sickle cell disease (HbSC), hemoglobin sickle-beta-thalassemia (Hb S beta-thalassemia), sickle cell-hemoglobin D disease (HbSD), sickle cell-hemoglobin E disease (HbSE) and sickle cell-hemoglobin O disease (HbSO).

In one example, the sickle cell disease is sickle cell anemia (HbSS).

In one example, the sickle cell disease is hemoglobin sickle cell disease (HbSC).

In one example, the sickle cell disease is hemoglobin sickle-beta-thalassemia (Hb S beta-thalassemia). In one example, the subject has Hb S beta$^0$-thalassemia. In another example, the subject has Hb S beta$^+$-thalassemia.

In one example, the sickle cell disease is sickle cell-hemoglobin D disease (HbSD).

In one example, the sickle cell disease is sickle cell-hemoglobin E disease (HbSE).

In one example, the sickle cell disease is sickle cell-hemoglobin O disease (HbSO).

In one example, the method reduces and/or prevents and/or inhibits:
  (i) neutrophil adhesion to endothelial cells and transmigration;
  (ii) neutrophil-platelet aggregate formation;
  (iii) neutrophil extracellular trap (NET) formation;
  (iv) reactive oxygen species formation;
  (v) von Willebrand factor secretion from endothelial cells;
  (vi) neutrophil activation;
  (vii) neutrophil extracellular trap (NET) activation; and/or
  (viii) endothelial cell activation.

In one example, the method reduces and/or prevents and/or inhibits:
  (i) neutrophil-platelet aggregate formation;
  (ii) neutrophil extracellular trap (NET) formation;
  (iii) reactive oxygen species formation;
  (iv) von Willebrand factor secretion from endothelial cells;
  (v) neutrophil activation;
  (vi) neutrophil extracellular trap (NET) activation; and/or
  (vii) endothelial cell activation.

In one example, administration of the compound that inhibits G-CSF signaling reduces and/or prevents and/or inhibits neutrophil adhesion to endothelial cells and transmigration. For example, administration of the compound that inhibits G-CSF signaling reduces and/or prevents and/or inhibits neutrophil adhesion to endothelial cells and transmigration in the subject's liver and/or lung. In one example, administration of the compound that inhibits G-CSF signaling reduces and/or prevents and/or inhibits neutrophil adhesion to endothelial cells and transmigration in the subject's liver. In another example, administration of the compound that inhibits G-CSF signaling reduces and/or prevents and/or inhibits neutrophil adhesion to endothelial cells and transmigration in the subject's lung.

In one example, administration of the compound that inhibits G-CSF signaling reduces and/or prevents and/or inhibits neutrophil-platelet aggregate formation. For example, administration of the compound that inhibits G-CSF signaling reduces and/or prevents and/or inhibits neutrophil-platelet aggregate formation in the subject's liver and/or lung. In one example, administration of the compound that inhibits G-CSF signaling reduces and/or prevents and/or inhibits neutrophil-platelet aggregate formation in the subject's liver. In another example, administration of the compound that inhibits G-CSF signaling reduces and/or prevents and/or inhibits neutrophil-platelet aggregate formation in the subject's lung.

In one example, administration of the compound that inhibits G-CSF signaling reduces and/or prevents and/or inhibits neutrophil extracellular trap (NET) formation. For example, administration of the compound that inhibits G-CSF signaling reduces and/or prevents and/or inhibits neutrophil extracellular trap (NET) formation in the subject's liver and/or lung. In one example, administration of the compound that inhibits G-CSF signaling reduces and/or prevents and/or inhibits neutrophil extracellular trap (NET) formation in the subject's liver. In another example, administration of the compound that inhibits G-CSF signaling reduces and/or prevents and/or inhibits neutrophil extracellular trap (NET) formation in the subject's lung.

In one example, administration of the compound that inhibits G-CSF signaling reduces and/or prevents and/or inhibits reactive oxygen species formation. For example, administration of the compound that inhibits G-CSF signaling reduces and/or prevents and/or inhibits reactive oxygen species formation in the subject's liver and/or lung. In one example, administration of the compound that inhibits G-CSF signaling reduces and/or prevents and/or inhibits reactive oxygen species formation in the subject's liver. In another example, administration of the compound that inhibits G-CSF signaling reduces and/or prevents and/or inhibits reactive oxygen species formation in the subject's lung.

In one example, administration of the compound that inhibits G-CSF signaling reduces and/or prevents and/or inhibits von Willebrand factor secretion from endothelial cells. For example, administration of the compound that inhibits G-CSF signaling reduces and/or prevents and/or inhibits von Willebrand factor secretion from endothelial cells in the subject's liver and/or lung. In one example, administration of the compound that inhibits G-CSF signaling reduces and/or prevents and/or inhibits von Willebrand factor secretion from endothelial cells in the subject's liver. In another example, administration of the compound that inhibits G-CSF signaling reduces and/or prevents and/or inhibits von Willebrand factor secretion from endothelial cells in the subject's lung.

In one example, administration of the compound that inhibits G-CSF signaling reduces and/or prevents and/or inhibits neutrophil activation. For example, administration of the compound that inhibits G-CSF signaling reduces and/or prevents and/or inhibits neutrophil activation in the subject's liver and/or lung. In one example, administration of the compound that inhibits G-CSF signaling reduces and/or prevents and/or inhibits neutrophil activation in the subject's liver. In another example, administration of the compound that inhibits G-CSF signaling reduces and/or prevents and/or inhibits neutrophil activation in the subject's lung.

In one example, administration of the compound that inhibits G-CSF signaling reduces and/or prevents and/or inhibits neutrophil extracellular trap (NET) activation. For example, administration of the compound that inhibits G-CSF signaling reduces and/or prevents and/or inhibits neutrophil extracellular trap (NET) activation in the subject's liver and/or lung. In one example, administration of the compound that inhibits G-CSF signaling reduces and/or prevents and/or inhibits neutrophil extracellular trap (NET) activation in the subject's liver. In another example, administration of the compound that inhibits G-CSF signaling reduces and/or prevents and/or inhibits neutrophil extracellular trap (NET) activation in the subject's lung.

In one example, administration of the compound that inhibits G-CSF signaling reduces and/or prevents and/or inhibits endothelial cell activation. For example, administration of the compound that inhibits G-CSF signaling reduces and/or prevents and/or inhibits endothelial cell activation in the subject's liver and/or lung. In one example, administration of the compound that inhibits G-CSF signaling reduces and/or prevents and/or inhibits endothelial cell activation in the subject's liver. In another example, administration of the compound that inhibits G-CSF signaling reduces and/or prevents and/or inhibits endothelial cell activation in the subject's lung.

Methods for assessing the above will be known in the art and/or described herein. For example, the levels of neutrophils in lung and/or liver tissue can be measured by flow cytometry or immunohistochemistry (e.g., as described in Wang et al., Clin Sci Lond, 2017 131:2347-2362).

In one example, the compound that inhibits G-CSF signaling is administered in an amount sufficient to have one or more of the following effects:
(i) reduce or prevent an increase in percent vascular stasis;
(ii) reduce or prevent an increase in blood flow;
(iii) reduce or inhibit expression of E-selectin on endothelial cells;
(iv) reduce or inhibit expression of vascular cell adhesion molecule 1 (VCAM-1) on endothelial cells;
(v) reduce or inhibit expression of intercellular adhesion molecule 1 (ICAM-1) on endothelial cells;
(vi) reduce or inhibit expression of P-selectin on endothelial cells;
(vii) increase or upregulate expression of heme-oxygenase-1 (HO-1);
(viii) increase or upregulate expression of NF-E2-related factor 2 (NRF2) on endothelial cells; and
(ix) reduce or prevent an increase in neutrophil infiltration and/or accumulation in the subject's liver.

In one example, the compound that inhibits G-CSF signaling is administered in an amount sufficient to have one or more of the following effects:
(i) reduce or prevent an increase in percent vascular stasis;
(ii) reduce or prevent an increase in blood flow;
(iii) reduce or inhibit expression of E-selectin on endothelial cells;
(iv) reduce or inhibit expression of vascular cell adhesion molecule 1 (VCAM-1) on endothelial cells;
(v) reduce or inhibit expression of intercellular adhesion molecule 1 (ICAM-1) on endothelial cells;
(vi) reduce or inhibit expression of P-selectin on endothelial cells;
(vii) increase or upregulate expression of heme-oxygenase-1 (HO-1);
(viii) increase or upregulate expression of NF-E2-related factor 2 (NRF2) on endothelial cells;
(ix) reduce or inhibit expression of CSFR3 in the subject's liver;
(x) reduce or prevent an increase in neutrophil infiltration and/or accumulation in the subject's liver;
(xi) reduce or prevent an increase in total white blood cell count in the subject; and
(xii) reduce or prevent an increase in lymphocyte count in the subject's blood.

In one example, the compound that inhibits G-CSF signaling is administered in an amount sufficient to have one or more of the following effects:
(i) reduce or prevent an increase in percent vascular stasis;
(ii) reduce or inhibit expression of E-selectin on endothelial cells;
(iii) reduce or inhibit expression of vascular cell adhesion molecule 1 (VCAM-1) on endothelial cells;
(iv) reduce or inhibit expression of intercellular adhesion molecule 1 (ICAM-1) on endothelial cells;
(v) reduce or inhibit expression of P-selectin on endothelial cells;
(vi) increase or upregulate expression of heme-oxygenase-1 (HO-1) on endothelial cells;
(vii) increase or upregulate expression of NF-E2-related factor 2 (NRF2) on endothelial cells; and
(viii) reduce or prevent an increase in neutrophil infiltration and/or accumulation in the subject's liver.

In one example, the compound that inhibits G-CSF signaling is administered in an amount sufficient to reduce or prevent an increase in percent vascular stasis. In one example, the compound is administered in an amount sufficient to reduce or prevent an increase in vascular stasis by about 5% to about 90% compared to treatment in the absence of the compound that inhibits G-CSF signaling. For example, the vascular stasis is reduced or inhibited by about 5% to about 90% following administration of the compound compared to in the absence of treatment with the compound that inhibits G-CSF signaling. In one example, the compound that inhibits G-CSF signaling is administered in an amount sufficient to reduce or prevent an increase in vascular stasis by at least 5%. In one example, the compound that inhibits G-CSF signaling is administered in an amount sufficient to reduce or prevent an increase in vascular stasis by at least 10%. In one example, compound is administered in an amount sufficient to reduce or prevent an increase in vascular stasis by at least 15%. In one example, the compound is administered in an amount sufficient to reduce or prevent an increase in vascular stasis by at least 20%. In one example, the compound is administered in an amount sufficient to reduce or prevent an increase in vascular stasis by about 20%. In one example, the compound is administered in an amount sufficient to reduce or prevent an increase in vascular stasis by at least 25%. In one example, the compound is administered in an amount sufficient to reduce or prevent an increase in vascular stasis by about 25%. In one example, the compound is administered in an amount sufficient to reduce or prevent an increase in vascular stasis by at least 30%. In one example, the compound is administered in an amount sufficient to reduce or prevent an increase in vascular stasis by about 30%. In one example, the compound is administered in an amount sufficient to reduce or prevent an increase in vascular stasis by at least 40%. In one example, the compound is administered in an amount sufficient to reduce or prevent an increase in vascular stasis by about 40%. In one example, the compound is administered in an amount sufficient to reduce or prevent an increase in vascular stasis by at least 50%. In one example, the compound is administered in an amount sufficient to reduce or prevent an increase in vascular stasis by about 50%. In one example, the compound is administered in an amount sufficient to reduce or prevent an increase in vascular stasis by at least 60%. In one example, the compound is administered in an amount sufficient to reduce or prevent an increase in vascular stasis by about 60%. In one example, the compound is administered in an amount sufficient to reduce or prevent an increase in vascular stasis by at least 70%. In one example, the compound is administered in an amount sufficient to reduce or prevent an increase in vascular stasis by about 70%. In one example, the compound is administered in an amount sufficient to reduce or prevent an increase in vascular stasis by at least 80%. In one example, the compound is administered in an amount sufficient to reduce or prevent an increase in vascular stasis by about 80%. In one example, the compound is administered in an amount sufficient to reduce or prevent an increase in vascular stasis by at least 90%. In one example, the compound is administered in an amount sufficient to reduce or prevent an increase in vascular stasis by about 90%.

In one example, the compound that inhibits G-CSF signaling is administered in an amount sufficient to reduce or prevent an increase in blood flow.

In one example, the compound that inhibits G-CSF signaling is administered in an amount sufficient to have one or more of the following effects:
(i) reduce or inhibit expression of E-selectin on endothelial cells;
(ii) reduce or inhibit expression of vascular cell adhesion molecule 1 (VCAM-1) on endothelial cells;
(iii) reduce or inhibit expression of intercellular adhesion molecule 1 (ICAM-1) on endothelial cells;
(iv) reduce or inhibit expression of P-selectin on endothelial cells;
(v) increase or upregulate expression of heme-oxygenase-1 (HO-1);
(vi) increase or upregulate expression of NF-E2-related factor 2 (NRF2) on endothelial cells; and
(vii) reduce or prevent an increase in neutrophil infiltration and/or accumulation in the subject's liver.

In one example, the compound that inhibits G-CSF signaling is administered in an amount sufficient to reduce or prevent an increase in total white blood cell count in the subject.

In one example, the compound that inhibits G-CSF signaling is administered in an amount sufficient to reduce or prevent an increase in lymphocyte count in the subject's blood.

In one example, the compound that inhibits G-CSF signaling is administered in an amount sufficient to have one or more of the following effects:
(i) reduce or inhibit expression of vascular cell adhesion molecule 1 (VCAM-1) on endothelial cells;
(ii) reduce or inhibit expression of intercellular adhesion molecule 1 (ICAM-1) on endothelial cells;
(iii) reduce or inhibit expression of CSFR3 in the subject's liver.

In one example, the compound that inhibits G-CSF signaling is administered in an amount sufficient to reduce or prevent an increase in the level of expression of one or more of the following:
E-selectin on endothelial cells;
vascular cell adhesion molecule 1 (VCAM-1) on endothelial cells;
intercellular adhesion molecule 1 (ICAM-1) on endothelial cells; and
P-selectin on endothelial cells.

In one example, the E-selectin is soluble E-selectin (sE-selectin).

In one example, the VCAM-1 is soluble VCAM-1 (sVCAM-1).

In one example, the ICAM-1 is soluble ICAM-1 (sICAM-1).

In one example, the P-selectin is soluble P-selectin (sP-selectin).

In one example, the compound that inhibits G-CSF signaling is administered in an amount sufficient to reduce or prevent an increase in the amount of nucleosomes and/or elastase-α-antitrypsin complexes.

In one example, the compound that inhibits G-CSF signaling is administered in an amount sufficient to reduce or prevent an increase in the level of expression of one or more of the following:
soluble CD177 (sCD177);
CD62L;
calprotectin;
tumor necrosis factor alpha (TNFα);
interleukin 2 (IL-2);
IL-3;
IL-6;
IL-8;
IL-10;
C-reactive protein high sensitivity (hsCRP);
peptidyl Arginine Deiminase 4 (PADI4);
Elastase, Neutrophil Expressed (ELANE); and
myeloperoxidase (MPO).

In one example, administration of the compound that inhibits G-CSF signaling reduces, or prevents an increase in the level of expression of one or more genes in the subject's lung and/or liver selected from the group consisting of E-selectin, vascular cell adhesion molecule 1 (VCAM-1), intercellular adhesion molecule 1 (ICAM-1), P-selectin, soluble CD177 (sCD177), CD62L, calprotectin, tumor necrosis factor alpha (TNFα), interleukin 2 (IL-2), IL-3, IL-6, IL-8, IL-10, C-reactive protein high sensitivity (hsCRP), peptidyl Arginine Deiminase 4 (PADI4), Elastase, Neutrophil Expressed (ELANE), myeloperoxidase (MPO)

and combinations thereof. In one example, administration of the compound that inhibits G-CSF signaling reduces, or prevents an increase in the level of expression of one or more genes in the subject's lung and/or liver selected from the group consisting of E-selectin, vascular cell adhesion molecule 1 (VCAM-1), intercellular adhesion molecule 1 (ICAM-1), P-selectin and combinations thereof. For example, administration of the compound that inhibits G-CSF signaling reduces, or prevents an increase in the level of expression of E-selectin, vascular cell adhesion molecule 1 (VCAM-1) and intercellular adhesion molecule 1 (ICAM-1), P-selectin in the subject's liver. In another example, administration of the compound that inhibits G-CSF signaling reduces, or prevents an increase in the level of expression of P-selectin in the subject's lung.

In one example, the compound that inhibits G-CSF signaling is administered in an amount sufficient to increase or upregulate expression of heme-oxygenase-1 (HO-1). For example, the compound that inhibits G-CSF signaling is administered in an amount sufficient to increase or upregulate expression of heme-oxygenase-1 (HO-1) on endothelial cells.

In one example, the compound that inhibits G-CSF signaling is administered in an amount sufficient to increase or upregulate expression of NF-E2-related factor 2 (NRF2) on endothelial cells.

In one example, administration of the compound that inhibits G-CSF signaling increases, or upregulates the level of expression of heme-oxygenase-1 (HO-1) and/or NF-E2-related factor 2 (NRF2) in the subject's lung and/or liver. For example, administration of the compound that inhibits G-CSF signaling increases, or upregulates the level of expression of heme-oxygenase-1 (HO-1) in the subject's lung and/or liver. In one example, administration of the compound that inhibits G-CSF signaling increases, or upregulates the level of expression of heme-oxygenase-1 (HO-1) in the subject's lung. In another example, administration of the compound that inhibits G-CSF signaling increases, or upregulates the level of expression of heme-oxygenase-1 (HO-1) in the subject's liver. In a further example, administration of the compound that inhibits G-CSF signaling increases, or upregulates the level of expression of NF-E2-related factor 2 (NRF2) in the subject's lung and/or liver. In one example, administration of the compound that inhibits G-CSF signaling increases, or upregulates the level of expression of NF-E2-related factor 2 (NRF2) in the subject's lung. In a further example, administration of the compound that inhibits G-CSF signaling increases, or upregulates the level of expression of NF-E2-related factor 2 (NRF2) in the subject's liver.

Methods for measuring the expression level of a gene will be known in the art. For example, expression level of a gene can be measured by quantifying the amount of mRNA, e.g., by northern blot or by quantitative reverse transcription PCR (qRT-PCR) as described in Riedy et al Biotechniques (1995), wherein the level of gene expression is normalised against a housekeeping gene (e.g., GAPDH). In one example, the level of gene expression is normalised against a housekeeping gene. For example, the level of gene expression is normalised against GAPDH. In another example, the level of gene expression is normalised against HMBS. Alternatively, or in addition, expression level of a gene can be measured by quantifying the level of protein encoded by the gene, e.g., by enzyme-linked immunosorbent assay (ELISA), fluorescence linked immunosorbent assay (FLISA), immunofluorescence or immunoblotting (see Sambrook et al., Molecular Cloning: A Laboratory Manual, Cold Spring Harbor Laboratory Press (1989)).

In one example, the levels of the above genes are reduced, or prevented from increasing, or increased or upregulated in a sample obtained from the subject. For example, the sample is a tissue sample. For example, the tissue is a lung tissue sample, such as a lung biopsy sample, or a liver tissue sample, such as a liver biopsy sample.

In one example, the compound that inhibits G-CSF signaling binds to G-CSF or to G-CSF receptor (G-CSFR). In one example, the compound that inhibits G-CSF signaling binds to G-CSF. In one example, the compound that inhibits G-CSF signaling binds to G-CSF receptor (G-CSFR).

In one example, the compound that inhibits G-CSF signaling is a protein.

In one example, the compound that inhibits G-CSF signaling is a protein comprising an antibody variable region that binds to or specifically binds to G-CSFR and neutralizes G-CSF signaling. Reference herein to a protein or antibody that "binds to" G-CSFR provides literal support for a protein or antibody that "binds specifically to" G-CSFR.

In one example, the compound that inhibits G-CSF signaling is a protein comprising an antibody variable region that binds to or specifically binds to G-CSF and neutralizes G-CSF signaling. Reference herein to a protein or antibody that "binds to" G-CSF provides literal support for a protein or antibody that "binds specifically to" G-CSF.

In one example, the protein comprises a heavy chain variable region ($V_H$). In one example, the protein comprises a light chain variable region ($V_L$). In one example, the protein comprises a $V_H$ and a $V_L$. In one example, the protein comprises a $V_H$ and a $V_L$. In one example, the $V_H$ and a $V_L$ are in the same polypeptide chain. In another example, the $V_H$ and a $V_L$ are in separate polypeptide chains.

In one example, a protein described herein comprises at least a heavy chain variable region ($V_H$) and a light chain variable region ($V_L$), wherein the $V_H$ and $V_L$ bind to form a Fv comprising an antigen binding domain. In one examples, the compound that inhibits G-CSF signaling is a protein comprising a Fv. The skilled artisan will understand that the antigen binding domain comprises the binding site of the antibody.

In one example, the protein is selected from the group consisting of:
(i) a single chain Fv fragment (scFv);
(ii) a dimeric scFv (di-scFv);
(iii) a diabody;
(iv) a triabody;
(v) a tetrabody;
(vi) a Fab;
(vii) a F(ab')$_2$;
(viii) a Fv;
(ix) one of (i) to (viii) linked to a constant region of an antibody, Fc or a heavy chain constant domain ($C_H$) 2 and/or $C_H$3;
(x) one of (i) to (viii) linked to albumin, functional fragments or variants thereof or a protein (e.g., antibody or antigen binding fragment thereof) that binds to albumin; and
(xi) an antibody.

The foregoing proteins (described in the previous three lists) can also be referred to as antigen binding domains of antibodies.

In one example, the protein is an antibody. In one example, the antibody is a naked antibody. Exemplary antibodies are described in WO2012171057, WO2018145206 and WO2022055334, all of which are incorporated herein by reference.

In one example, the protein is an antibody which binds to hG-CSFR expressed on the surface of a cell at an affinity of at least about 5 nM. In one example, the protein is an antibody which binds to hG-CSFR expressed on the surface of a cell at an affinity of at least about 4 nM. In one example, the protein is an antibody which binds to hG-CSFR expressed on the surface of a cell at an affinity of at least about 3 nM. In one example, the protein is an antibody which binds to hG-CSFR expressed on the surface of a cell at an affinity of at least about 2 nM. In one example, the protein is an antibody which binds to hG-CSFR expressed on the surface of a cell at an affinity of at least about 1 nM.

In one example, the protein is an antibody which inhibits G-CSF-induced proliferation of a BaF3 cell expressing hG-CSFR with an IC50 of at least about 5 nM. In one example, the protein is an antibody which inhibits G-CSF-induced proliferation of a BaF3 cell expressing hG-CSFR with an IC50 of at least about 4 nM. In one example, the protein is an antibody which inhibits G-CSF-induced proliferation of a BaF3 cell expressing hG-CSFR with an IC50 of at least about 3 nM. In one example, the protein is an antibody which inhibits G-CSF-induced proliferation of a BaF3 cell expressing hG-CSFR with an IC50 of at least about 2 nM. In one example, the protein is an antibody which inhibits G-CSF-induced proliferation of a BaF3 cell expressing hG-CSFR with an IC50 of at least about 1 nM. In one example, the protein is an antibody which inhibits G-CSF-induced proliferation of a BaF3 cell expressing hG-CSFR with an IC50 of at least about 0.5 nM.

In one example, the protein is chimeric, de-immunized, humanized, human or primatized.

In one example, the protein or antibody is human.

In one example, the protein comprises an antibody variable region that competitively inhibits the binding of antibody C1.2G comprising a heavy chain variable region ($V_H$) Comprising a sequence set forth in SEQ ID NO: 4 and a light chain variable region ($V_L$) comprising a sequence set forth in SEQ ID NO: 5 to G-CSFR.

In one example, the protein binds to an epitope comprising residues within one or two or three or four regions selected from 111-115, 170-176, 218-234 and/or 286-300 of SEQ ID NO: 1. For example, the protein binds to an epitope comprising residues within one region selected from 111-115, 170-176, 218-234 and/or 286-300 of SEQ ID NO: 1. For example, the protein binds to an epitope comprising residues within two regions selected from 111-115, 170-176, 218-234 and/or 286-300 of SEQ ID NO: 1. For example, the protein binds to an epitope comprising residues within three regions selected from 111-115, 170-176, 218-234 and/or 286-300 of SEQ ID NO: 1. For example, the protein binds to an epitope comprising residues within four regions selected from 111-115, 170-176, 218-234 and/or 286-300 of SEQ ID NO: 1.

In one example, the protein is an antibody comprising a heavy chain variable region ($V_H$) comprising an amino acid sequence set forth in SEQ ID NO: 4 and a light chain variable region ($V_L$) comprising an amino acid sequence set forth in SEQ ID NO: 5.

In one example, the protein is an antibody comprising a $V_H$ Comprising an amino acid sequence set forth in SEQ ID NO: 2 and a $V_L$ comprising an amino acid sequence set forth in SEQ ID NO: 3.

In one example, the protein is an antibody comprising a $V_H$ comprising three CDRs of a $V_H$ comprising an amino acid sequence set forth in SEQ ID NO: 4 and a $V_L$ comprising three CDRs of a $V_L$ comprising an amino acid sequence set forth in SEQ ID NO: 5.

In one example, the protein is an antibody comprising a $V_H$ comprising three CDRs of a $V_H$ comprising an amino acid sequence set forth in SEQ ID NO: 2 and a $V_L$ comprising three CDRs of a $V_L$ comprising an amino acid sequence set forth in SEQ ID NO: 3.

In one example, the CDRs are positioned according to the numbering system of Kabat.

In one example, the compound that inhibits G-CSF signaling is a protein comprising an antigen binding domain of an antibody, wherein the antigen binding domain comprises a $V_H$ and a $V_L$, wherein:
(i) the $V_H$ comprises:
 a. a CDR1 comprising a sequence set forth between amino acids 31-35 of SEQ ID NO: 2;
 b. a CDR2 comprising a sequence set forth between amino acids 50-65 of SEQ ID NO: 2; and
 c. a CDR3 comprising a sequence set forth between amino acids 99-107 of SEQ ID NO: 2; and
(ii) the $V_L$ comprises:
 a. a CDR1 comprising a sequence set forth between amino acids 24-34 of SEQ ID NO: 3;
 b. a CDR2 comprising a sequence set forth between amino acids 51-56 of SEQ ID NO: 3; and
 c. a CDR3 comprising a sequence set forth between amino acids 89-97 of SEQ ID NO: 3.

In one example, the compound that inhibits G-CSF signaling is a protein comprising an antigen binding domain of an antibody, wherein the antigen binding domain comprises a $V_H$ and a $V_L$, wherein:
(i) the $V_H$ comprises:
 a. a CDR1 comprising a sequence set forth between amino acids 31-35 of SEQ ID NO: 4;
 b. a CDR2 comprising a sequence set forth between amino acids 50-65 of SEQ ID NO: 4; and
 c. a CDR3 comprising a sequence set forth between amino acids 99-107 of SEQ ID NO: 4; and
(ii) the $V_L$ comprises:
 a. a CDR1 comprising a sequence set forth between amino acids 24-34 of SEQ ID NO: 5;
 b. a CDR2 comprising a sequence set forth between amino acids 51-56 of SEQ ID NO: 5; and
 c. a CDR3 comprising a sequence set forth between amino acids 89-97 of SEQ ID NO: 5.

In one example, the compound that inhibits G-CSF signaling is a protein comprising an antigen binding domain of an antibody, wherein the antigen binding domain comprises a $V_H$ and a $V_L$, wherein:
(i) the $V_H$ comprises:
 a. a CDR1 comprising a sequence set forth in SEQ ID NO: 6,
 b. a CDR2 comprising a sequence set forth in SEQ ID NO: 7, and
 c. a CDR3 comprising a sequence set forth in LGELGX$_1$X$_2$X$_3$X$_4$(SEQ ID NO: 12), wherein:
  X$_1$ is selected from the group consisting of tryptophan, glutamine, methionine, serine, phenylalanine, glutamic acid and histidine;
  X$_2$ is an amino acid selected from the group consisting of phenylalanine, tyrosine, methionine, serine, glycine and isoleucine;
  X$_3$ is an amino acid selected from the group consisting of aspartic acid, methionine, glutamine, serine, leucine, valine, arginine and histidine; and
  X$_4$ is any amino acid or an amino acid selected from the group consisting of proline, glutamic acid, alanine, leucine, phenylalanine, tyrosine, threonine, asparagine, aspartic acid, serine, glycine, arginine, and lysine; and (ii) a light chain variable region (VL) comprising:
  a. a CDR1 comprising a sequence set forth in SEQ ID NO: 9,
  b. a CDR2 comprising a sequence set forth in SEQ ID NO: 10, and
  c. a CDR3 comprising a sequence set forth in $X_1X_2X_3X_4X_5X_6X_7X_8X_9$, (SEQ ID NO: 13) wherein:
    $X_1$ is an amino acid selected from the group consisting of glutamine, glutamic acid, histidine, alanine and serine;
    $X_2$ is an amino acid selected from the group consisting of glutamine, valine, phenylalanine, asparagine and glutamic acid;
    $X_3$ is an amino acid selected from the group consisting of serine and glycine;
    $X_4$ is an amino acid selected from the group consisting of tryptophan, methionine, phenylalanine, tyrosine, isoleucine and leucine;
    $X_5$ is an amino acid selected from the group consisting of glutamic acid, methionine, glutamine, tryptophan, serine, valine, asparagine, glycine, alanine, arginine, histidine, tyrosine, lysine and threonine;
    $X_6$ is an amino acid selected from the group consisting of tyrosine, methionine, isoleucine and threonine;
    $X_7$ is an amino acid selected from the group consisting of proline, alanine, histidine, glycine and lysine;
    $X_8$ is an amino acid selected from the group consisting of leucine, glutamine, methionine, alanine, phenylalanine, isoleucine, lysine, histidine and glycine; and
    $X_9$ is an amino acid selected from the group consisting of threonine, phenylalanine, tyrosine, methionine, lysine, serine, histidine, proline, tryptophan, isoleucine, glutamine, glycine and valine.

In one example, the compound that inhibits G-CSF signaling is a protein comprising an antigen binding domain of an antibody, wherein the antigen binding domain comprises a $V_H$ and a $V_L$, wherein:
(i) the $V_H$ comprises:
  a. a CDR1 comprising a sequence set forth in SEQ ID NO: 6;
  b. a CDR2 comprising a sequence set forth in SEQ ID NO: 7; and
  c. a CDR3 comprising a sequence set forth in SEQ ID NO: 8; and
(ii) the $V_L$ comprises:
  a. a CDR1 comprising a sequence set forth in SEQ ID NO: 9;
  b. a CDR2 comprising a sequence set forth in SEQ ID NO: 10; and
  c. a CDR3 comprising a sequence set forth in SEQ ID NO: 11.

In one example, the compound that inhibits G-CSF signaling is a protein comprising an antigen binding domain of an antibody, wherein the antigen binding domain comprises a $V_H$ and a $V_L$, wherein:
(A) (i) the $V_H$ comprises a CDR1 comprising a sequence set forth between amino acids 31-35 of SEQ ID NO: 2; a CDR2 comprising a sequence set forth between amino acids 50-65 of SEQ ID NO: 2; and a CDR3 comprising a sequence set forth between amino acids 99-107 of SEQ ID NO: 2; and
  (ii) the $V_L$ comprises a CDR1 comprising a sequence set forth between amino acids 24-34 of SEQ ID NO: 3; a CDR2 comprising a sequence set forth between amino acids 51-56 of SEQ ID NO: 3; and a CDR3 comprising a sequence set forth between amino acids 89-97 of SEQ ID NO: 3; or
(B) (i) the $V_H$ comprises a CDR1 comprising a sequence set forth between amino acids 31-35 of SEQ ID NO: 4; a CDR2 comprising a sequence set forth between amino acids 50-65 of SEQ ID NO: 4; and a CDR3 comprising a sequence set forth between amino acids 99-107 of SEQ ID NO: 4; and
  (ii) the $V_L$ comprises a CDR1 comprising a sequence set forth between amino acids 24-34 of SEQ ID NO: 5; a CDR2 comprising a sequence set forth between amino acids 51-56 of SEQ ID NO: 5; and a CDR3 comprising a sequence set forth between amino acids 89-97 of SEQ ID NO: 5; or
(C) (i) the $V_H$ comprises a CDR1 comprising a sequence set forth in SEQ ID NO: 6; a CDR2 comprising a sequence set forth in SEQ ID NO: 7; and a CDR3 comprising a sequence set forth in SEQ ID NO: 8; and
  (ii) the $V_L$ comprises a CDR1 comprising a sequence set forth in SEQ ID NO: 9; a CDR2 comprising a sequence set forth in SEQ ID NO: 10; and CDR3 comprising a sequence set forth in SEQ ID NO: 11.

In one example, the protein or antibody as described herein comprises a human constant region, e.g., an IgG constant region, such as an $IgG_1$, $IgG_2$, $IgG_3$ or $IgG_4$ constant region or mixtures thereof. In the case of an antibody or protein comprising a $V_H$ and a $V_L$, the $V_H$ can be linked to a heavy chain constant region and the $V_L$ can be linked to a light chain constant region.

In one example, a protein or antibody as described herein comprises a constant region of an $IgG_4$ antibody or a stabilized constant region of an $IgG_4$ antibody. In one example, the protein or antibody comprises an $IgG_4$ constant region with a proline at position 241 (according to the numbering system of Kabat (Kabat et al., Sequences of Proteins of Immunological Interest Washington DC United States Department of Health and Human Services, 1987 and/or 1991)).

The C-terminal lysine of the heavy chain constant region of a whole antibody (or a protein or antibody comprising a constant region or a $C_H3$) of the disclosure may be removed, for example, during production or purification of the antibody or protein, or by recombinantly engineering the nucleic acid encoding a heavy chain of the antibody. Accordingly, whole antibodies may comprise populations with all C-terminal lysine residues removed, populations with no C-terminal lysine residues removed, and/or populations having a mixture of protein with and without the C-terminal lysine residue. In some examples, the populations may additionally comprise protein in which the C-terminal lysine residue is removed in one of the heavy chain constant regions. Similarly, a composition of whole antibodies may comprise the same or a similar mix of antibody populations with or without the C-terminal lysine residue.

In one example a protein or antibody as described herein or a composition of a protein or antibody as described herein, comprises a heavy chain constant region, including a stabilized heavy chain constant region, comprising a mixture of sequences fully or partially with or without the C-terminal lysine residue.

In one example, an antibody of the disclosure comprises a V$_H$ disclosed herein linked or fused to an IgG4 constant region or stabilized IgG4 constant region (e.g., as discussed above) and the V$_L$ is linked to or fused to a kappa light chain constant region.

In one example, the protein is an antibody comprising:
(i) a heavy chain comprising an amino acid sequence set forth in SEQ ID NO: 14 or 18 and a light chain comprising an amino acid sequence set forth in SEQ ID NO: 15; or
(ii) one heavy chain comprising an amino acid sequence set forth in SEQ ID NO: 14 and one heavy chain comprising an amino acid sequence set forth in SEQ ID NO: 18 and two light chains comprising an amino acid sequence set forth in SEQ ID NO: 15.

In one example, the protein is an antibody comprising a heavy chain comprising an amino acid sequence set forth in SEQ ID NO: 14 or 18 and a light chain comprising an amino acid sequence set forth in SEQ ID NO: 15. For example, the protein is an antibody comprising a heavy chain comprising an amino acid sequence set forth in SEQ ID NO: 14 and a light chain comprising an amino acid sequence set forth in SEQ ID NO: 15. In another example, the protein is an antibody comprising a heavy chain comprising an amino acid sequence set forth in SEQ ID NO: 18 and a light chain comprising an amino acid sequence set forth in SEQ ID NO: 15.

In one example, the protein is an antibody comprising one heavy chain comprising an amino acid sequence set forth in SEQ ID NO: 14 and one heavy chain comprising an amino acid sequence set forth in SEQ ID NO: 18 and two light chains comprising an amino acid sequence set forth in SEQ ID NO: 15.

In one example, the protein or antibody is any form of the protein or antibody encoded by a nucleic acid encoding any of the foregoing proteins or antibodies.

In one example, the compound that inhibits G-CSF signaling is a protein comprising an antibody variable region, wherein the antibody variable region comprises a V$_H$ expressed by a nucleic acid encoding an amino acid of SEQ ID NO: 4 and a V$_L$ expressed by a nucleic acid encoding an amino acid of SEQ ID NO: 5.

In one example, the compound that inhibits G-CSF signaling is a protein comprising an antibody variable region, wherein the antibody variable region comprises a V$_H$ expressed by a nucleic acid encoding an amino acid of SEQ ID NO: 2 and a V$_L$ expressed by a nucleic acid encoding an amino acid of SEQ ID NO: 3.

In one example, the compound that inhibits G-CSF signaling is a protein comprising an antibody variable region, wherein the antibody variable region comprises:
(i) a V$_H$ comprising:
  (a) a CDR1 expressed by a nucleic acid encoding an amino acid of SEQ ID NO: 6;
  (b) a CDR2 expressed by a nucleic acid encoding an amino acid of SEQ ID NO: 7; and
  (c) a CDR3 expressed by a nucleic acid encoding an amino acid of SEQ ID NO: 8; and
(ii) a V$_L$ comprising:
  (a) a CDR1 expressed by a nucleic acid encoding an amino acid of SEQ ID NO: 9;
  (b) a CDR2 expressed by a nucleic acid encoding an amino acid of SEQ ID NO: 10; and
  (c) a CDR3 expressed by a nucleic acid encoding an amino acid of SEQ ID NO: 11.

In one example, the compound that inhibits G-CSF signaling is a protein comprising an antibody variable region, wherein the antibody variable region comprises:
(i) a V$_H$ comprising:
  (a) a CDR1 comprising a sequence encoded by a nucleic acid comprising SEQ ID NO: 23;
  (b) a CDR2 comprising a sequence encoded by a nucleic acid comprising SEQ ID NO: 24; and
  (c) a CDR3 comprising a sequence encoded by a nucleic acid comprising SEQ ID NO: 25; and
(ii) a V$_L$ comprising:
  (a) a CDR1 comprising a sequence encoded by a nucleic acid comprising SEQ ID NO: 26;
  (b) a CDR2 comprising a sequence encoded by a nucleic acid comprising SEQ ID NO: 27; and
  (c) a CDR3 comprising a sequence encoded by a nucleic acid comprising SEQ ID NO: 28.

In one example, the protein or antibody comprises:
(i) a V$_H$ comprising:
  (a) a CDR1 comprising a sequence encoded by a nucleic acid comprising SEQ ID NO: 23;
  (b) a CDR2 comprising a sequence encoded by a nucleic acid comprising SEQ ID NO: 24; and
  (c) a CDR3 comprising a sequence encoded by a nucleic acid comprising SEQ ID NO: 25; and
(ii) a V$_L$ comprising:
  (a) a CDR1 comprising a sequence encoded by a nucleic acid comprising SEQ ID NO: 26;
  (b) a CDR2 comprising a sequence encoded by a nucleic acid comprising SEQ ID NO: 27; and
  (c) a CDR3 comprising a sequence encoded by a nucleic acid comprising SEQ ID NO: 28.

In one example, the compound that inhibits G-CSF signaling is a protein comprising an antibody variable region, wherein the antibody variable region comprises a V$_H$ comprising three CDRs of a V$_H$ comprising a sequence encoded by a nucleic acid comprising SEQ ID NO: 21 and a V$_L$ comprising three CDRs of a V$_L$ comprising a sequence encoded by a nucleic acid comprising SEQ ID NO: 22.

In one example, the compound that inhibits G-CSF signaling is a protein comprising an antibody variable region, wherein the antibody variable region comprises a V$_H$ comprising a sequence encoded by a nucleic acid comprising SEQ ID NO: 21; and a V$_L$ comprising a sequence encoded by a nucleic acid comprising SEQ ID NO: 22.

In one example, the compound that inhibits G-CSF signaling is a protein comprising an antibody variable region, wherein the antibody variable region comprises a heavy chain comprising a sequence encoded by a nucleic acid comprising SEQ ID NO: 19; and a light chain comprising a sequence encoded by a nucleic acid comprising SEQ ID NO: 20.

The functional characteristics of a compound that inhibits G-CSF signaling of the disclosure will be taken to apply mutatis mutandis to an antibody of the disclosure.

In one example, the compound that inhibits G-CSF signaling is administered in combination with a standard of care therapy.

In one example, the standard of care therapy may be a standard of care therapy for the complication associated with sickle cell disease, or it may be a standard of care therapy for the sickle cell disease itself.

In one example, the standard of care therapy comprises one or more or all of the following:
(a) blood transfusion;
(b) stem cell or bone marrow transplantation;
(c) hemoglobin S (HbS) polymerization inhibitor;

(d) crizanlizumab;
(e) antimetabolite;
(f) L-glutamine;
(g) analgesic; and
(h) antibiotics.

In one example, the standard of care therapy comprises a blood transfusion. For example, the blood transfusion is a red blood cell transfusion.

In one example, the standard of care therapy comprises a stem cell or bone marrow transplantation.

In one example, the standard of care therapy comprises a hemoglobin S (HbS) polymerization inhibitor. For example, the inhibitor is voxelotor. Exemplary voxelotor will be apparent to the skilled person and include for example, Oxbryta®.

In one example, the standard of care therapy comprises crizanlizumab. For example, the crizanlizumab is crizanlizumab-tmca. Exemplary crizanlizumab-tmca will be apparent to the skilled person and include for example, Adakveo®.

In one example, the standard of care therapy comprises an antimetabolite. For example, the antimetabolite is hydroxyurea or hydroxycarbamide. In one example, the antimetabolite is hydroxyurea.

In one example, the standard of care therapy comprises L-glutamine. For example, the L-glutamine is a L-glutamine oral power. Exemplary L-glutamine will be apparent to the skilled person and include for example, Endari®.

In one example, the standard of care therapy comprises analgesics. Analgesics include, but are not limited to, non-steroidal anti-inflammatory drugs (NSAIDS) and opioids (narcotics). Opioids include, but are not limited to, dextropropoxyphene, codeine, tramadol, tapentadol, anileridine, alphaprodine, pethidine, hydocodone, morphine, pethidine oxycodone, methadone, diamorphine, hydromorphone, oxymorphone, levorphanol, 7-hydroxymitragynine, buprenorphine, fentanyl, sufentanil, bromadol, etorphine, dihydroetorphine, and carfentanil. NSAIDS include, but are not limited to, aspirin, acetaminophen, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, and firocoxib.

In one example, the standard of care therapy comprises antibiotics. Antibiotics include, but are not limited to, penicillin, amoxicillin, amoxicillin-clavulanic acid, cephalosporin, ampicillin, vanomycin, roxithromycin, azithromycin, rifaximin, clarithromycin and cefixime.

The present disclosure also provides a kit comprising a compound that inhibits G-CSF signaling packaged with instructions for use in treating or preventing or delaying progression or reducing or inhibiting or hindering development of a complication associated with sickle cell disease in a subject suffering from sickle cell disease.

In one example, the kit optionally comprises an additional therapy for administration in use in combination with a compound of the disclosure.

In one example, the subject is a human. In one example, the subject is an adult, for example over 18 years of age. In one example, the subject is a child, for example less than 18 years of age.

KEY TO SEQUENCE LISTING

Figure 1:
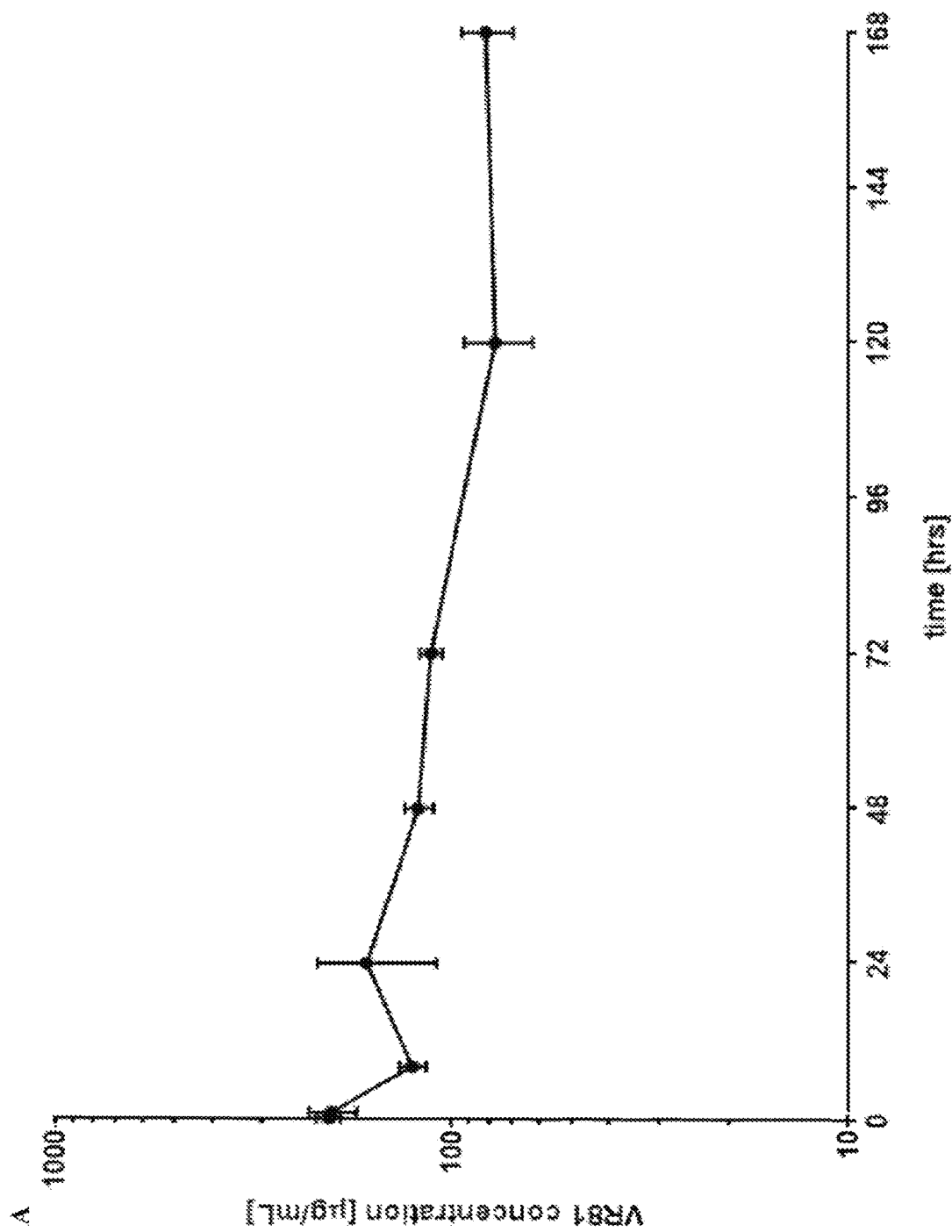
FIG. 1 is a graphical representation showing (A) pharmacokinetics of VR81 in Townes sickle mice at 30 mg/kg, (B) receptor occupancy and (C) inhibition of receptor activity by phosphorylation of STAT3.
Figure 1:
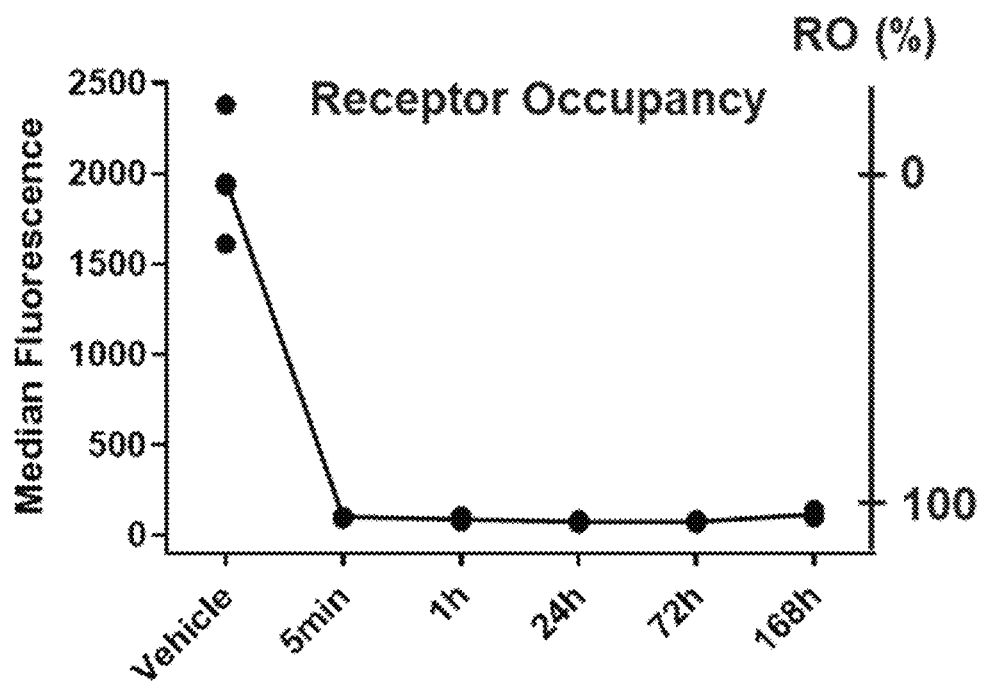
Figure 1:
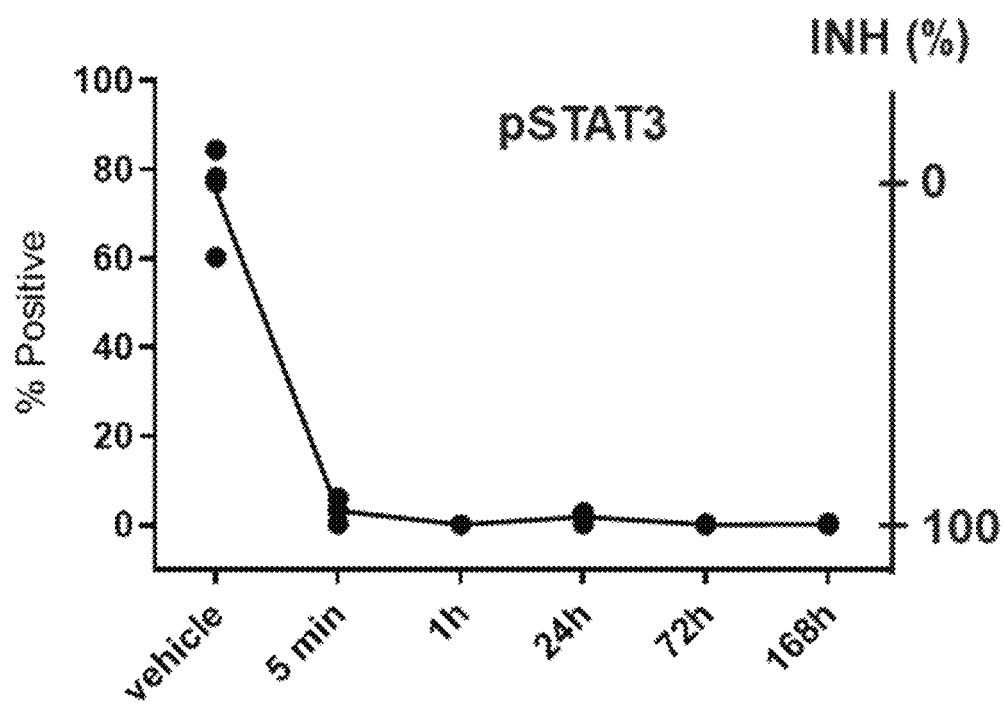

SEQ ID NO: 1—amino acids 25-335 of *Homo sapiens* G-CSFR (hG-CSFR) with a C-terminal polyhistidine tag
SEQ ID NO: 2—$V_H$ of C1.2
SEQ ID NO: 3—$V_L$ of C1.2
SEQ ID NO: 4—$V_H$ of C1.2G
SEQ ID NO: 5—$V_L$ of C1.2G
SEQ ID NO: 6—HCDR1 of C1.2
SEQ ID NO: 7—HCDR2 of C1.2
SEQ ID NO: 8—HCDR3 of C1.2
SEQ ID NO: 9—LCDR1 of C1.2
SEQ ID NO: 10—LCDR2 of C1.2
SEQ ID NO: 11—LCDR3 of C1.2
SEQ ID NO: 12—consensus sequence of HCDR3 of C1.2
SEQ ID NO: 13—consensus sequence of LCDR3 of C1.2
SEQ ID NO: 14—Heavy chain of C1.2G with stabilized IgG4 constant region
SEQ ID NO: 15—Light chain of C1.2G with kappa constant region
SEQ ID NO: 16—sequence of exemplary h-G-CSFR
SEQ ID NO: 17—polypeptide comprising Ig and CRH domains of *Macaca fascicularis* G-CSFR (cynoG-CSFR) with a C-terminal polyhistidine tag
SEQ ID NO: 18—Heavy chain of C1.2G with stabilized IgG4 constant region and lacking C-terminal lysine
SEQ ID NO: 19: nucleotide sequence of heavy chain of C1.2G
SEQ ID NO: 20: nucleotide sequence of light chain of C1.2G
SEQ ID NO: 21: nucleotide sequence of $V_H$ of C1.2G
SEQ ID NO: 22: nucleotide sequence of $V_L$ of C1.2G
SEQ ID NO: 23: nucleotide sequence of HCDR1 of C1.2G
SEQ ID NO: 24: nucleotide sequence of HCDR2 of C1.2G
SEQ ID NO: 25: nucleotide sequence of HCDR3 of C1.2G
SEQ ID NO: 26: nucleotide sequence of LCDR1 of C1.2G
SEQ ID NO: 27: nucleotide sequence of LCDR2 of C1.2G
SEQ ID NO: 28: nucleotide sequence of LCDR3 of C1.2G

DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise. Stated another way, any specific example of the present disclosure may be combined with any other specific example of the disclosure (except where mutually exclusive).

Any example of the present disclosure disclosing a specific feature or group of features or method or method steps will be taken to provide explicit support for disclaiming the specific feature or group of features or method or method steps.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, antibodies and fragments thereof herein may be further clarified by the discussion in Kabat Sequences of Proteins of Immunological Interest, National Institutes of Health, Bethesda, Md., 1987 and 1991.

The term "EU numbering system of Kabat" will be understood to mean the numbering of an antibody heavy chain is according to the EU index as taught in Kabat et al., 1991, Sequences of Proteins of Immunological Interest, 5th Ed., United States Public Health Service, National Institutes of Health, Bethesda. The EU index is based on the residue numbering of the human IgG1 EU antibody.

Any discussion of a protein or antibody herein will be understood to include any variants of the protein or antibody produced during manufacturing and/or storage. For example, during manufacturing or storage an antibody can be deamidated (e.g., at an asparagine or a glutamine residue) and/or have misincorporated amino acid residues (e.g., a serine misincorporated in place of an asparagine residue) and/or have altered glycosylation and/or have a glutamine residue converted to pyroglutamine and/or have a N-terminal or C-terminal residue removed or "clipped" and/or have part or all of a signal sequence incompletely processed and, as a consequence, remain at the terminus of the antibody. It is understood that a composition comprising a particular amino acid sequence may be a heterogeneous mixture of the stated or encoded sequence and/or variants of that stated or encoded sequence.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

A "compound", as contemplated by the present disclosure, can take any of a variety of forms including natural compounds, chemical small molecule compounds or biological compounds or macromolecules. Exemplary compounds include an antibody or a protein comprising an antigen binding fragment of an antibody, a nucleic acid, a polypeptide, a peptide, and a small molecule.

Reference herein to "granulocyte colony-stimulating factor" (G-CSF) includes native forms of G-CSF, mutant forms thereof, e.g., filgrastim and pegylated forms of G-CSF or filgrastim. This term also encompasses mutant forms of G-CSF retaining activity to bind to G-CSFR (e.g., human G-CSFR) and induce signaling.

G-CSF is a major regulator of granulocyte production. G-CSF is produced by bone marrow stromal cells, endothelial cells, macrophages, and fibroblasts, and production is induced by inflammatory stimuli. G-CSF acts through the G-CSF receptor (G-CSFR), which is expressed on early myeloid progenitors, mature neutrophils, monocytes/macrophages, T and B lymphocytes and endothelial cells.

For the purposes of nomenclature only and not limitation, an exemplary sequence of a human G-CSFR is set out in NCBI Reference Sequence: NP_000751.1 (and set out in SEQ ID NO: 16). The sequence of G-CSFR from other species can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)) Reference to human G-CSFR may be abbreviated to hG-CSFR and reference to cynomolgus monkey G-CSFR may be abbreviated to cynoG-CSFR. Reference to soluble G-CSFR refers to polypeptides comprising the ligand binding region of G-CSFR. The Ig and CRH domains of the G-CSFR are involved in ligand binding and receptor dimerization (Layton et al., J. Biol Chem., 272: 29735-29741, 1997 and Fukunaga et al, EMBO J. 10: 2855-2865, 1991). Soluble forms of G-CSFR comprising these portions of the receptor have been used in various studies of the receptor and mutation of the free cysteines at positions 78, 163, and 228 of the receptor assists in expression and isolation of the soluble receptor polypeptide (Mine et al., Biochem., 43: 2458-2464 2004) without affecting ligand binding.

As used herein, the term "G-CSF signaling" refers to biological activities mediated via the G-CSF receptor (G-CSFR). It will be understood that reference to inhibiting G-CSF signaling encompasses inhibition of G-CSF activity, including downstream pathways, mediated via the receptor. It will be apparent to the skilled person from the disclosure herein that the compound, for example, binds the G-CSF receptor and displaces or hinders the binding of G-CSF to the receptor. For example, the G-CSF signaling is G-CSF receptor mediated signaling.

As used herein, reference to the term "G-CSF activity" refers to G-CSF biological activity, including downstream pathways mediated by G-CSF signaling. It will be understood that reference to inhibiting G-CSF activity encompasses all functional states and characteristics whereby G-CSF biological activity (including, but not limited to, its ability to treat or prevent or delaying progression or reduce or inhibit or hinder development of a complication associated with sickle cell disease), or the consequences of the biological activity, are substantially nullified, decreased, or neutralized. It will be apparent to the skilled person that inhibition of G-CSF activity need not necessarily occur by binding of the compound to the G-CSF receptor but may include, for example, binding of a compound to G-CSF and/or another molecule that binds to and signals via the G-CSFR.

As used herein, the terms "preventing", "prevent" or "prevention" include administering a compound of the disclosure to thereby stop or hinder, at least partially, the development of at least one symptom of a condition. This term also encompasses treatment of a subject in remission to prevent or hinder relapse.

As used herein, the terms "treating", "treat" or "treatment" include administering a compound described herein to thereby reduce or eliminate at least one symptom of a specified disease or condition.

As used herein, the term "delaying progression of" shall be understood to include administering a compound described herein to thereby reduce or hinder or slow the progression of at least one specified disease or condition, or associated symptom thereof.

As used herein, the phrase "reduce" or "reducing" shall be understood to include administering a compound described herein to make smaller or less in amount, degree or size at least one specified disease or condition, or symptom thereof.

As used herein, the phrase "inhibit" or "inhibiting" shall be understood to include administering a compound described herein to eliminate or stop, at least partially the development of at least one specified disease or condition, or symptom thereof.

As used herein, the phrase "hinder" or "hindering" shall be understood to include administrating a compound described herein to limit or impede or hamper, at least partially the development of at least one specified disease or condition, or symptom thereof.

As used herein, the term "subject" shall be taken to mean any animal including humans, for example a mammal. Exemplary subjects include but are not limited to humans and non-human primates. For example, the subject is a human.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

As used herein, the term "nucleotide sequence" or "nucleic acid sequence" will be understood to mean a series of contiguous nucleotides (or bases) covalently linked to a phosphodiester backbone.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

As used herein, the term "antigen binding site" shall be taken to mean a structure formed by a protein that is capable of binding or specifically binding to an antigen. The antigen binding site need not be a series of contiguous amino acids, or even amino acids in a single polypeptide chain. For example, in a Fv produced from two different polypeptide chains the antigen binding site is made up of a series of amino acids of a $V_L$ and a $V_H$ that interact with the antigen and that are generally, however not always in the one or more of the CDRs in each variable region. In some examples, an antigen binding site is a $V_H$ or a $V_L$ or a Fv.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are necessary for antigen binding. Each variable region typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Plükthun *J. Mol. Biol.*, 309: 657-670, 2001. For example, according to the numbering system of Kabat, $V_H$ framework regions (FRs) and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). The present disclosure is not limited to FRs and CDRs as defined by the Kabat numbering system, but includes all numbering systems, including those discussed above. In one example, reference herein to a CDR (or a FR) is in respect of those regions according to the Kabat numbering system.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain $(C_H)$ 1 and/or the $V_L$ is not linked to a light chain constant domain $(C_L)$. Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a compound or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a compound of the disclosure reacts or associates more frequently, more rapidly, with greater duration and/or with greater affinity with a particular antigen or cell expressing same than it does with alternative antigens or cells. For example, a compound binds to G-CSFR (e.g., hG-CSFR) with materially greater affinity (e.g., 20 fold or 40 fold or 60 fold or 80 fold to 100 fold or 150 fold or 200 fold) than it does to other cytokine receptor or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

A protein or antibody may be considered to "preferentially bind" to a polypeptide if it binds that polypeptide with a dissociation constant $(K_D)$ that is less than the protein's or antibody's $K_D$ for another polypeptide. In one example, a protein or antibody is considered to preferentially bind to a polypeptide if it binds the polypeptide with an affinity (i.e., $K_D$) that is at least about 20 fold or 40 fold or 60 fold or 80 fold or 100 fold or 120 fold or 140 fold or 160 fold more than the protein's or antibody's $K_D$ for another polypeptide.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

An "$IC_{50}$ of at least about" will be understood to mean that the $IC_{50}$ is equal to the recited value or greater (i.e., the value recited as the $IC_{50}$ is lower), i.e., an $IC_{50}$ of 2 nM is greater than an $IC_{50}$ of 3 nM. Stated another way, this term could be "an $IC_{50}$ of X or less", wherein X is a value recited herein.

As used herein, the term "epitope" (syn. "antigenic determinant") shall be understood to mean a region of hG-CSFR to which a protein comprising an antigen binding site of an antibody binds. This term is not necessarily limited to the specific residues or structure to which the protein makes contact. For example, this term includes the region spanning amino acids contacted by the protein and/or 5-10 or 2-5 or 1-3 amino acids outside of this region. In some examples, the epitope comprises a series of discontinuous amino acids that are positioned close to one another when hG-CSFR is folded, i.e., a "conformational epitope". For example, a conformational epitope comprises amino acids in one or more or two or more or all of the regions corresponding to 111-115, 170-176, 218-234 and/or 286-300 of SEQ ID NO: 1. The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that a protein of the disclosure (or an antigen binding site thereof) reduces or prevents binding of a recited antibody or protein to G-CSFR, e.g., to hG-CSFR. This may be due to the protein (or antigen binding site) and antibody binding to the same or an overlapping epitope. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Preferably, the protein reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to G-CSFR either in the presence or absence of the protein. If less antibody binds in the presence of the protein than in the absence of the protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit a protein (or antigen binding site thereof) that binds to one epitope to competitively inhibit the binding of a protein (or antigen binding site) that binds to the other epitope. For example, the "overlapping" epitopes share at least 1 or 2 or 3 or 4 or 5 or 6 or 7 or 8 or 9 or 20 amino acids.

As used herein, the term "neutralize" shall be taken to mean that a compound is capable of blocking, reducing or preventing G-CSF-mediated signaling in a cell through the G-CSFR. Methods for determining neutralization are known in the art and/or described herein.

Complications Associated with Sickle Cell Disease

The present disclosure provides, for example, a method for treating or preventing or delaying progression or reducing or inhibiting or hindering development of a complication associated with sickle cell disease in a subject suffering from sickle cell disease, the method comprising administering a compound that inhibits granulocyte colony stimulating factor (G-CSF) signaling. For example, the compound binds to G-CSF or G-CSFR.

As used herein, the term "sickle cell disease" refers to group of inherited disorders that cause red blood cells to become misshapen and break down. It will be apparent to the skilled person that the type of sickle cell disease depends on the genes inherited from their parents. As used herein, this term encompasses all types of sickle cell disease including sickle cell anemia (HbSS), hemoglobin sickle cell disease (HbSC), sickle cell-hemoglobin D disease (HbSD), sickle cell-hemoglobin E disease (HbSE), sickle cell-hemoglobin O disease (HbSO), hemoglobin sickle-beta-thalassemia (Hb S beta-thalassemia) and sickle cell trait (SCT).

In one example, the subject has or is suffering from sickle cell anemia (HbSS). It will be apparent to the skilled person that a subject with HbSS has inherited two genes one from each parent, that code for hemoglobin "S." Hemoglobin S is an abnormal form of hemoglobin that causes the red cells to become rigid, and sickle shaped.

In one example, the subject has or is suffering from hemoglobin sickle cell disease (HbSC). It will be apparent to the skilled person that a subject with HbSC has inherited a hemoglobin "S" gene from one parent and a gene for a different type of abnormal hemoglobin called "C" from the other parent.

In one example, the subject has or is suffering from hemoglobin sickle-beta-thalassemia (Hb S beta-thalassemia). It will be apparent to the skilled person that a subject with Hb S beta-thalassemia have inherited a hemoglobin "S" gene from one parent and a gene for beta thalassemia, another type of hemoglobin abnormality, from the other parent. There are two types of beta thalassemia: "zero" (HbS beta$^0$) and "plus" (HbS beta$^+$). In one example, the subject has Hb S beta$^0$-thalassemia. In another example, the subject has Hb S beta$^+$-thalassemia.

In one example, the subject has or is suffering from sickle cell-hemoglobin D disease (HbSD). It will be apparent to the skilled person that a subject with HbSD has inherited a hemoglobin "S" gene from one parent and a gene for a different type of abnormal hemoglobin called "D" from the other parent.

In one example, the subject has or is suffering from sickle cell-hemoglobin E disease (HbSE). It will be apparent to the skilled person that a subject with HbSD has inherited a hemoglobin "S" gene from one parent and a gene for a different type of abnormal hemoglobin called "E" from the other parent.

In one example, the subject has or is suffering from sickle cell-hemoglobin O disease (HbSO). It will be apparent to the skilled person that a subject with HbSD has inherited a hemoglobin "S" gene from one parent and a gene for a different type of abnormal hemoglobin called "E" from the other parent.

In one example, the subject has or is suffering from sickle cell trait (SCT). It will be apparent to the skilled person that a subject with SCT has inherited a hemoglobin "S" gene from one parent and a normal gene (one that codes for hemoglobin "A") from the other parent.

It will be apparent to the skilled person that currently there is no accepted International classification system of overall sickle cell disease severity.

In one example, the severity of sickle cell disease is classified based on the RAND/UCLA modified Delphi panel. For example, the subject has Class I-III sickle cell disease as described in Shah et al., *Clinicoecon Outcomes Res*. 2020; 12:625-633.

In one example, a subject has Class I sickle cell disease. For example, a subject with Class I sickle cell disease is 8-40 years with no end organ damage, no chronic pain, and ≤4 unscheduled acute care visits due to vaso-occlusive crises (VOC) in the last year. In one example, a subject with Class I sickle cell disease is <8 or >40 years with no end organ damage, no chronic pain, and <2 unscheduled acute care visits.

In one example, the subject has Class II sickle cell disease. For example, a subject with Class II sickle cell disease is ≥25 years with severe retinopathy, no chronic pain, and 0-1 unscheduled acute care visits. In one example, a subject has Class II sickle cell disease if they do not meet the Class I or Class III criteria.

In one example, the subject has Class III sickle cell disease. For example, a subject with Class III sickle cell disease is any age with ≥5 unscheduled acute care visits and/or with severe damage to bone, retina, heart, lung, kidney, or brain.

It will be apparent to the skilled person from the disclosure herein that the severity of sickle cell disease is based not only on the genotype of the disease but also on the complication(s) associated with the sickle cell disease.

In one example, the subject is suffering from a complication associated with sickle cell disease (i.e., the subject is in need to treatment).

In one example, the complication associated with sickle cell disease is acute.

In one example, the complication associated with sickle cell disease is chronic.

Complications of sickle cell disease will be known to the skilled person and/or described herein.

In one example, the complication associated with sickle cell disease affects the cardiovascular system, the central nervous system, the dental system, endocrine system, gallbladder and/or pancreas, gastrointestinal system, genitourinary system, hematopoietic system, hepatic system, immune system, ophthalmic system, pulmonary system, renal system, reproductive system, skin and/or spleen.

In one example, the complication associated with sickle cell disease is selected from the group consisting of fatigue, dyspnea, syncope, relative systolic hypertension, myocardial infarction, acute myocardial infarction, sickle cardiomyopathy, left ventricular hypertrophy, diastolic dysfunction, heart failure with preserved ejection fraction, iron-induced cardiomyopathy and dysrhythmias, endothelial dysfunction/autonomic dysfunction, prolonged QT interval, pulmonary hypertension, headache, infarctive stroke, hemorrhagic stroke, ischemic stroke, aneurysm, ruptured aneurysm, moyamoya syndrome, silent cerebral infarct, sinovenous thrombosis, ischemia-reperfusion injury, chronic headache, neurocognitive disorders due to silent cerebral infarcts/overt cerebrovascular accidents or strokes, intraparenchymal hemorrhage, subarachnoid hemorrhage, intraventricular hemorrhage, chronic anemia, anemia crisis, poor executive functioning, memory deficits, increased cerebral blood flow, blood transfusion requirement, organ damage, pain medicine requirement, vasculopathy, cerebral vasculopathy, microvascular stasis, vaso-occlusion, vaso-occlusive crisis (VOC), vascular stasis, venous stasis, moyamoya syndrome, cerebral aneurysm, dental abscess, dental crown fracture, dental pulp fracture, dental caries, gingivitis, cracked teeth, early dental loss, misaligned dentition, pain around menses, pregnancy, menopause, growth hormone deficiency, hypogonadism, disturbances in cortisol levels, delayed puberty, premature menopause, cholelithiasis, cholecystitis, common bile duct obstruction, acute pancreatitis, chronic gallbladder sludge, dyspepsia, chronic cholecystitis, chronic pancreatitis, mesenteric infarcts, chronic abdominal pain, constipation, irritable bowel syndrome, GERD, increased abdominal girth due to shortened trunk and barrel chest (sickle-habitus), priapism, enuresis, hematuria, menses-induced VOE, erectile (sexual) dysfunction, postcoital pain, enuresis/nocturia, hematuria, acute anemia, aplastic crisis, sequestration crises, splenic sequestration crisis, hyperhemolytic crisis, functional asplenia, indirect hyperbilirubinemia, scleral icterus, hemostatic activation, chronic hemolysis, chronic anemia, extramedullary hematopoiesis, leukocytosis, thrombocytosis, splenomegaly, hypersplenism, conjunctival pallor, scleral icterus, hemostatic activation, thrombophilia, hyperbilirubinemia, hepatic sequestration, hepatitis, acute intrahepatic cholelithiasis/cholestasis, acute and/or chronic renal failure, transaminitis, hepatic failure, hepatomegaly, hepatic congestion/chronic congestive hepatopathy, hepatic sequestration, portal hypertension, nephropathy, bacteremia/sepsis, iron overload, meningitis, hepatitis, osteomyelitis, pyelonephritis, influenza, osteomyelitis, hepatitis, dental abscesses, gingivitis, leg ulcer super infection, retinal detachment, retinal artery occlusion, vitreous hemorrhage, peripheral retinal ischemia, macular infarction, sickle retinopathy (proliferative and nonproliferative), maculopathy, chest syndrome, acute chest syndrome, pneumonia, pulmonary fat embolism syndrome, airway hyperreactivity, atelectasis from hypoventilation, pulmonary embolism, chronic lung disease, chronic hypoxemia/hypoxia, nocturnal hypoxemia, chronic pulmonary embolism, acute kidney injury (recurrent), hematuria, papillary necrosis, hypertension, thromboemboli, glomerular hyperfiltration, proteinuria/microalbuminuria, hyposthenuria, chronic kidney disease, end-stage renal disease, renal tubular acidosis, renal osteodystrophy, spontaneous abortion/miscarriages, intrauterine growth retardation, early fetal demise, pre- and post-eclampsia, severe dilutional anemia, other maternal-fetal complications, low sperm counts/poor sperm function, post-pregnancy chronic pain, leg ulcers, varicosity, acute splenic sequestration, acute splenic infarction, splenic abscesses, traumatic spleen rupture, functional asplenia or hyposplenia due to auto-infarction of spleen leading to increased risk for infection with encapsulated organisms, splenic infarction, hypersplenism, pain crisis and combinations thereof.

In one example, the complication associated with sickle cell disease affects the cardiovascular system. In one example, the complication is acute. For example, the acute complication is fatigue, dyspnea, syncope, relative systolic hypertension and/or myocardial infarction. In one example, the complication is chronic. For example, the chronic complication is sickle cardiomyopathy, left ventricular hypertrophy, diastolic dysfunction, heart failure with preserved ejection fraction, iron-induced cardiomyopathy and dysrhythmias, endothelial dysfunction/autonomic dysfunction, prolonged QT interval and/or pulmonary hypertension.

In one example, the complication associated with sickle cell disease affects the central nervous system. In one example, the complication is acute. For example, the acute complication is a headache, infarctive stroke, hemorrhagic stroke, ruptured aneurysm, moyamoya syndrome, silent cerebral infarct and/or sino-venous thrombosis. In one example, the complication is chronic. For example, the chronic complication is chronic headache, neurocognitive disorders due to silent cerebral infarcts/overt cerebrovascular accidents or strokes and chronic anemia, poor executive functioning, memory deficits, increased cerebral blood flow, cerebral vasculopathy and moyamoya syndrome and/or cerebral aneurysm.

In one example, the complication associated with sickle cell disease affects the dental system. In one example, the complication is acute. For example, the acute complication is dental abscess, dental crown fracture and/or dental pulp fracture. In one example, the complication is chronic. For example, the chronic complication is dental caries, gingivitis, cracked teeth, early dental loss and/or misaligned dentition.

In one example, the complication associated with sickle cell disease affects the endocrine system. In one example, the complication is acute. For example, the acute complication is pain around menses, pregnancy, and menopause. In one example, the complication is chronic. For example, the chronic complication is growth hormone deficiency, hypogonadism, disturbances in cortisol levels, delayed puberty and/or premature menopause.

In one example, the complication associated with sickle cell disease affects the gallbladder and/or pancreas. In one example, the complication is acute. For example, the acute complication is cholelithiasis, cholecystitis, common bile duct obstruction and/or acute pancreatitis. In one example, the complication is chronic. For example, the chronic complication is chronic gallbladder sludge, dyspepsia, chronic cholecystitis and/or chronic pancreatitis.

In one example, the complication associated with sickle cell disease affects the gastrointestinal system. In one example, the complication is acute. For example, the acute complication is mesenteric infarcts. In one example, the complication is chronic. For example, the chronic complication is chronic abdominal pain, constipation, irritable bowel syndrome, GERD and/or increased abdominal girth due to shortened trunk and barrel chest (sickle-habitus).

In one example, the complication associated with sickle cell disease affects the genitourinary system. In one example, the complication is acute. For example, the acute complication is priapism, enuresis, hematuria and/or menses-induced VOE. In one example, the complication is chronic. For example, the chronic complication is erectile (sexual) dysfunction, postcoital pain, enuresis/nocturia and/or hematuria.

In one example, the complication associated with sickle cell disease affects the hematopoietic system. In one example, the complication is acute. For example, the acute complication is acute anemia, aplastic crisis, sequestration crises, functional asplenia, indirect hyperbilirubinemia, scleral icterus and/or hemostatic activation. In one example, the complication is chronic. For example, the chronic complication is chronic hemolysis, chronic anemia, extramedullary hematopoiesis, leukocytosis, thrombocytosis, splenomegaly, hypersplenism, conjunctival pallor, scleral icterus, hemostatic activation and/or thrombophilia.

In one example, the complication associated with sickle cell disease affects the hepatic system. In one example, the complication is acute. For example, the acute complication is hyperbilirubinemia, hepatic sequestration, hepatitis, acute intrahepatic cholelithiasis/cholestasis and/or transaminitis. In one example, the complication is chronic. For example, the chronic complication is hepatomegaly, hepatic congestion/chronic congestive hepatopathy and/or portal hypertension.

In one example, the complication associated with sickle cell disease affects the immune system. In one example, the complication is acute. For example, the acute complication is bacteremia/sepsis, meningitis, hepatitis, osteomyelitis, pyelonephritis and/or influenza. In one example, the complication is chronic. For example, the chronic complication is osteomyelitis, hepatitis, dental abscesses, gingivitis and/or leg ulcer super infection.

In one example, the complication associated with sickle cell disease affects the ophthalmic system. In one example, the complication is acute. For example, the acute complication is retinal detachment, retinal artery occlusion, vitreous hemorrhage and/or macular infarction. In one example, the complication is chronic. For example, the chronic complication is sickle retinopathy (proliferative and nonproliferative) and/or maculopathy.

In one example, the complication associated with sickle cell disease affects the pulmonary system. In one example, the complication is acute. For example, the acute complication is acute chest syndrome, pneumonia, pulmonary fat embolism syndrome, airway hyperreactivity, atelectasis from hypoventilation and/or pulmonary embolism. In one example, the complication is chronic. For example, the chronic complication is chronic lung disease, chronic hypoxemia/hypoxia, nocturnal hypoxemia and/or chronic pulmonary embolism.

In one example, the complication associated with sickle cell disease affects the renal system. In one example, the complication is acute. For example, the acute complication is acute kidney injury (recurrent), hematuria and/or papillary necrosis. In one example, the complication is chronic. For example, the chronic complication is hypertension, glomerular hyperfiltration, proteinuria/microalbuminuria, hyposthenuria, chronic kidney disease, end-stage renal disease, renal tubular acidosis and/or renal osteodystrophy.

In one example, the complication associated with sickle cell disease affects the reproductive system. In one example, the complication is acute. For example, the acute complication is spontaneous abortion/miscarriages, intrauterine growth retardation, early fetal demise, pre- and post-eclampsia, severe dilutional anemia and/or other maternal-fetal complications. In one example, the complication is chronic. For example, the chronic complication is low sperm counts/poor sperm function or post-pregnancy chronic pain.

In one example, the complication associated with sickle cell disease affects the skin. In one example, the complication is acute. For example, the acute complication is leg ulcers. In one example, the complication is chronic. For example, the chronic complication is leg ulcers and/or varicosity.

In one example, the complication associated with sickle cell disease affects the spleen. In one example, the complication is acute. For example, the acute complication is acute splenic sequestration, acute splenic infarction, splenic abscesses and/or traumatic spleen rupture. In one example, the complication is chronic. For example, the chronic complication is splenomegaly, functional asplenia or hyposplenia due to auto-infarction of spleen leading to increased risk for infection with encapsulated organisms, splenic infarction and/or hypersplenism.

In one example, the complication associated with sickle cell disease is a vasculopathy. As used herein, the term "vasculopathy" refers to any disease affecting the blood vessels.

In one example, the vasculopathy is associated with a vaso-occlusion. As used herein, the term "vaso-occlusion" or "vascular occlusion" refers to a blockage of a blood vessel, usually with a clot.

In one example, the subject has or is suffering from a complication of the vaso-occlusion. For example, the complication is a vaso-occlusive crisis. As used herein, the term "vaso-occlusive crisis" shall be understood to refer to a complication wherein the microcirculation is obstructed by sickled red blood cells, causing ischemic injury to the organ supplied and resultant pain. "Pain associated with vaso-occlusive crisis" will be understood to refer to the pain relating to, or resulting from, or caused by occlusion of a blood vessel.

In one example, the compound that inhibits G-CSF signaling is administered in an amount sufficient to reduce and/or prevent and/or inhibit neutrophil adhesion to endothelial cells and transmigration. As used herein, the phrase "neutrophil adhesion to endothelial cells and transmigration" refers to a multistep cascade of adhesive and migratory events, mediated by three classes of adhesion receptors including selectins, integrins and adhesion receptors of the immunoglobulin superfamily. The skilled person will recognize the process comprises (i) initial selectin-mediated rolling, (ii) chemokine-induced activation and (iii) integrin-dependent firm adhesion and subsequent transendothelial migration. Methods for assessing neutrophil adhesion and transendothelial migration include, but are not limited to, immunohistochemistry for markers including for example, P-selectin, E-selectin and ICAM-1.

In one example, the compound that inhibits G-CSF signaling is administered in an amount sufficient to reduce and/or prevent and/or inhibit neutrophil-platelet aggregate formation. Methods for assessing neutrophil-platelet aggregate formation include, but are not limited to, flow cytometry by staining for CD11b, CD16 and CD66b to select for highly enriched neutrophils and CD62L (L-selectin) and CD64 (FcgRI) as neutrophil activation markers.

In one example, the compound that inhibits G-CSF signaling is administered in an amount sufficient to reduce and/or prevent and/or inhibit neutrophil extracellular trap (NET) formation. It will be apparent to the skilled person that reference to "NET formation" refers to the formation of the network of extracellular fibers, primarily composed of DNA from neutrophils, that bind pathogenic microbes. Methods for assessing NET formation include, but are not limited to, measurement of neutrophil elastase-α1-antitrypsin complexes and myeloperoxidase-α1-antitrypsin complexes.

In one example, the compound that inhibits G-CSF signaling is administered in an amount sufficient to reduce and/or prevent and/or inhibit neutrophil extracellular trap (NET) activation. It will be apparent to the skilled person that reference to "NET activation" refers to the process of NETosis which is a form of cell death that is characterized by the release of decondensed chromatin and granular contents into the extracellular space. Methods for assessing NET formation include, but are not limited to, measuring NETosis markers such as the level of expression of peptidyl arginine deiminase 4 (PADI4), elastase, neutrophil expressed (ELANE), nucleosomes, elastase-α-antitrypsin complexes and myeloperoxidase (MPO), MPO activity and/or dsDNA.

In one example, the compound that inhibits G-CSF signaling is administered in an amount sufficient to reduce and/or prevent and/or inhibit reactive oxygen species formation. Methods for assessing reactive oxygen species formation include, but are not limited to, flow cytometry.

In one example, the compound that inhibits G-CSF signaling is administered in an amount sufficient to reduce and/or prevent and/or inhibit von Willebrand factor secretion from endothelial cells. Methods for assessing von Willebrand factor secretion from endothelial cells include, but are not limited to, immunofluorescence.

In one example, the compound that inhibits G-CSF signaling is administered in an amount sufficient to reduce and/or prevent and/or inhibit neutrophil activation. As used herein, the term "neutrophil activation" refers to the process in which the neutrophil is stimulated by binding of a stimulatory substance resulting in degranulation and/or generation of reactive oxygen products. Methods of measuring neutrophil activation will be known to those skilled in the art and/or described herein. For example, neutrophil activation can be measured directly by measuring the levels of expression of e.g., CD11b, CD66b and/or CD64 in an affected tissue. Suitable methods for measuring expression levels will be apparent to the skilled person and/or described herein.

In one example, the compound that inhibits G-CSF signaling is administered in an amount sufficient to reduce and/or prevent and/or inhibit endothelial cell activation. As used herein, the term "endothelial cell activation" refers to the proinflammatory and procoagulant state of the endothelial cells lining the lumen of blood vessels. It will be apparent to the skilled person that endothelial cell activation results in loss of vascular integrity, expression of leucocyte adhesion molecules, change in phenotype from antithrombotic to prothrombotic, cytokine production and upregulation of HLA molecules. Methods for assessing endothelial cell activation include, but are not limited to, western blot.

In one example, the compound that inhibits G-CSF signaling is administered in an amount sufficient to reduce or prevent an increase in neutrophil infiltration and/or accumulation in the subject's liver. As used herein, the terms "neutrophil infiltration" and "neutrophil accumulation" refer to the recruitment or accumulation of neutrophils in tissues or cells in response to a variety of substances being released at the sites of inflammatory reactions. Methods of measuring neutrophil infiltration will be known to those skilled in the art. For example, the neutrophils can be measured directly, such as by visualisation by fluorescence microscopy, or indirectly by measuring the abundance or activity of neutrophil specific proteins or enzymes in an affected tissue. Suitable methods for measuring neutrophil infiltration are described in Soo-Jeong Yu et al Korean J Intern Med (2008) and Pulli et al PloS One (2013). Methods for assessing the levels of neutrophils in e.g., lung tissue can be measured by flow cytometry or immunohistochemistry (e.g., as described in Wang et al., Clin Sci Lond, 2017 131:2347-2362).

In one example, the compound that inhibits G-CSF signaling is administered in an amount sufficient to reduce or prevent an increase in percent vascular stasis. As used herein, the term "vascular stasis" or vasostasis" refers to a condition of slow blood flow in the vasculature. As used herein, the term "microvascular stasis" refers to slowing blood flow in the microvasculature. It will be apparent that these terms include "venous stasis" or "venostasis" which refers to a condition of slow blood flow in the veins. Methods for assessing vascular stasis include, but are not limited to, Doppler ultrasonography and transcranial Doppler ultrasonography.

Antibodies

In one example, a compound as described herein according to any example is a protein comprising an antigen binding site of an antibody. In some examples, the compound that inhibits G-CSF signaling is an antibody. In some examples, the antibody binds to G-CSFR. In some examples, the antibody binds to G-CSF.

Methods for generating antibodies are known in the art and/or described in Harlow and Lane (editors) Antibodies: A Laboratory Manual, Cold Spring Harbor Laboratory, (1988). Generally, in such methods G-CSFR or G-CSF (e.g., hG-CSFR or hG-CSF) or a region thereof (e.g., an extracellular domain) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

Monoclonal antibodies are one exemplary form of an antibody contemplated by the present disclosure. The term "monoclonal antibody" or "mAb" refers to a homogeneous antibody population capable of binding to the same antigen (s), for example, to the same epitope within the antigen. This term is not intended to be limited as regards to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

Alternatively, ABL-MYC technology (NeoClone, Madison WI 53713, USA) is used to produce cell lines secreting MAbs (e.g., as described in Largaespada et al, *J. Immunol. Methods*. 197: 85-95, 1996).

Antibodies can also be produced or isolated by screening a display library, e.g., a phage display library, e.g., as described in U.S. Pat. Nos. 6,300,064 and/or 5,885,793. For example, the present inventors have isolated fully human antibodies from a phage display library.

The antibody of the present disclosure may be a synthetic antibody. For example, the antibody is a chimeric antibody, a humanized antibody, a human antibody or a de-immunized antibody.

In one example, an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Methods for producing chimeric antibodies are described in, e.g., U.S. Pat. Nos. 4,816,567; and 5,807,715.

The antibodies of the present disclosure may be humanized or human.

The term "humanized antibody" shall be understood to refer to a subclass of chimeric antibodies having an antigen binding site or variable region derived from an antibody from a non-human species and the remaining antibody structure based upon the structure and/or sequence of a human antibody. In a humanized antibody, the antigen-binding site generally comprises the complementarity determining regions (CDRs) from the non-human antibody grafted onto appropriate FRs in the variable regions of a human antibody and the remaining regions from a human antibody. Antigen binding sites may be wild-type (i.e., identical to those of the non-human antibody) or modified by one or more amino acid substitutions. In some instances, FR residues of the human antibody are replaced by corresponding non-human residues.

Methods for humanizing non-human antibodies or parts thereof (e.g., variable regions) are known in the art. Humanization can be performed following the method of U.S. Pat. No. 5,225,539, or 5,585,089. Other methods for humanizing an antibody are not excluded.

The term "human antibody" as used herein refers to antibodies having variable regions (e.g. $V_H$, $V_L$) and, optionally constant regions derived from or corresponding to sequences found in humans, e.g. in the human germline or somatic cells.

Exemplary human antibodies are described herein and include C1.2 and C1.2G and/or variable regions thereof. These human antibodies provide an advantage of reduced immunogenicity in a human compared to non-human antibodies. Exemplary antibodies are described in WO2012171057, which is incorporated herein by reference.

Antibody Binding Domain Containing Proteins

Single-Domain Antibodies

In some examples, a compound of the disclosure is a protein that is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, MA; see, e.g., U.S. Pat. No. 6,248,516).

Diabodies, Triabodies, Tetrabodies

In some examples, a protein of the disclosure is or comprises a diabody, triabody, tetrabody or higher order protein complex such as those described in WO98/044001 and/or WO94/007921.

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Antibody Fragments

The present disclosure also contemplates other antibodies and antibody fragments, such as:
(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980; and
(iv) $Fab_3$ (e.g., as described in EP19930302894).

V-Like Proteins

An example of a compound of the disclosure is a T-cell receptor. T cell receptors have two V-domains that combine into a structure similar to the Fv module of an antibody. Novotny et al., *Proc Natl Acad Sci USA* 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250,297B1 or US20070224633.

Affibodies

In a further example, a compound of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Soluble G-CSFR

The present disclosure also contemplates a soluble form of the G-CSFR which competes with the naturally occurring membrane-associated G-CSFR for G-CSF interaction. Those skilled in the art can readily prepare soluble forms of the receptor, see for example U.S. Pat. No. 5,589,456 and Honjo et al, *Acta Crystallograph Sect F Struct Biol Cryst Commun.* 61(Pt 8):788-790, 2005.

De-Immunized Antibodies and Proteins

The present disclosure also contemplates a de-immunized antibody or protein. De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO2000/34317, WO2004/108158 and WO2004/064724.

Methods for introducing suitable mutations and expressing and assaying the resulting protein will be apparent to the skilled artisan based on the description herein.

Mutations to Proteins

The present disclosure also contemplates mutant forms of a protein of the disclosure. In this regard, data presented herein indicate sites within a CDR of a protein of the disclosure that can be changed in addition to exemplary changes that can be made. The skilled person will understand that changes can additionally or alternatively be made within a framework region of a variable region containing protein without inhibiting or significantly reducing its function in the context of the present disclosure.

For example, such a mutant protein comprises one or more conservative amino acid substitutions compared to a sequence set forth herein. In some examples, the protein comprises 30 or fewer or 20 or fewer or 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In one example, a mutant protein has only, or not more than, one or two or three or four or five or six conservative amino acid changes when compared to a naturally occurring protein. Details of conservative amino acid changes are provided below. As the skilled person would be aware, e.g., from the disclosure herein, such minor changes can reasonably be predicted not to alter the activity of the protein.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

The present disclosure also contemplates non-conservative amino acid changes (e.g., substitutions) in a protein of the present disclosure, e.g., in a CDR, such as CDR3. For example, the present inventors have identified several non-conservative amino acid substitutions that can be made while retaining an activity of a protein of the disclosure. In one example, the protein comprises fewer than 6 or 5 or 4 or 3 or 2 or 1 non-conservative amino acid substitutions, e.g., in a CDR3, such as in a CDR3.

The present disclosure also contemplates one or more insertions or deletions compared to a sequence set forth herein. In some examples, the protein comprises 10 or fewer, e.g., 9 or 8 or 7 or 6 or 5 or 4 or 3 or 2 insertions and/or deletions.

Constant Regions

The present disclosure encompasses proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including TgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA*, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol Chem.* 276(9):6591-604, 2001). Additional examples of non-immunostimulatory Fc regions are described, for example, in Dall'Acqua et al., *J Immunol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications/Variants

The present disclosure also contemplates additional modifications or variants to an antibody or protein of the disclosure.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

In one example, the protein of the disclosure additionally comprises albumin, a functional fragment or variant thereof. In one example, the albumin, functional fragment or variant thereof is serum albumin, such as human serum albumin. In one example, the albumin, functional fragment or variant thereof, comprises one or more amino acid substitutions, deletions or insertions, e.g., no more than 5 or 4 or 3 or 2 or 1 substitutions.

Amino acid substitutions suitable for use in the present disclosure will be apparent to the skilled person and include naturally-occurring substitutions and engineered substitutions such as those described, for example, in WO2011051489, WO2014072481, WO2011103076, WO2012112188, WO2013075066, WO2015063611 and WO2014179657.

In one example, the protein or antibody of the disclosure comprises one or more variants. For example, the variant is a post-translationally modified variant.

In one example, the protein or antibody comprises a variant missing an encoded C-terminal lysine residue, a deamidated variant, a miscorporated amino acid residue, a glycosylated variant, a variant comprising a pyroglutamate, a variant lacking a N-terminal residue, and/or a variant comprising all or part of a secretion signal.

In one example, the protein or antibody comprises a variant missing an encoded C-terminal lysine residue.

In one example, the protein or antibody comprises a deamidated variant. Deamidated variants of encoded asparagine residues may result in isoaspartic acid and/or aspartic acid being generated or even a succinamide involving an adjacent amino acid residue. Deamidated variants of encoded glutamine residues may result in glutamic acid being formed. Compositions comprising a heterogeneous mixture of such sequences and variants are intended to be included when reference is made to a particular amino acid sequence.

In one example, the protein or antibody comprises a miscorporated amino acid residue. For example, methionine residues are substituted with nor-leucine, asparagine residues are substituted with serine and/or phenylalanine residues are substituted with tyrosine.

In one example, the protein or antibody comprises a variant comprising a pyroglutamate. For example, at the N-terminus of a protein.

In one example, the protein or antibody comprises a glycosylated variant.

In one example, the protein or antibody comprises a variant lacking a N-terminal residue. For example, a N-terminal glutamine in an antibody or V region.

In one example, the protein or antibody comprises a variant comprising all or part of a secretion signal.

Protein Production

In one example, a protein described herein according to any example is produced by culturing a hybridoma under conditions sufficient to produce the protein, e.g., as described herein and/or as is known in the art.

Recombinant Expression

In another example, a protein described herein according to any example is recombinant.

In the case of a recombinant protein, nucleic acid encoding same can be cloned into expression constructs or vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising Pichia pastoris, Saccharomyces cerevisiae and S. pombe, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickelnitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Nucleic Acid-Based G-CSF Signaling Inhibitors

In one example of the disclosure, therapeutic and/or prophylactic methods as described herein according to any example of the disclosure involve reducing expression of G-CSF and/or G-CSFR. For example, such a method involves administering a compound that reduces transcription and/or translation of a nucleic acid encoding G-CSF or G-CSFR. In one example, the compound that inhibits G-CSF signaling is a nucleic acid, e.g., an antisense polynucleotide, a ribozyme, a PNA, an interfering RNA, a siRNA, a microRNA.

In another example, the compound that inhibits G-CSF signaling is a nucleic acid encoding a protein compound that inhibits G-CSF signaling (e.g., an antibody or antigen binding fragment thereof).

Antisense Nucleic Acids

The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding G-CSF or G-CSFR, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding G-CSF or G-CSFR. The full-length sequence complementary to the entire gene transcript may be used. The length can be 100-2000 nucleotides. The degree of identity of the antisense sequence to the targeted transcript should be at least 90%, for example, 95-100%.

Exemplary antisense nucleic acids against G-CSF or G-CSFR are described, for example, in WO2011032204.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding G-CSF or G-CSFR. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815. Such dsRNA molecules for RNAi include, but are not limited to short hairpin RNA (shRNA) and bi-functional shRNA.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search.

Aptamers

In another example, a compound is a nucleic acid aptamer (adaptable oligomer). Aptamers are single stranded oligonucleotides or oligonucleotide analogs that are capable of forming a secondary and/or tertiary structure that provides the ability to bind to a particular target molecule, such as a protein or a small molecule, e.g., G-CSF or G-CSFR. Thus, aptamers are the oligonucleotide analogy to antibodies. In general, aptamers comprise about 15 to about 100 nucleotides, such as about 15 to about 40 nucleotides, for example about 20 to about 40 nucleotides, since oligonucleotides of a length that falls within these ranges can be prepared by conventional techniques.

An aptamer can be isolated from or identified from a library of aptamers. An aptamer library is produced, for example, by cloning random oligonucleotides into a vector (or an expression vector in the case of an RNA aptamer), wherein the random sequence is flanked by known sequences that provide the site of binding for PCR primers. An aptamer that provides the desired biological activity (e.g., binds specifically to G-CSF or G-CSFR) is selected. An aptamer with increased activity is selected, for example, using SELEX (Sytematic Evolution of Ligands by EXponential enrichment). Suitable methods for producing and/or screening an aptamer library are described, for example, in Ellington and Szostak, *Nature* 346:818-22, 1990; U.S. Pat. Nos. 5,270,163; and/or 5,475,096.

Assaying Activity of a Compound Binding to G-CSFR and Mutants Thereof

It will be apparent to the skilled artisan from the disclosure herein that some compounds of the present disclosure bind to the ligand binding domain of hG-CSFR and to specific mutant forms of the ligand binding domain of hG-CSFR (e.g., SEQ ID NO: 1 without or with certain point mutations) and/or bind to both human and cynomolgus monkey G-CSFR. Methods for assessing binding to a protein are known in the art, e.g., as described in Scopes (In: Protein purification: principles and practice, Third Edition, Springer Verlag, 1994). Such a method generally involves labeling the protein and contacting it with immobilized compound. Following washing to remove non-specific bound protein, the amount of label and, as a consequence, bound protein is detected. Of course, the protein can be immobilized and the compound that inhibits G-CSF signaling labeled. Panning-type assays can also be used. Alternatively, or additionally, surface plasmon resonance assays can be used.

The assays described above can also be used to detect the level of binding of a compound to hG-CSFR or a ligand binding domain thereof (e.g., SEQ ID NO: 1) or mutant form thereof.

In one example, a protein of the present disclosure binds to a polypeptide of SEQ ID NO: 1 in which an alanine is substituted for the lysine at position 167 of SEQ ID NO: 1 and/or in which an alanine is substituted for the histidine at position 168 of SEQ ID NO: 1 at substantially the same level (e.g., within 10% or 5% or 1%) as it binds to SEQ ID NO: 1.

In one example, a protein of the present disclosure binds to a polypeptide of SEQ ID NO: 1 in which an alanine is substituted for the arginine at position 287 of SEQ ID NO: 1 at a level at least about 100 fold or 150 fold or 160 fold or 200 fold lower than it binds to a polypeptide of SEQ ID NO: 1. In one example, a protein of the present disclosure binds to a polypeptide of SEQ ID NO: 1 in which an alanine is substituted for the arginine at position 287 of SEQ ID NO: 1 at a level at least about 160 fold lower than it binds to a polypeptide of SEQ ID NO: 1.

In one example, a protein of the present disclosure binds to a polypeptide of SEQ ID NO: 1 in which an alanine is substituted for the histidine at position 237 of SEQ ID NO: 1 at a level at least about 20 fold or 40 fold or 50 fold or 60 fold lower than it binds to a polypeptide of SEQ ID NO: 1. In one example, a protein of the present disclosure binds to a polypeptide of SEQ ID NO: 1 in which an alanine is substituted for the histidine at position 237 of SEQ ID NO: 1 at a level at least about 50 fold lower than it binds to a polypeptide of SEQ ID NO: 1.

In one example, a protein of the present disclosure binds to a polypeptide of SEQ ID NO: 1 in which an alanine is substituted for the methionine at position 198 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the methionine at position 198 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the tyrosine at position 172 of SEQ ID NO: 1 at a level at least about 20 fold or 30 fold or 40 fold lower than it binds to a polypeptide of SEQ ID NO: 1. In one example, a protein of the present disclosure binds to a polypeptide of SEQ ID NO: 1 in which an alanine is substituted for the tyrosine at position 172 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the leucine at position 171 of SEQ ID NO: 1 at a level at least about 100 fold or 120 fold or 130 fold or 140 fold lower than it binds to a polypeptide of SEQ ID NO: 1. In one example, a protein of the present disclosure binds to a polypeptide of SEQ ID NO: 1 in which an alanine is substituted for the leucine at position 171 of SEQ ID NO: 1 at a level at least about 140 fold lower than it binds to a polypeptide of SEQ ID NO: 1.

In one example, a protein of the present disclosure binds to a polypeptide of SEQ ID NO: 1 in which an alanine is substituted for the leucine at a position 111 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the leucine at a position 111 of SEQ ID NO: 1 at a level at least about 60 fold lower than it binds to a polypeptide of SEQ ID NO: 1.

In one example, a protein of the present disclosure binds to a polypeptide of SEQ ID NO: 1 in which an alanine is substituted for the histidine at position 168 of SEQ ID NO: 1 at a level no more than 5 fold or 4 fold or 3 fold or 2 fold or 1 fold lower than it binds to a polypeptide of SEQ ID NO: 1.

In one example, a protein of the present disclosure binds to a polypeptide of SEQ ID NO: 1 in which an alanine is substituted for the lysine at position 167 of SEQ ID NO: 1 at a level no more than 5 fold or 4 fold or 3 fold or 2 fold or 1 fold lower than it binds to a polypeptide of SEQ ID NO: 1.

The level of binding is conveniently determined using a biosensor.

The present disclosure contemplates any combination of the foregoing characteristics. In one example, a protein described herein has all of the binding characteristics set forth in the preceding seven paragraphs.

Epitope Mapping

In another example, the epitope bound by a protein described herein is mapped. Epitope mapping methods will be apparent to the skilled artisan. For example, a series of overlapping peptides spanning the hG-CSFR sequence or a region thereof comprising an epitope of interest, e.g., peptides comprising 10-15 amino acids are produced. The protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, amino acid residues within hG-CSFR are mutated, e.g., by alanine scanning mutagenesis, and mutations that reduce or prevent protein binding are determined. Any mutation that reduces or prevents binding of the protein is likely to be within the epitope bound by the protein.

A further method is exemplified herein, and involves binding hG-CSFR or a region thereof to an immobilized protein of the present disclosure and digesting the resulting complex with proteases. Peptide that remains bound to the immobilized protein are then isolated and analyzed, e.g., using mass spectrometry, to determine their sequence.

A further method involves converting hydrogens in hG-CSFR or a region thereof to deutrons and binding the resulting protein to an immobilized protein of the present disclosure. The deutrons are then converted back to hydrogen, the hG-CSFR or region thereof isolated, digested with enzymes and analyzed, e.g., using mass spectrometry to identify those regions comprising deutrons, which would have been protected from conversion to hydrogen by the binding of a protein described herein.

Optionally, the dissociation constant (Kd) of a protein for hG-CSFR or an epitope thereof is determined. The "Kd" or "Kd value" for a hG-CSFR binding protein is in one example measured by a radiolabeled or fluorescently-labeled hG-CSFR binding assay. This assay equilibrates the protein with a minimal concentration of labeled G-CSFR in the presence of a titration series of unlabeled hG-CSFR. Following washing to remove unbound hG-CSFR, the amount of label is determined, which is indicative of the Kd of the protein.

According to another example the Kd or Kd value is measured by using surface plasmon resonance assays, e.g., using BIAcore surface plasmon resonance (BIAcore, Inc., Piscataway, NJ) with immobilized hG-CSFR or a region thereof.

In some examples, proteins having a similar Kd or a higher Kd than C1.2 or C1.2G are selected, because they are likely to compete for binding to hG-CSFR.

Determining Competitive Binding

Assays for determining a protein that competitively inhibits its binding of monoclonal antibody C1.2 or C1.2G will be apparent to the skilled artisan. For example, C1.2 or C1.2G is conjugated to a detectable label, e.g., a fluorescent label or a radioactive label. The labeled antibody and the test protein are then mixed and contacted with hG-CSFR or a region thereof (e.g., a polypeptide comprising SEQ ID NO: 1) or a cell expressing same. The level of labeled C1.2 or C1.2G is then determined and compared to the level determined when the labeled antibody is contacted with the hG-CSFR, region or cells in the absence of the protein. If the level of labeled C1.2 or C1.2G is reduced in the presence of the test protein compared to the absence of the protein, the protein is considered to competitively inhibit binding of C1.2 or C1.2G to hG-CSFR.

Optionally, the test protein is conjugated to different label to C1.2 or C1.2G. This alternate labeling permits detection of the level of binding of the test protein to hG-CSFR or the region thereof or the cell.

In another example, the protein is permitted to bind to hG-CSFR or a region thereof (e.g., a polypeptide comprising SEQ ID NO: 1) or a cell expressing same prior to contacting the hG-CSFR, region or cell with C1.2 or C1.2G. A reduction in the amount of bound C1.2 or C1.2G in the presence of the protein compared to in the absence of the protein indicates that the protein competitively inhibits C1.2 or C1.2G binding to hG-CSFR. A reciprocal assay can also be performed using labeled protein and first allowing C1.2 or C1.2G to bind to G-CSFR. In this case, a reduced amount of labeled protein bound to hG-CSFR in the presence of C1.2 or C1.2G compared to in the absence of C1.2 or C1.2G indicates that the protein competitively inhibits binding of C1.2 or C1.2G to hG-CSFR.

Any of the foregoing assays can be performed with a mutant form of hG-CSFR and/or SEQ ID NO: 1 and/or a ligand binding region of hG-CSFR to which C1.2 or C1.2G binds, e.g., as described herein.

Determining Neutralization

In some examples of the present disclosure, a compound is capable of neutralizing hG-CSFR signaling.

Various assays are known in the art for assessing the ability of a compound to neutralize signaling of a ligand through a receptor.

In one example, the compound that inhibits G-CSF signaling reduces or prevents G-CSF binding to the hG-CSFR. These assays can be performed as a competitive binding assay as described herein using labeled G-CSF and/or labeled protein.

In another example, the compound that inhibits G-CSF signaling reduces formation of CFU-G when $CD34^+$ bone marrow cells are cultured in the presence of G-CSF. In such assays, $CD34^+$ bone marrow cells are cultured in a semi-solid cell culture medium in the presence of G-CSF (e.g., about 10 ng/ml cell culture medium) and, optionally stem cell factor (e.g., about 10 ng/ml cell culture medium) in the presence or absence of a test compound. After a sufficient time for granulocyte clones (CFU-G) to form, the number of clones or colonies is determined. A reduction in the number of colonies in the presence of the compound that inhibits G-CSF signaling compared to in the absence of the compound that inhibits G-CSF signaling indicates that the compound that inhibits G-CSF signaling neutralizes G-CSF signaling. By testing multiple concentrations of the compound that inhibits G-CSF signaling an $IC_{50}$ is determined, i.e., a concentration at which 50% of the maximum inhibition of CFU-G formation occurs. In one example, the $IC_{50}$ is 0.2 nM or less, such as 0.1 nM or less, for example, 0.09 nM or less, or 0.08 nM or less, or 0.07 nM or less, or 0.06 nM or less or 0.05 nM or less. In one example, the $IC_{50}$ is 0.04 nM or less. In another example, the $IC_{50}$ is 0.02 nM or less. The foregoing $IC_{50}$s relate to any CFU-G assay described herein.

In a further example, the compound that inhibits G-CSF signaling reduces proliferation of cells (e.g., BaF3 cells) expressing hG-CSFR which are cultured in the presence of G-CSF. Cells are cultured in the presence of G-CSF (e.g., 0.5 ng/ml) and the presence or absence of a test compound. Methods for assessing cell proliferation are known in the art and include, for example, MTT reduction and thymidine incorporation. A compound that reduces the level of proliferation compared to the level observed in the absence of the compound is considered to neutralize G-CSF signaling. By testing multiple concentrations of the compound an $IC_{50}$ is determined, i.e., a concentration at which 50% of the maximum inhibition of cell proliferation occurs. In one example, the $IC_{50}$ is 6 nM or less, such as 5.9 nM or less. In another example, the $IC_{50}$ is 2 nM or less or 1 nM or less or 0.7 nM or cell or 0.6 nM or less or 0.5 nM or less. The foregoing $IC_{50}$s relate to any cell proliferation assay described herein.

In a further example, the compound that inhibits G-CSF signaling reduces mobilization of hematopoietic stem cells and/or endothelial progenitor cells in vivo following G-CSF administration and/or reduces the number of neutrophils in vivo, e.g., following G-CSF administration (however this is not essential). For example, the compound that inhibits G-CSF signaling is administered, optionally before, at the time of or after administration of G-CSF or a modified form thereof (e.g., PEGylated G-CSF or filgrastim). The number of hematopoietic stem cells (e.g., expressing CD34 and/or Thy1) and/or endothelial progenitor cells (e.g., expressing CD34 and VEGFR2) and/or neutrophils (identified morphologically and/or expressing e.g., CD10, CD14, CD31 and/or CD88) is assessed. A compound that reduces the level of the cell(s) compared to the level observed in the absence of the compound is considered to neutralize G-CSF signaling. In one example, the compound that inhibits G-CSF signaling reduces the number of neutrophils without inducing neutropenia.

Other methods for assessing neutralization of G-CSF signaling are contemplated by the present disclosure.

Determining Effector Function

As discussed herein, some proteins of the present disclosure have reduced effector function. Methods for assessing ADCC activity are known in the art.

In one example, the level of ADCC activity is assessed using a $^{51}$Cr release assay, an europium release assay or a $^{35}$S release assay. In each of these assays, cells expressing G-CSFR are cultured with one or more of the recited compounds that inhibit G-CSF signaling for a time and under conditions sufficient for the compound to be taken up by the cell. In the case of a $^{35}$S release assay, cells expressing hG-CSFR can be cultured with $^{35}$S-labeled methionine and/or cysteine for a time sufficient for the labeled amino acids to be incorporated into newly synthesized proteins. Cells are then cultured in the presence or absence of the protein and in the presence of immune effector cells, e.g., peripheral blood mononuclear cells (PBMC) and/or NK cells. The amount of $^{51}$Cr, europium and/or $^{35}$S in cell culture medium is then detected, and little or no change in the presence of the protein compared to in the absence of protein (or a reduced level of the compound compared to the level observed in the presence of an anti-hG-CSFR antibody comprising a human IgG1 Fc) indicates that the protein has reduced effector function. Exemplary publications disclosing assays for assessing the level of ADCC induced by a protein include Hellstrom, et al. *Proc. Natl Acad. Sci. USA* 83:7059-7063, 1986 and Bruggemann, et al., *J. Exp. Med.* 166:1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, WI, USA).

C1q binding assays may also be carried out to confirm that the protein is able to bind C1q and may induce CDC. To assess complement activation, a CDC assay may be performed (see, for example, Gazzano-Santoro et al, *J. Immunol. Methods* 202: 163, 1996.

Determining Half Life

Some proteins encompassed by the present disclosure have an improved half-life, e.g., are modified to extend their half-life compared to proteins that are unmodified. Methods for determining a protein with an improved half-life will be apparent to the skilled person. For example, the ability of a protein to bind to a neonatal Fc receptor (FcRn) is assessed. In this regard, increased binding affinity for FcRn increased the serum half-life of the molecule (see for example, Kim et al., *Eur J Immunol.*, 24:2429, 1994).

The half-life of a protein of the disclosure can also be measured by pharmacokinetic studies, e.g., according to the method described by Kim et al, *Eur J of Immunol* 24:542, 1994. According to this method radiolabeled protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Prophylactic and/or Therapeutic Efficacy

The efficacy of a compound to treat or prevent a complication associated with sickle cell disease can be assessed by using a mouse model of sickle cell disease. For example, the mouse model is the Townes mouse as described in Ryan, Ciavatta and Townes, Knockout-Transgenic Mouse Model of Sickle Cell Disease, *Science*, 1997, vol. 278, pp 873-876.

Methods of assessing the therapeutic and/or prophylactic setting will be apparent to the skilled person and/or described herein.

Briefly, in a prophylactic setting, Townes sickle (SS) mice are treated with a compound of the disclosure or control via the tail vein (e.g., 10 mL/kg). In one example, the compound is administered 1 hour before inducing microvascular stasis with hemoglobin Hb or −168 hours (i.e., 7 days prior). Mice are implanted with a Dorsal Skin Fold Chamber (DSFC) at e.g., −45 minutes. Approximately 30 minutes after the start of DSFC implantation at −15 minutes, 20-25 flowing venules in the DSFC window may be selected and mapped using intravital microscopy. After baseline selection and mapping of flowing venules, at time 0, all mice are infused via the tail vein with human Hb in sterile saline (1 µmol/kg, 10 ml/kg) to induce microvascular stasis. The same vessels that are selected and mapped at baseline are re-examined for stasis (no flow) 1 hour after Hb infusion. The percent stasis (% venules with no flow) is calculated.

Briefly, in a therapeutic setting, Townes sickle (SS) mice are treated with a compound of the disclosure (e.g. at 10 mg/kg), mouse IgG isotype control (10 mg/kg) or vehicle via the tail vein (10 mL/kg). In one example, a mouse IgG isotype control antibody is used which has been previously shown to have no effect on vascular stasis (as described in Vercellotti et al 2019). For example, SS mice are implanted with a Dorsal Skin Fold Chamber (DSFC) at −45 minutes. Approximately 30 minutes after the start of DSFC implantation at −15 minutes, 20-25 flowing venules in the DSFC window are selected and mapped using intravital microscopy. After baseline selection and mapping of flowing venules, at time 0, all mice are infused via the tail vein with human Hb in sterile saline (1 µmol/kg, 10 ml/kg) to induce microvascular stasis. The compound is administered 30 minutes after inducing microvascular stasis with Hb (i.e., +0.5 h, because the VOC is considered at t=0). Total infusion volume (test article and Hb) is 20 ml/kg. The same vessels that are selected and mapped at baseline are re-examined for stasis (no flow) 2 hour after Hb infusion. The percent stasis (% venules with no flow) is calculated.

Compositions

In some examples, a compound as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques. In one example, the compound as described herein is administered subcutaneously.

Methods for preparing a compound into a suitable form for administration (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or subcutaneous administration or administration into a body cavity or lumen of an organ or joint. The compositions for administration will commonly comprise a solution of the compound that inhibits G-CSF signaling dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of compound of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, compounds of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver compounds of the present disclosure.

One skilled in the art would be able, by routine experimentation, to determine what an effective dose of the compound of the disclosure would be for the purpose of treating or preventing or delaying progression or reducing or inhibiting or hindering development of a complication associated with sickle cell disease in a subject suffering from sickle cell disease as described herein. For example, a therapeutically active amount of a compound may vary according to factors such as the disease stage, age, sex and weight of the subject, and the ability of the compound to elicit a desired response in the subject. The dosage regimen may be adjusted to provide the optimum therapeutic response. For example, the optimum therapeutic response may be a reduction in frequency of a symptom of a complication of sickle cell disease and/or hospitalisation associated with a complication of sickle cell disease. In one example, a method of the disclosure reduces the frequency of a symptom of a complication of sickle cell disease. For example, the method reduces the frequency of vaso-occlusive crisis episodes. In one example, a method of the disclosure reduces the frequency of hospitalisation associated with a complication of sickle cell disease.

In one example, several divided doses may be administered daily, or the dose may be proportionally reduced as indicated by the exigencies of the therapeutic situation. Generally, however, an effective dosage is expected to be in the range of about 1 to 200 mg/kg body weight. Furthermore, an effective dosage is expected to be administered at least one or more times, such as every 7-30 days, such as every 10-22 days, for example, every 10-15 days.

Administration of a compound according to the methods of the present disclosure can be continuous or intermittent, depending, for example, on the subject's physiological condition, whether the purpose of the administration is therapeutic or prophylactic, and other factors known to skilled practitioners. For example, the compound described herein may be administered prior to, during or after development of a complication as described herein, or pro re nata, In one example, the compound is administered pro re nata. For example, the compound is administered at the onset of a complication of sickle cell disease, or a symptom thereof. For example, at the onset of pain is associated with a vaso-occlusive crisis.

Combination Therapies

In one example, a compound of the present disclosure is administered in combination with an additional therapy useful for treating or preventing or delaying progression or reducing or inhibiting or hindering development of a disease or condition described herein, either as combined or additional treatment steps or as additional components of a therapeutic formulation.

In one example, the additional therapy may be a standard of care therapy for the complication associated with sickle cell disease, or it may be a standard of care therapy for the sickle cell disease itself.

Standard of care therapies for treatment of a complication associated with sickle cell disease will be apparent to the skilled person and/or are described herein.

In one example, the standard of care therapy is for the management of pain. For example, the standard of care therapy is for the management of acute or chronic pain. In one example, the pain is associated with a vaso-occlusive crisis and/or pain associated with acute chest syndrome. Exemplary therapies for the management of acute or chronic pain include, opioids, analgesics and nonsteroidal anti-inflammatory drugs (NSAIDs).

In one example, the additional therapy inhibits or reduces the expression or activity of one or more of:
 (i) E-selectin on endothelial cells;
 (ii) vascular cell adhesion molecule 1 (VCAM-1) on endothelial cells;
 (iii) intercellular adhesion molecule 1 (ICAM-1) on endothelial cells; and
 (iv) P-selectin on endothelial cells.

In one example, the compound that inhibits G-CSF signaling is administered simultaneously with the other compound.

In one example, the compound that inhibits G-CSF signaling is administered before the other compound.

In one example, the compound that inhibits G-CSF signaling is administered after the other compound.

In some examples, the compound that inhibits G-CSF signaling is administered in combination with a cell. In some examples, the cell is a stem cell, such as a mesenchymal stem cell.

In some examples, the compound that inhibits G-CSF signaling is administered in combination with a gene therapy.

Kits

Another example of the disclosure provides kits containing compounds useful for treating or preventing or delaying progression or reducing or inhibiting or hindering development of a complication associated with sickle cell disease as described above.

In one example, the kit comprises (a) a container comprising a compound that inhibits G-CSF signaling as described herein, optionally in a pharmaceutically acceptable carrier or diluent; and (b) a package insert with instructions for treating or preventing or delaying progression or reducing or inhibiting or hindering development of a complication associated with sickle cell disease in a subject suffering from sickle cell disease.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating the complication associated with sickle cell disease and may have a sterile access port (for example, the container may be an intravenous solution bag or a vial having a stopper pierceable by a hypodermic injection needle). At least one active agent in the composition is the compound that inhibits G-CSF signaling. The label or package insert indicates that the composition is used for treating or preventing or delaying progression or reducing or inhibiting or hindering development of a complication associated with sickle cell disease in a subject eligible for treatment, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The present disclosure includes the following non-limiting Examples.

EXAMPLES

Example 1: An Anti-GCSFR Antibody Inhibits G-CSF Signaling in a Mouse Model of Sickle Cell Disease VR81 is a mouse monoclonal IgG1κ antibody produced against the extracellular domain of murine G-CSFR and blocks G-CSF binding to G-CSFR as described (Campbell et al. *Journal of Immunology*, 197(11) (2016) 4392-4402). In this regard, VR81 is a mouse surrogate antibody for C1.2 and C1.2G described herein and in WO2012171057.

As shown in FIG. 1A, the PK of VR81 in a mouse model of sickle cell disease at 30 mg/kg is characterized by a flat concentration versus time profile with a long half-life (around 6 days).

At this dose the receptor occupancy (RO) and the inhibition of the receptor activity (phosphorylation of STAT3) by VR81 have been measured by flow cytometry. The full RO occupancy occurs within 5 minutes after administration, and is maintained for at least 1 week. Full receptor occupancy was also confirmed by the full pSTAT3 inhibition (FIGS. 1B and C).

Example 2: Inhibition of G-CSF Signaling in a Mouse Model of Sickle Cell Disease Prevents Vascular Stasis The effect of administration of an anti-G-CSFR antibody on vascular stasis in a mouse model of sickle cell disease was assessed.

Townes sickle (SS) mice (n=4/group, 12-20 weeks of age) were treated with an anti-mouse G-CSFR antibody (Ch5E2-VR81-mIgG1κ; VR81; 30 mg/kg), a positive control anti-murine P selectin (anti-Psel; 1.2 mg/kg) or vehicle control (10 mL/kg) via the tail vein.

Figure 2:
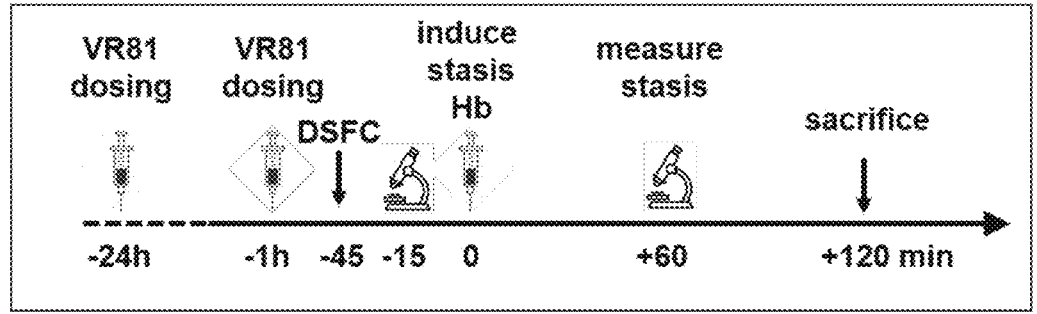
FIG. 2 is a series of graphical representations showing (A) schematic of experimental methodology and (B) efficacy of VR81 in Townes sickle mice by reduction in vascular stasis.
Figure 2:
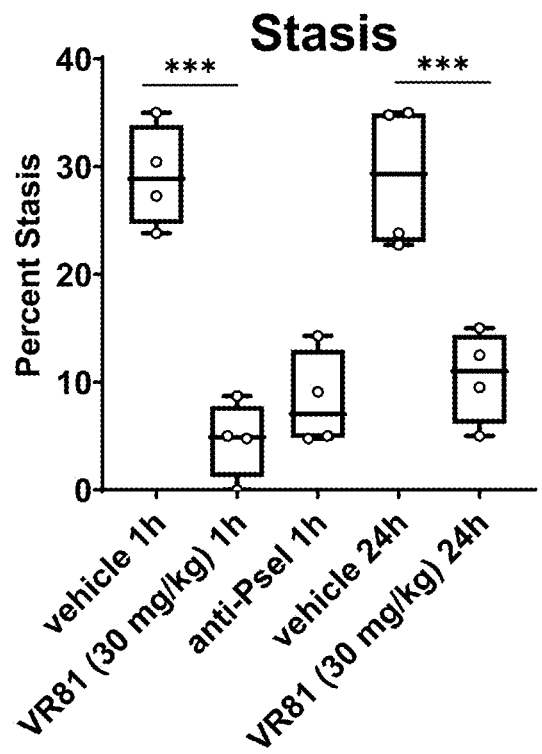

A summary of the methodology is provided in FIG. 2A and Table 1. Briefly, in groups 1, 2 and 3 the test article was administered 1 hour before inducing microvascular stasis (VOC) with hemoglobin (Hb; i.e. −1 h, because the VOC was considered at t=0). In groups 4 and 5, the test article was administered at −24 hours. All SS mice were implanted with a Dorsal Skin Fold Chamber (DSFC) at −45 minutes. Approximately 30 minutes after the start of DSFC implantation at −15 minutes, 20-25 flowing venules in the DSFC window were selected and mapped using intravital microscopy. After baseline selection and mapping of flowing venules, at time 0, all mice were infused via the tail vein with human Hb in sterile saline (1 μmol/kg, 10 ml/kg) to induce microvascular stasis. Total infusion volume (test article and Hb) was 20 ml/kg. The same vessels that were selected and mapped at baseline were re-examined for stasis (no flow) 1 hour after Hb infusion and the percent stasis (% venules with no flow) was calculated. At the time of the terminal blood collection (+2 hours), the mice were sacrificed in a $CO_2$ chamber and blood was collected from the heart. Two additional control groups were treated with vehicle (6, 7) without VOC trigger.

Terminal blood was collected and placed on ice. Blood samples were divided into two aliquots. One aliquot was used for whole blood analyses and the other for serum separation. The following parameters were measured in whole blood: Complete blood cell (CBC) and differential white blood cell (WBC) counts, including neutrophils, monocytes, and lymphocytes; neutrophil activation markers by flow cytometry including CD11b, CD16 and CD66b to identify highly enriched neutrophils and CD62L (L-selectin) and CD64 (FcγRI) activation markers.

Liver, lungs, kidneys and spleen were collected, weighed and divided into two aliquots. One piece of tissue was put in formalin and the other piece was snap frozen in liquid $N_2$ and stored at −85° C. Formalin-aliquots were processed and stained for neutrophil infiltration and vessel congestion. Frozen aliquots of liver, kidneys, and spleen were analyzed for protein expression. Nuclear extracts and microsomal subfractions were isolated and Western blots of these subfractions were run to measure relative expression of proteins of interest, e.g. nuclear NF-κB total and phospho-p65 (NF-kB activation) and Nrf2 and microsomal VCAM-1, ICAM-1, E-selectin, and HO-1.

TABLE 1

Methodology

| Group | N | DSFC implantation time (with respect to VOC) | Test Article (TA) | TA dose (mg/kg) | VOC trigger (t = 0) | TA dosing time (with respect to VOC) | Stasis Measurement (with respect to VOC) | Blood sampling time (with respect to VOC) |
|---|---|---|---|---|---|---|---|---|
| 1 | 4 | −45 min | VR81 | 30 | Hb* | −1 h | +1 h | +2 h |
| 2 | 4 | −45 min | anti-Psel | 1.2 | Hb* | −1 h | +1 h | +2 h |
| 3 | 4 | −45 min | vehicle | — | Hb* | −1 h | +1 h | +2 h |
| 4 | 4 | −45 min | VR81 | 30 | Hb* | −24 h | +1 h | +2 h |
| 5 | 4 | −45 min | vehicle | — | Hb* | −24 h | +1 h | +2 h |
| 6 | 4 | −45 min | vehicle | — | — | — | — | — |
| 7 | 4 | No DSFC | vehicle | — | — | — | — | — |

*= 1 μmol/kg;
TA = test article

As shown in FIG. 2B, the efficacy at 1 h after VR81 administration at 30 mg/kg appears similar to, or slightly better than, administration of the anti-Psel antibody positive control (at 1.2 mg/kg). The efficacy has a fast onset (just 1 h after administration) and is prolonged (at least 24 h after single administration).

No statistically significant changes were observed in the absolute neutrophil count (ANC), red blood cell count (RBC), hematocrit (HCT) and total blood hemoglobin concentration (Hb) (data not shown).

Example 3: Inhibition of G-CSF Signaling in a Mouse Model of Sickle Cell Disease Prevents Vascular Stasis Following Hypoxia and Re-Oxygenation The efficacy of an anti-GCSFR antibody versus a positive control (an anti-Psel antibody) was assessed with a different VOC trigger (H/R, Hypoxia/Re-oxygenation).

Townes sickle (SS) mice (n=4/group, 12-20 weeks of age) were treated with VR81 (30 mg/kg), a positive control anti-Psel antibody (1.2 mg/kg) or vehicle only control (10 mL/kg) via the tail vein.

Figure 3:
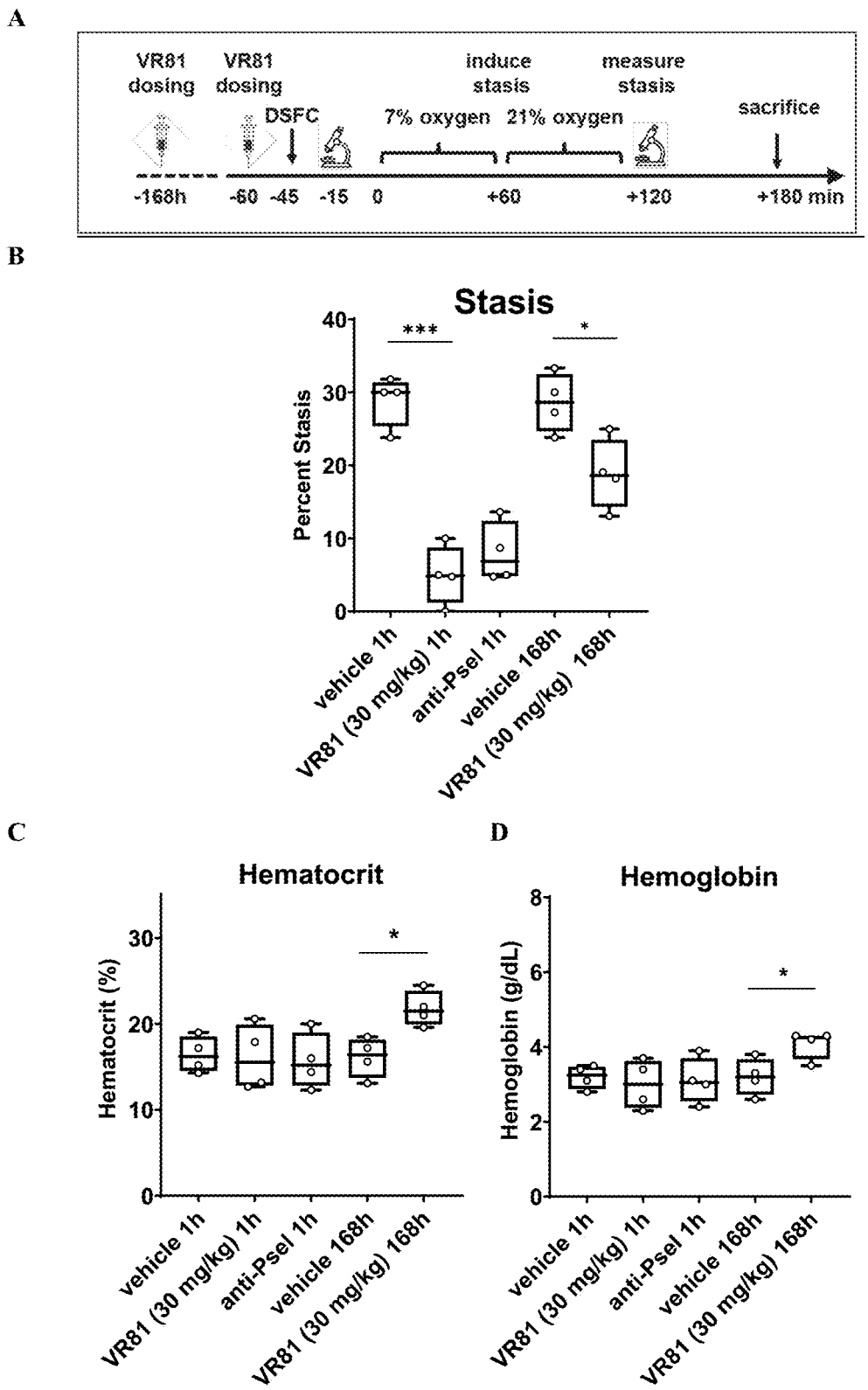
FIG. 3 is a series of graphical representations showing (A) schematic of experimental methodology and (B) efficacy of VR81 in Townes sickle mice by reduction in vascular stasis. A statistically significant increase was observed in (C) hematocrit (HCT) and (D) total blood hemoglobin concentration (Hb) at 1 week after VR81 administration.

A summary of the methodology is provided in FIG. 3A and Table 2. Briefly, in groups 1, 2 and 3 the test article was administered 1 hour before inducing microvascular stasis with Hypoxia/Re-oxygenation (i.e. −1 h, because the VOC was considered at t=0), while in groups 4 and 5, the test article was administered at −168 hours (−7 days). All SS mice were implanted with a Dorsal Skin Fold Chamber (DSFC) at −45 minutes. Approximately 30 minutes after the start of DSFC implantation at −15 minutes, 20-25 flowing venules in the DSFC window were selected and mapped using intravital microscopy. After baseline selection and mapping of flowing venules, at time 0, all mice were subjected to 7% $O_2$ (hypoxia) for 1 hour followed by room air (re-oxygenation) for 2 hours to induce microvascular stasis. The same vessels that were selected and mapped at baseline were re-examined for stasis (no flow) 1 hour after hypoxia/re-oxygenation. The percent stasis (% venules with no flow) was calculated. At the time of the terminal blood collection (+3 hours), the mice were sacrificed in a $CO_2$ chamber and blood was collected from the heart.

Terminal blood, liver, lungs, kidneys and spleen were collected and treated as described in Example 2.

TABLE 2

Methodology

| Group | N | DSFC implantation time (with respect to VOC) | Test Article (TA) | TA dose (mg/kg) | VOC trigger (t = 0) | TA dosing time (with respect to start of hypoxia) | Stasis Measurement (with respect to start of hypoxia) | Blood sampling time (with respect to start of hypoxia) |
|---|---|---|---|---|---|---|---|---|
| 1 | 4 | −45 min | VR81 | 30 | H/R* | −1 h | +2 h | +3 h |
| 2 | 4 | −45 min | anti-Psel | 1.2 | H/R* | −1 h | +2 h | +3 h |
| 3 | 4 | −45 min | vehicle | — | H/R* | −1 h | +2 h | +3 h |
| 4 | 4 | −45 min | VR81 | 30 | H/R* | −168 h | +2 h | +3 h |
| 5 | 4 | −45 min | vehicle | — | H/R* | −168 h | +2 h | +3 h |

*= 1 h at 7% oxygen;
TA = test article

Similar to the results in Example 1, the efficacy at 1 h after VR81 administration at 30 mg/kg appears similar to the anti-Psel positive control (or slightly better) (FIG. 3B). The efficacy at 1 h after VR81 administration at 30 mg/kg appears similar to the efficacy observed with the Hb VOC trigger.

The efficacy has a fast onset (just 1 h after administration) and is prolonged (at least 1 week after single administration), but the efficacy observed for Group 4 (VR81 administered 1 week before VOC trigger) appeared lower than that observed in Group 1 (VR81 administered 1 h before VOC trigger).

No statistically significant changes were observed in the absolute neutrophil count (ANC) or red blood cell count (RBC) (data not shown). A statistically significant increase was observed in hematocrit (HCT) and total blood hemoglobin concentration (Hb) at 1 week after VR81 administration (FIGS. 3C and 3D).

Example 4: Prevention of Vascular Stasis in a Mouse Model of Sickle Cell Disease with an Inhibitor of G-CSF Signaling has Fast Onset and is Prolonged The time-dependence of efficacy of VR81 was assessed.

Townes sickle (SS) mice (n=4/group, 12-20 weeks of age) were treated with VR81 (30 mg/kg or 10 mg/kg) or vehicle only via the tail vein (10 mL/kg).

Figure 4:
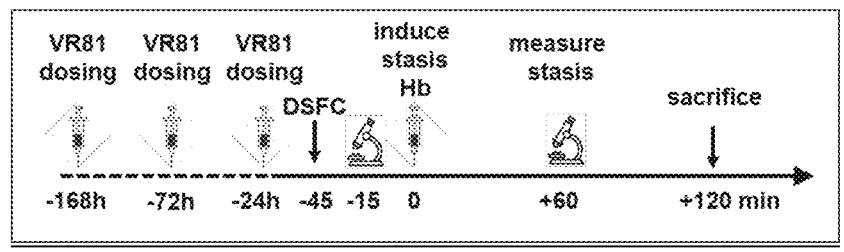
FIG. 4 is a series of graphical representations showing (A) schematic of experimental methodology and (B) efficacy of VR81 in Townes sickle mice by reduction in vascular stasis. (C) Less neutrophil infiltration was observed in the liver and (D) down-regulation of cell adhesion protein P-selectin was observed in the lung 7 days after VR81 administration at 30 mg/kg and 1 and 3 days after VR81 administration at 10 mg/kg. Strong down-regulation of cell adhesion proteins (E) VCAM-1, (F) ICAM-1, (G) E-Selectin and (H) nuclear factor NF-kB and (I) enzyme HO-1 and (J) nuclear factor NRF-2 was observed and in liver at 7 days after VR81 administration at 30 mg/kg and at 1, 3 and 7 days after VR81 administration at 10 mg/kg.
Figure 4:
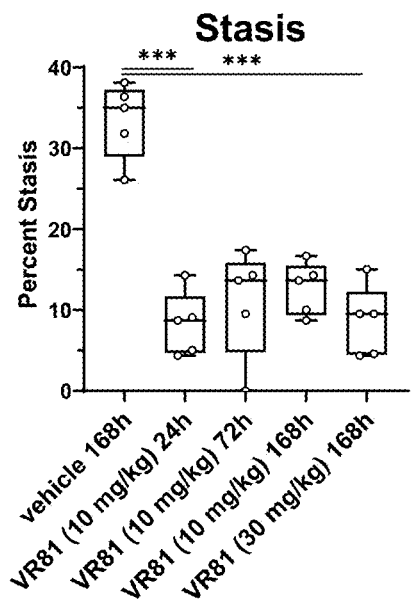
Figure 4:
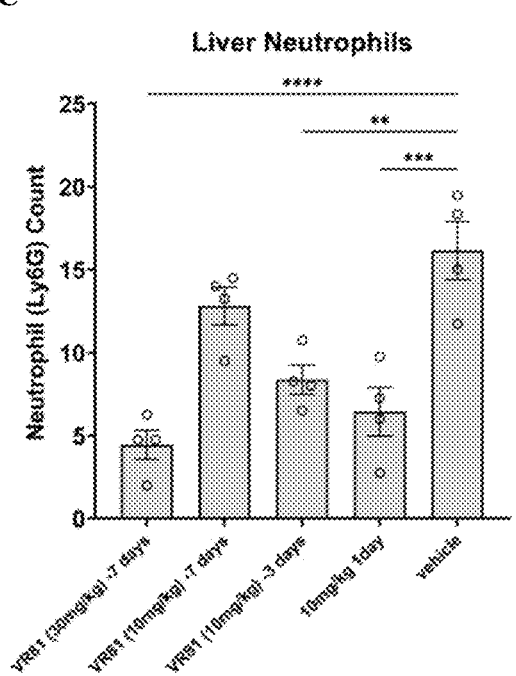
Figure 4:
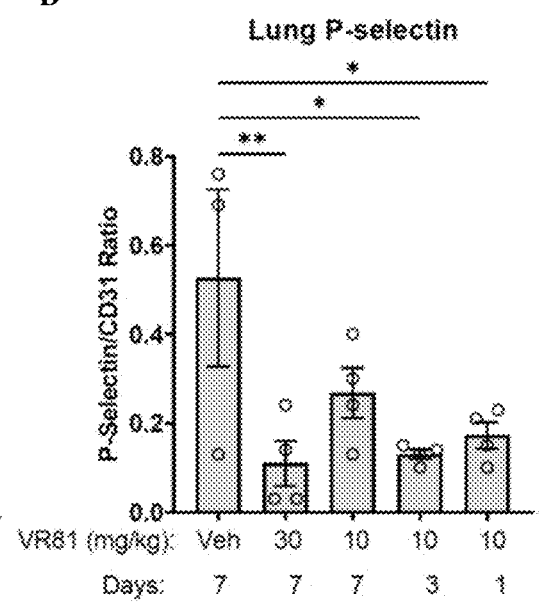
Figure 4:
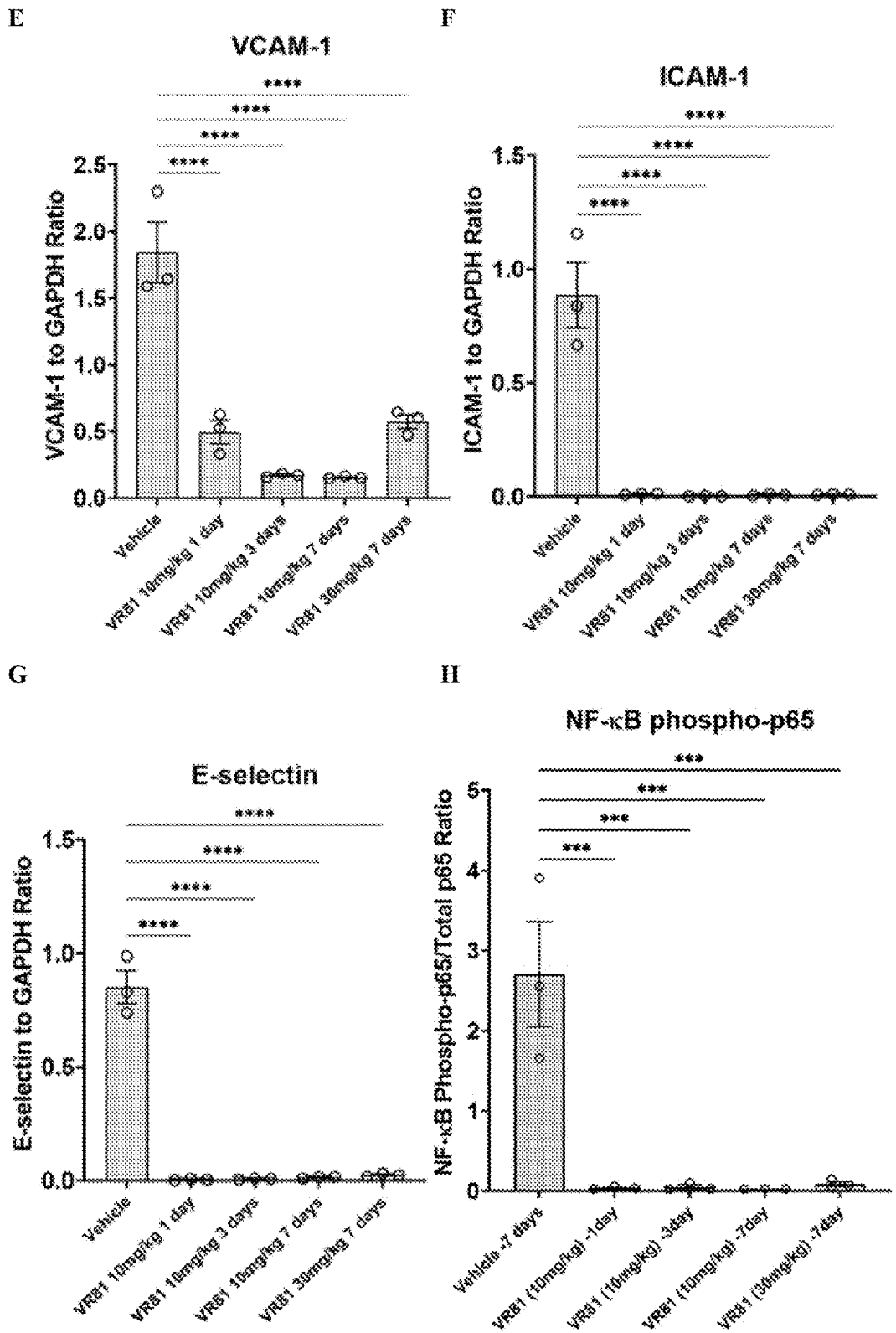
Figure 4:
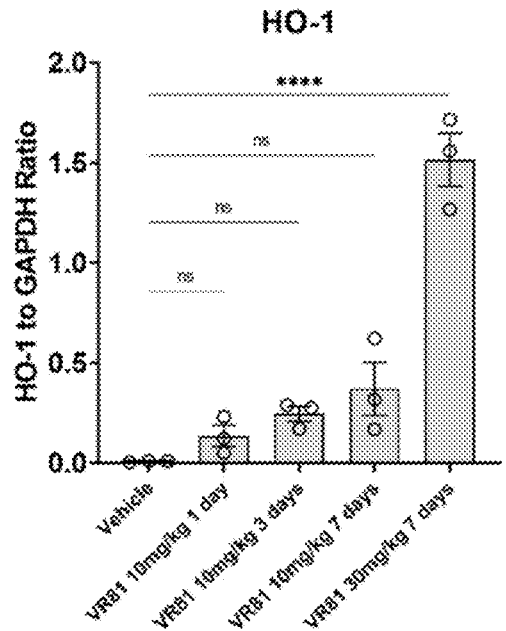
Figure 4:
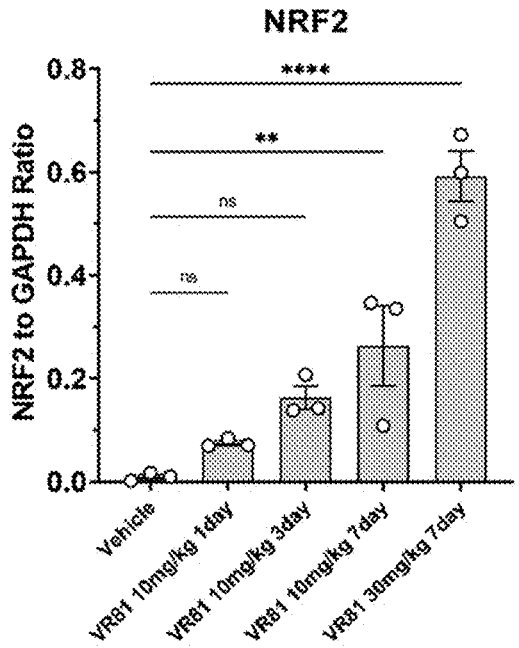

A summary of the methodology is provided in FIG. 4A and Table 3. Briefly, in groups 1, 2 and 5 test article was administered 168 hours before inducing microvascular stasis with Hb (i.e. −168 h, because the VOC was considered at t=0), while in groups 3 and 4 test article was administered at −72 and 24 hours, respectively. All SS mice were implanted with a Dorsal Skin Fold Chamber (DSFC) at −45 minutes. Approximately 30 minutes after the start of DSFC implantation at −15 minutes, 20-25 flowing venules in the DSFC window were selected and mapped using intravital microscopy. After baseline selection and mapping of flowing venules, at time 0, all mice were infused via the tail vein with human Hb in sterile saline (1 μmol/kg, 10 ml/kg) to induce microvascular stasis. Total infusion volume (test article and Hb) was 20 ml/kg. The same vessels that were selected and mapped at baseline were re-examined for stasis (no flow) 1 hour after Hb infusion and the percent stasis (% venules with no flow) was calculated. At the time of the terminal blood collection (+2 hours), the mice were sacrificed in a CO2 chamber and blood was collected from the heart.

Terminal blood, liver, lungs, kidneys and spleen were collected and treated as described in Example 2.

As shown in FIG. 4B, the efficacy appears the same with VR81 at 10 and 30 mg/kg. The efficacy has a fast onset (just 24 h after administration) and is prolonged (at least 1 week after single administration).

No statistically significant changes were observed in the absolute neutrophil count (ANC), red blood cell (RBC) count, hematocrit (HCT) and total blood hemoglobin concentration (Hb) (data not shown).

Less neutrophil infiltration was observed in liver at 7 days after VR81 administration at 30 mg/kg and at 1 and 3 days after VR81 administration at 10 mg/kg (FIG. 4C).

Down-regulation of cell adhesion protein P-selectin was observed in the lung 7 days after VR81 administration at 30 mg/kg and 1 and 3 days after VR81 administration at 10 mg/kg (FIG. 4D). No statistical difference was observed for von Willebrand Factor (vWF) (data not shown).

Strong down-regulation of cell adhesion proteins ICAM-1, VCAM-1, E-Selectin and nuclear factor NF-kB was observed in liver 7 days after VR81 administration at 30 mg/kg and at 1, 3 and 7 days after VR81 administration at 10 mg/kg (FIG. 4E-H).

Strong up-regulation of enzyme HO-1 and nuclear factor NRF2 was observed in liver at 7 days after VR81 administration at 30 mg/kg and at 1, 3 and 7 days after VR81 administration at 10 mg/kg (FIG. 4I-J).

Example 5: Inhibition of Vascular Stasis by Inhibition of G-CSF Signaling is Dose-Dependent The dose-dependency of the response was assessed Townes sickle (SS) mice (n=4/group, 12-20 weeks of age) were treated with VR81 (0.1 mg/kg, 1 mg/kg or 10 mg/kg) or vehicle via the tail vein (10 mL/kg).

Figure 5:
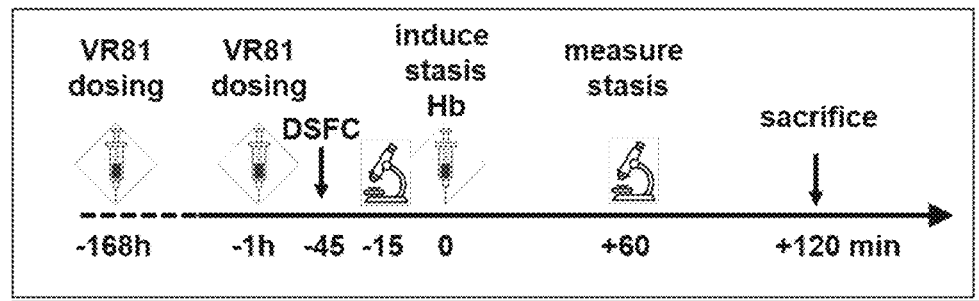
FIG. 5 is a series of graphical representations showing (A) schematic of experimental methodology and (B) efficacy of VR81 in Townes sickle mice by reduction in vascular stasis. No statistically significant changes were observed in (C)-(D) absolute neutrophil count (ANC), (E) red blood cell count (RBC), (F) hematocrit (HCT) and (G) total blood hemoglobin concentration (Hb). (H)-(I) Less neutrophil infiltration, and down-regulation of (J)-(K) cell adhesion protein P-selectin and (L)-(M) von Willebrand Factor was observed in liver 7 days after VR81 administration.
Figure 5:
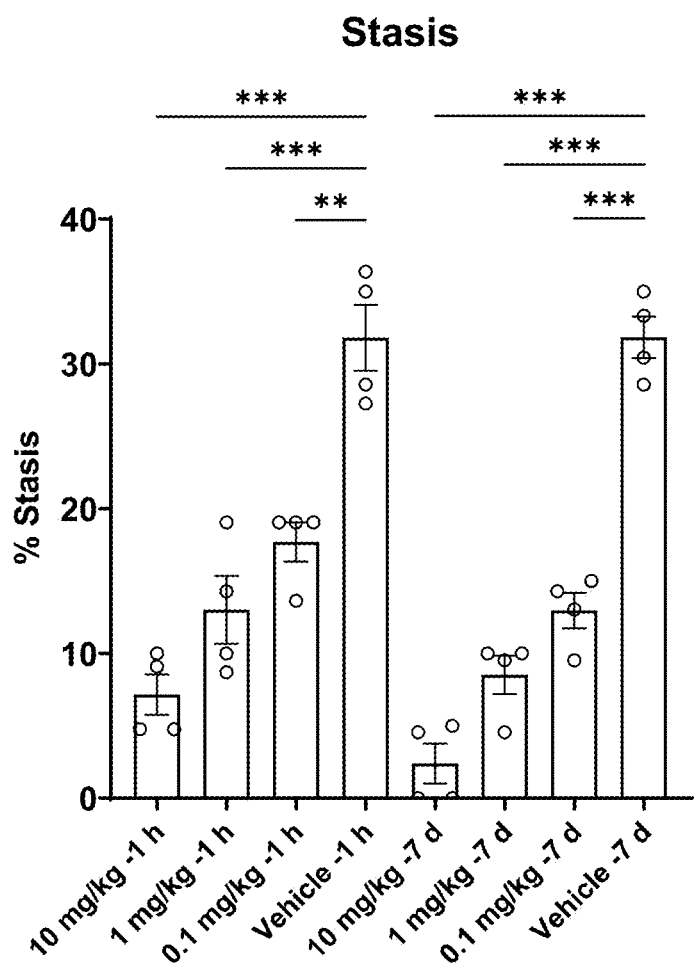
Figure 5:
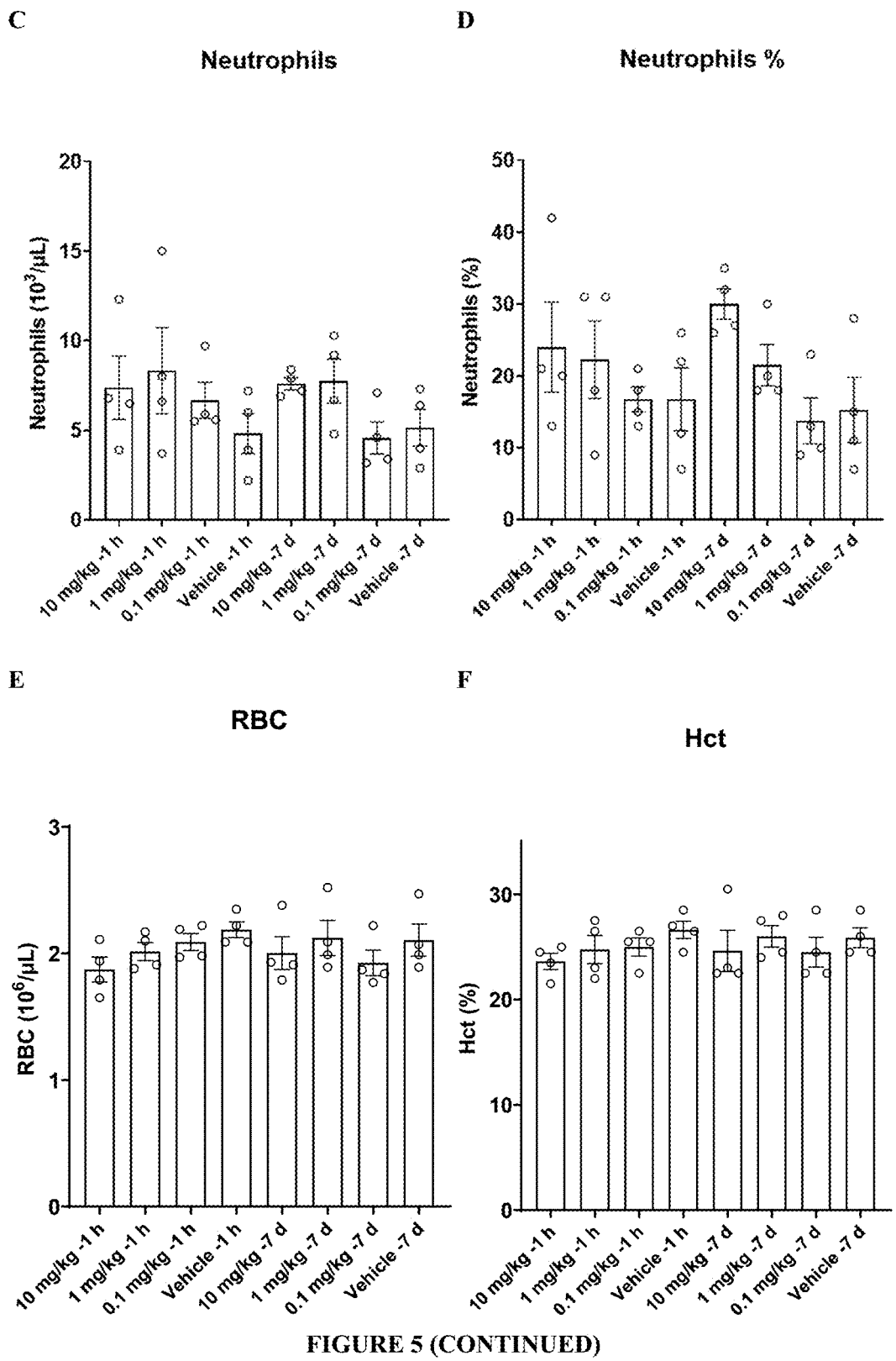
Figure 5:
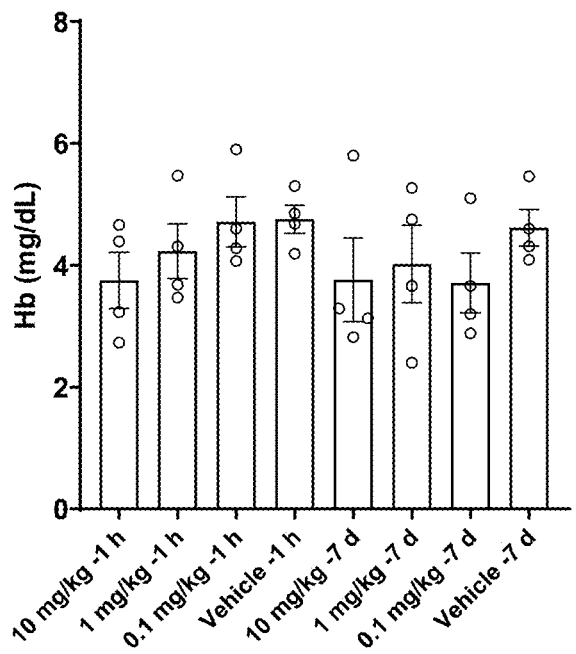
Figure 5:
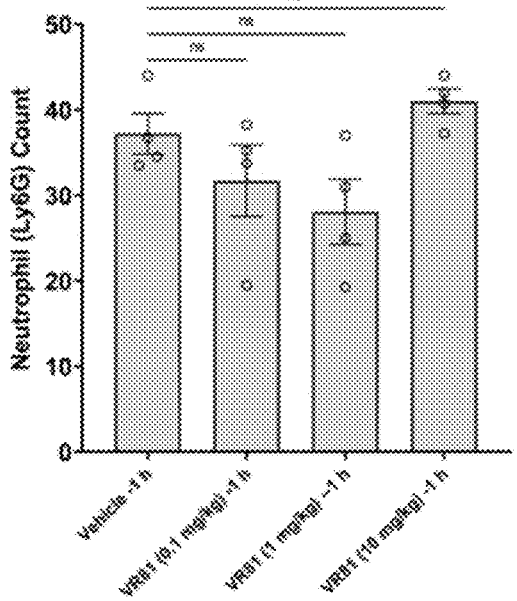
Figure 5:
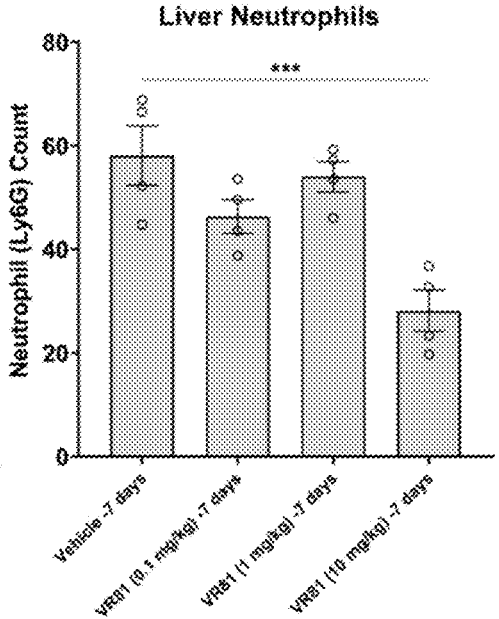
Figure 5:
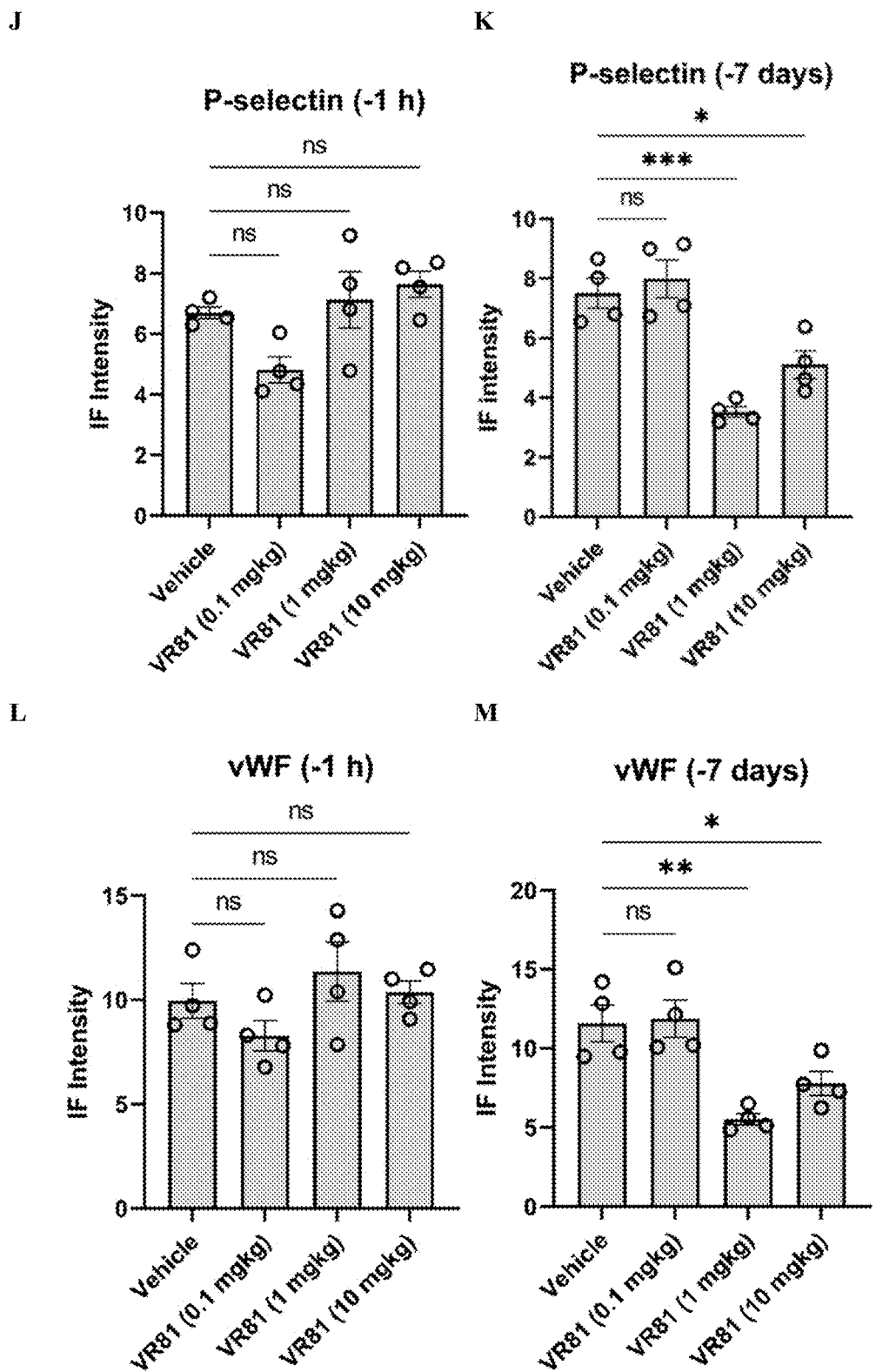

A summary of the methodology is provided in FIG. 5A and Table 4. Briefly, in groups 1, 2, 3 and 4, the test article was administered 1 hour before inducing microvascular stasis with Hb (i.e. −1 h, because the VOC was considered at t=0), while in groups 5, 6, 7 and 8, the test article was administered at −168 hours. All SS mice were implanted with a Dorsal Skin Fold Chamber (DSFC) at −45 minutes. Approximately 30 minutes after the start of DSFC implantation at −15 minutes, 20-25 flowing venules in the DSFC window were selected and mapped using intravital microscopy. After baseline selection and mapping of flowing venules, at time 0, all mice were infused via the tail vein with human Hb in sterile saline (1 μmol/kg, 10 ml/kg) to induce microvascular stasis. Total infusion volume (test article and Hb) was 20 ml/kg. The same vessels that were selected and mapped at baseline were re-examined for stasis (no flow) 1 hour after Hb infusion and the percent stasis (% venules with

TABLE 3

Methodology

| Group | N | DSFC implantation time (with respect to VOC) | Test Article (TA) | TA dose (mg/kg) | VOC trigger (t = 0) | TA dosing time (with respect to VOC) | Stasis Measurement (with respect to VOC) | Blood sampling time (with respect to VOC) |
|---|---|---|---|---|---|---|---|---|
| 1 | 4 | −45 min | VR81 | 30 | Hb* | −168 h | +1 h | +2 h |
| 2 | 4 | −45 min | VR81 | 10 | Hb* | −168 h | +1 h | +2 h |
| 3 | 4 | −45 min | VR81 | 10 | Hb* | −72 h | +1 h | +2 h |
| 4 | 4 | −45 min | VR81 | 10 | Hb* | −24 h | +1 h | +2 h |
| 5 | 4 | −45 min | vehicle | — | Hb* | −168 h | +1 h | +2 h |

*= 1 μmol/kg;
TA = test article no flow) was calculated. At the time of the terminal blood collection (+2 hours), the mice were sacrificed in a $CO_2$ chamber and blood was collected from the heart.

Terminal blood was collected and placed on ice. Blood samples were divided in two aliquots. One aliquot was used for whole blood analyses and the other aliquot for serum separation. The following parameters were measured in whole blood: CBC and differential WBC counts, including neutrophils, monocytes, and lymphocytes; Neutrophil activation markers by flow cytometry including CD11b, CD16 and CD66b to select for highly enriched neutrophils and CD62L (L-selectin) and CD64 (FcγRI) to select activation markers.

Liver, lungs, kidneys and spleen were collected, weighed and divided in two aliquots. One smaller piece of tissue was put in formalin and the other aliquot was flash frozen in liquid $N_2$ and then stored at $-85°$ C. Formalin-aliquots were processed and stained for neutrophil infiltration and vessel congestion. Frozen aliquots of liver, kidneys, and spleen were analyzed for protein expression. Nuclear extracts and microsomal subfractions were isolated and Western blots of these subfractions were run to measure relative expression of proteins of interest, e.g. nuclear NF-κB total and phospho-p65 (NF-kB activation) and Nrf2 and microsomal VCAM-1, ICAM-1, E-selectin, and HO-1.

Less neutrophil infiltration was observed in liver only 7 days after VR81 administration (FIG. 5H-I).

Down-regulation of cell adhesion proteins P-selectin and von Willebrand Factor (vWF) was observed in lung only 7 days after VR81 administration (FIG. 5J-M).

Example 6: Treatment of Vascular Stasis by Inhibition of G-CSF Signaling

The therapeutic effect of administration of an anti-G-CSFR antibody on vascular stasis in a mouse model of sickle cell disease is assessed.

Townes sickle (SS) mice (n=4/group, 12-20 weeks of age) are treated with VR81 (10 mg/kg), mouse IgG isotype control (10 mg/kg) or vehicle only via the tail vein (10 mL/kg). The mouse IgG isotype control antibody has been previously shown to have no effect on vascular stasis (as described in Vercellotti et al 2019).

Figure 6:
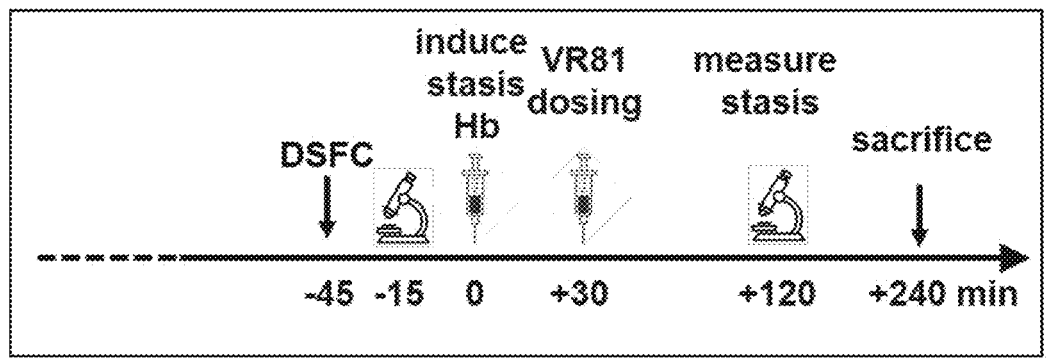
FIG. 6 is a schematic of the therapeutic experimental methodology.

A summary of the methodology is provided in FIG. 6 and Table 5. Briefly, all SS mice are implanted with a Dorsal Skin Fold Chamber (DSFC) at −45 minutes. Approximately 30 minutes after the start of DSFC implantation at −15 minutes, 20-25 flowing venules in the DSFC window are selected and mapped using intravital microscopy. After baseline selection and mapping of flowing venules, at time

TABLE 4

Methodology

| Group | N | DSFC implantation time (with respect to VOC) | Test Article (TA) | TA dose (mg/kg) | VOC trigger (t = 0) | TA dosing time (with respect to VOC) | Stasis Measurement (with respect to VOC) | Blood sampling time (with respect to VOC) |
|---|---|---|---|---|---|---|---|---|
| 1 | 4 | −45 min | VR81 | 10 | Hb* | −1 h | +1 h | +2 h |
| 2 | 4 | −45 min | VR81 | 1 | Hb* | −1 h | +1 h | +2 h |
| 3 | 4 | −45 min | VR81 | 0.1 | Hb* | −1 h | +1 h | +2 h |
| 4 | 4 | −45 min | vehicle | — | Hb* | −1 h | +1 h | +2 h |
| 5 | 4 | −45 min | VR81 | 10 | Hb* | −168 h | +1 h | +2 h |
| 6 | 4 | −45 min | VR81 | 1 | Hb* | −168 h | +1 h | +2 h |
| 7 | 4 | −45 min | VR81 | 0.1 | Hb* | −168 h | +1 h | +2 h |
| 8 | 4 | −45 min | vehicle | — | Hb* | −168 h | +1 h | +2 h |

*= 1 μmol/kg;

TA = test article

As shown in FIG. 5B, the efficacy appeared to be dose-dependent at both dosing times (i.e. the stasis percentage decreased with an increasing dose of VR81 (0.1, 1, 10 mg/kg). The efficacy had a fast onset (just 1 h after administration) and was prolonged (at least 1 week after single administration). The efficacy appeared to be time-dependent: i.e. a stronger inhibitory effect on stasis was observed in those mice that were dosed with VR81 1 week before the VOC trigger compared to the equivalent dose group dosed with VR81 one hour before the VOC trigger.

No statistically significant changes were observed in the absolute neutrophil count (ANC), red blood cell count (RBC), hematocrit (HCT) and total blood hemoglobin concentration (Hb) (FIG. 5C-G).

0, all mice are infused via the tail vein with human Hb in sterile saline (1 μmol/kg, 10 ml/kg) to induce microvascular stasis. The test article is administered 30 minutes after inducing microvascular stasis with Hb (i.e., +0.5 h, because the VOC is considered at t=0). Total infusion volume (test article and Hb) is 20 ml/kg. The same vessels that are selected and mapped at baseline are re-examined for stasis (no flow) 2 hour after Hb infusion and the percent stasis (% venules with no flow) is calculated. At the time of the terminal blood collection (+4 hours), the mice are sacrificed in a $CO_2$ chamber and blood is collected from the heart.

Terminal blood, liver, lungs, kidneys and spleen are collected and treated as described in Example 2.

TABLE 5

| | | | | | | TA dosing | | Blood sampling |
| | | DSFC implantation time | Test | TA | VOC | time (with | Stasis Measurement | time (with |
| | | (with respect | Article | dose | trigger | respect | (with respect | respect |
| Group | N | to VOC) | (TA) | (mg/kg) | (t = 0) | to VOC) | to VOC) | to VOC) |
|---|---|---|---|---|---|---|---|---|
| 1 | 4 | −45 min | VR81 | 10 | Hb* | +0.5 h | +2 h | +4 h |
| 2 | 4 | −45 min | Isotype control | 10 | Hb* | +0.5 h | +2 h | +4 h |
| 3 | 4 | −45 min | Vehicle control | — | Hb* | +0.5 h | +2 h | +4 h |

*= 1 μmol/kg;
TA = test article

Example 7: Upregulated G-CSF-Driven Gene Signature During VOC and Other Complications in SCD The inventors derived a gene signature of G-CSF activity using the transcriptomic data generated from peripheral samples collected from the first in-human clinical trial with CSL324, the CSL324_1001 (ACTRN12616000846426), a single-dose ascending and repeated dose, randomized, double-blind, placebo-controlled study to assess the safety, pharmacokinetics and pharmacodynamics of CSL324 in healthy adult subjects. The description of the generation of the blood transcriptome dataset was published in Gamell et al., 2023. The key features of this signature included being representative of G-CSF stimulation and compatibility with signature enrichment algorithms. The signature was derived from genes that were differentially expressed (adjusted p-value <0.05 and |log 2 fold-change|>2) at Day 3 (postfilgrastim/G-CSF) vs Pre-Treatment in the placebo group. This gene list was subsequently filtered to remove: (a) genes that were lowly expressed (log 2(counts)<0), (b) genes that were downregulated (to focus on upregulated genes only), and (c) non-protein-coding genes. The resulting gene signature, named the "In-house G-CSF gene signature" or "G-CSF gene signature", contains a total of 239 genes.

Blood transcriptome data from the following three datasets was assessed for enrichment of the G-CSF gene signature, including:
  GSE53441: PBMC microarray data from 10 healthy subjects and 24 SCD patients (Van Beers et al., Circ Res. 2015 Jan. 16; 116(2):298-306).
  GSE139912 (paired): Whole blood RNA-seq data from 33 SCD children at baseline & progressing to acute chest syndrome (ACS)/vaso-occlusive crisis (VOC) (Creary et al., Scientific Reports 2020, volume 10, Article number: 9013).
  GSE35007: Whole blood microarray data of 311 children (Quinlan et al., Front Genet. 2014 Feb. 14:5:26) split into:
    healthy controls (n=61)
    acute SCD events, e.g. VOC (n=36)
    newly enrolled SCD patients (steady-state base-line, n=134)
    followed Up SCD patients (return to base-line, n=80)

Raw expression data and metadata were retrieved from GEO (Edgar et al., Nucleic Acids Res. 2002 Jan. 1; 30 (1): 207-10) with the R (version 4.2.0) package 'GEOquery', version 2.66.0 (Davis S, Meltzer P, Bioinformatics, Volume 23, Issue 14, July 2007, Pages 1846-1847) and base-2 log-transformed using the GEO2R R scripts for RNA-Seq or microarray data (www.ncbi.nlm.nih.gov, accessed 8 Apr. 2024). Hereafter, sample-level gene set enrichment was performed using methods implemented in the R statistical software package 'GSVA' version 1.46.0 (Haenzelmann et al., BMC Bioinformatics volume 14, Article number: 7 (2013)), namely Gene Set Variation Analysis (GSVA; as described in Haenzelmann et al., BMC Bioinformatics volume 14, Article number: 7 (2013)) and single sample Gene Set Enrichment Analysis (ssGSEA; as described in Barbie et al., Nature. 2009 Nov. 5; 462 (7269): 108-112), both with default settings, except the use of no cross-sample normalization in ssGSEA. Since GSE139912 is RNA-Seq data, TPM values (transcript per million, Zhao et al., Journal of Translational Medicine volume 19, Article number: 269 (2021)), derived with median transcript lengths of genes, were used for the enrichment analysis.

Figure 7:
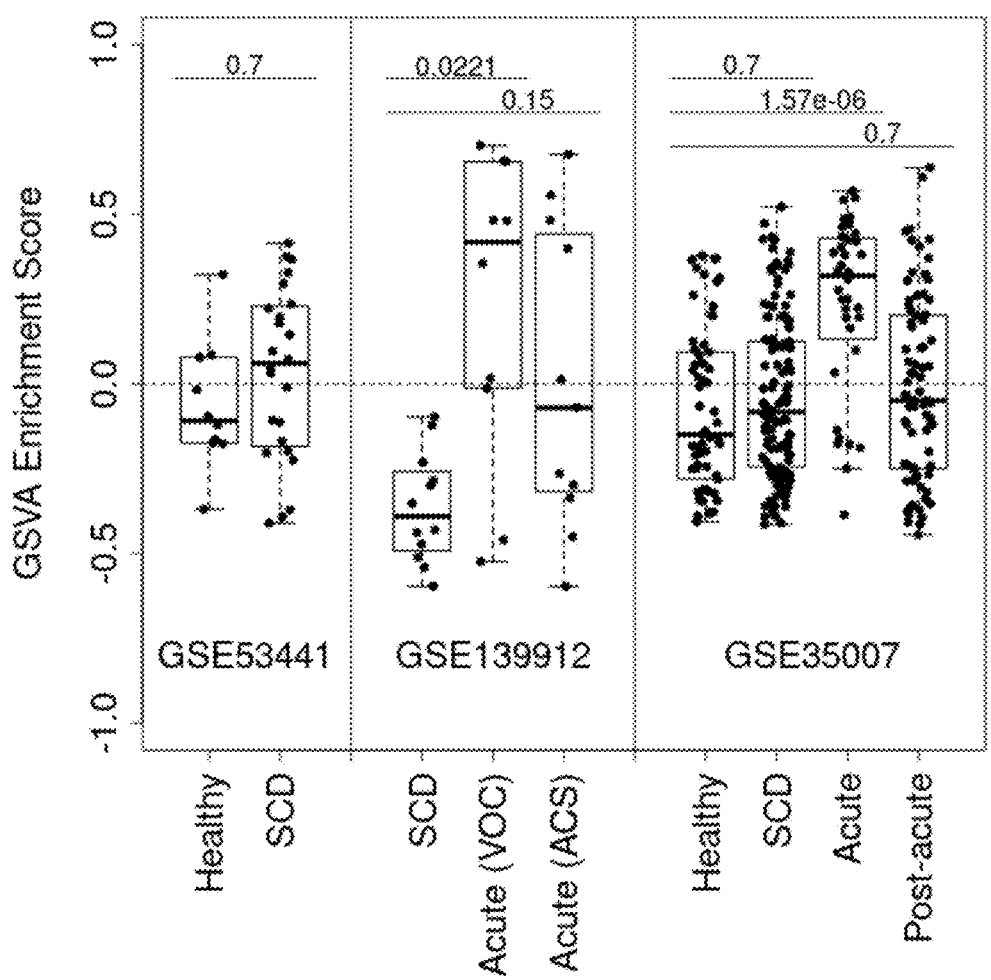
FIG. 7 is a series of graphical representations showing that the G-CSF RNA gene expression signature is elevated in acute SCD samples using (A) GSVA enrichment and (B) ssGSEA enrichment.
Figure 7:
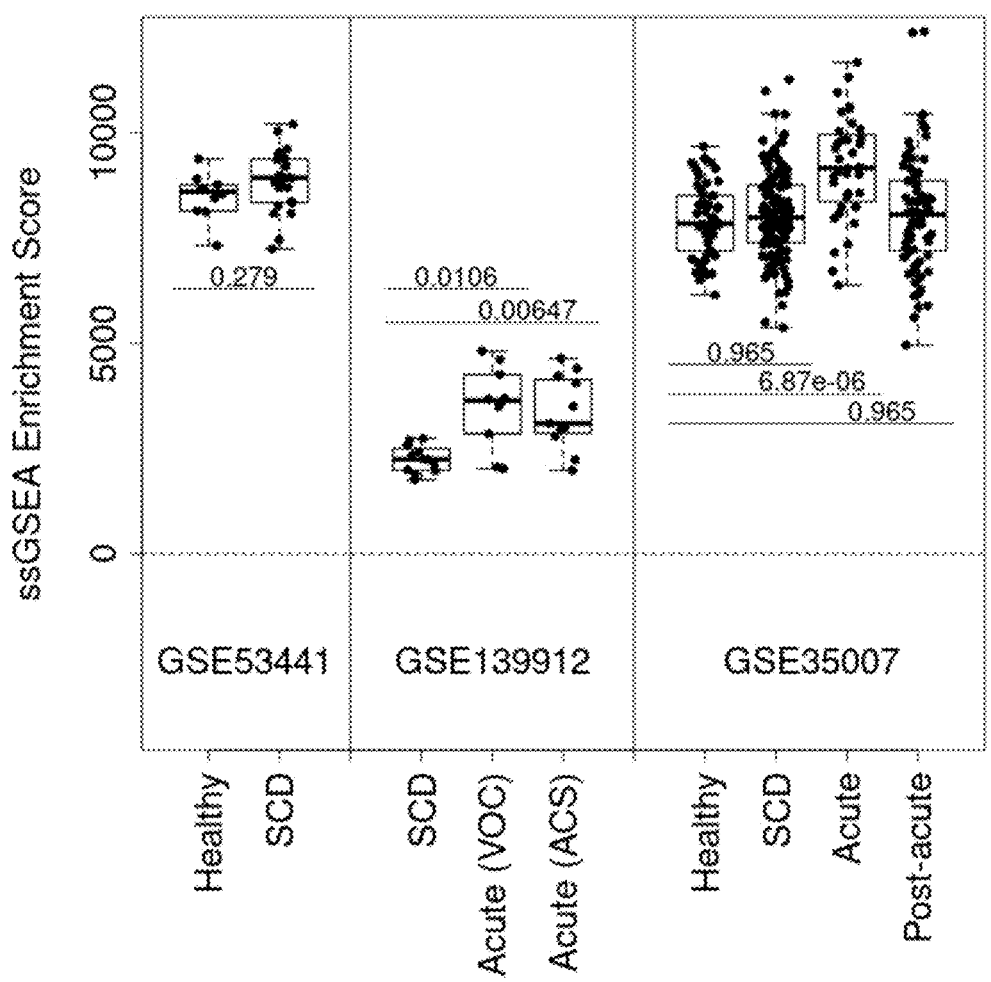

As shown in FIG. 7, the G-CSF gene signature was significantly elevated from high baseline in acute SCD (VOC, ACS, and other complications). P-values were calculated with Wilcoxon Rank-Sum tests, adjusted per figure for multiple hypothesis testing using the Holm method (Holm, Scand. J. Statist. 6(1979), no. 2, 65-70).

Example 8: Treatment of Vascular Stasis by Inhibition of G-CSF Signaling

The therapeutic effect of administration of an anti-G-CSFR antibody on vascular stasis in a mouse model of sickle cell disease was assessed.

Townes sickle (SS) mice (n=4/group, 12-20 weeks of age) were treated with VR81 (10 mg/kg) or vehicle only via the tail vein (10 mL/kg).

Figure 8:
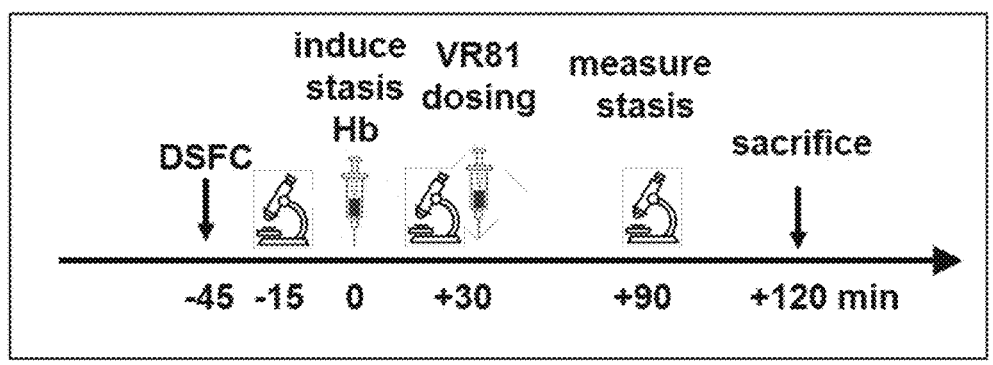
FIG. 8 is a schematic of the therapeutic experimental methodology.
Figure 9:
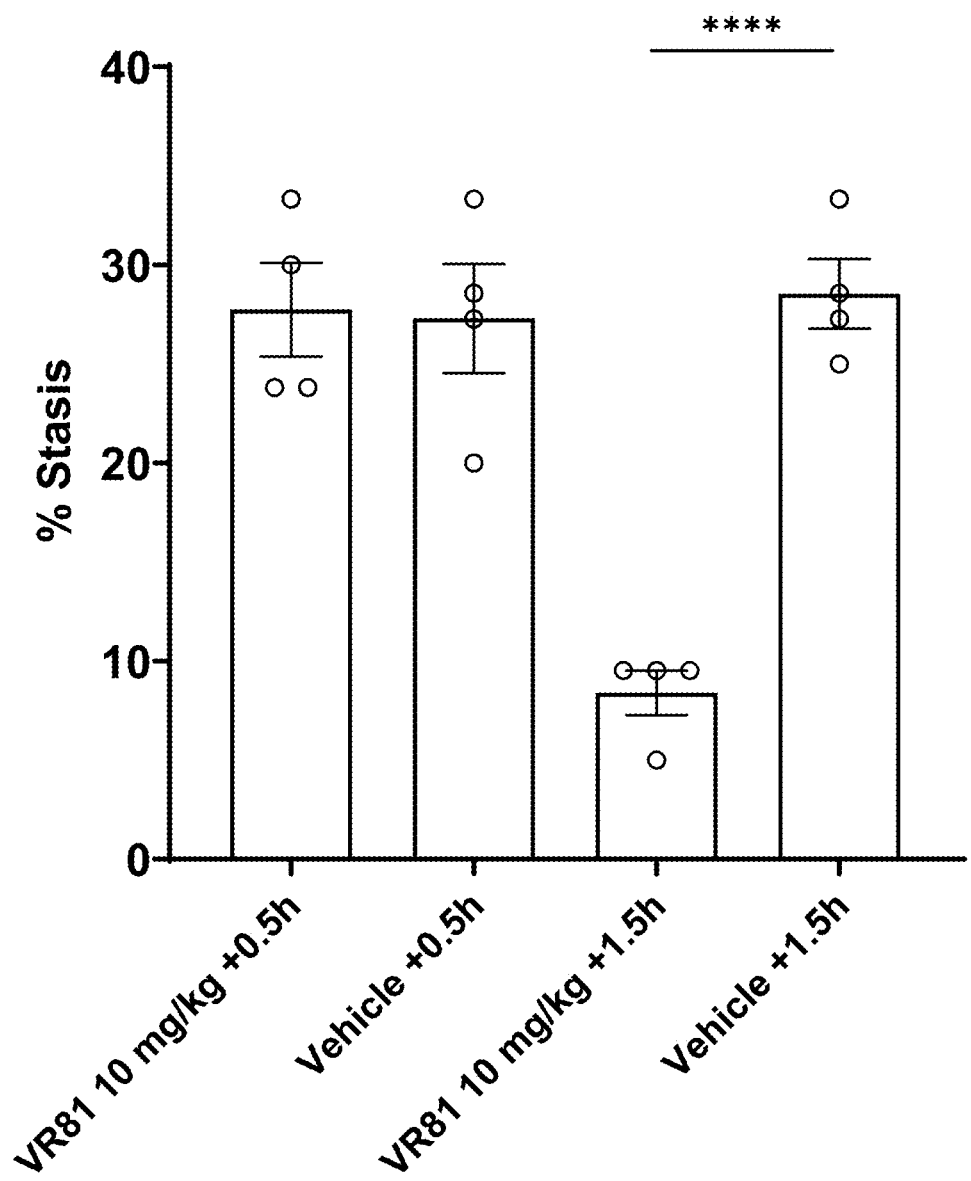
FIG. 9 is a graphical representation showing that administration of VR81 after the induction of stasis reduces stasis compared to treatment with vehicle control.

A summary of the methodology is provided in FIG. 8 and Table 6. Briefly, all SS mice were implanted with a Dorsal Skin Fold Chamber (DSFC) at −45 minutes. Approximately 30 minutes after the start of DSFC implantation at −15 minutes, 20-25 flowing venules in the DSFC window were selected and mapped using intravital microscopy. After baseline selection and mapping of flowing venules, at time 0, all mice were infused via the tail vein with human Hb in sterile saline (1 μmol/kg, 10 ml/kg) to induce microvascular stasis. The test article was administered 30 minutes after inducing microvascular stasis with Hb (i.e., +0.5 h, because the VOC was considered at t=0). Total infusion volume (test article and Hb) was 20 ml/kg. The same vessels that were selected and mapped at baseline were re-examined for stasis (no flow) 1.5 hour after Hb infusion and the percent stasis (% venules with no flow) was calculated. As shown in FIG. 9, administration of VR81 after the induction of stasis significantly reduced percent stasis compared to treatment with vehicle control. At the time of the terminal blood collection (+2 hours), the mice were sacrificed in a $CO_2$ chamber and blood was collected from the heart.

TABLE 6

Methodology

| Group | N | DSFC implantation time (with respect to VOC) | Test Article (TA) | TA dose (mg/kg) | VOC trigger (t = 0) | TA dosing time (with respect to VOC) | Stasis Measurement (with respect to VOC) | Blood sampling time (with respect to VOC) |
|---|---|---|---|---|---|---|---|---|
| 1 | 4 | −45 min | VR81 | 10 | Hb* | +0.5 h | +1.5 h | +2 h |
| 2 | 4 | −45 min | Isotype control | 10 | Hb* | +0.5 h | +1.5 h | +2 h |
| 3 | 4 | −45 min | Vehicle control | — | Hb* | +0.5 h | +1.5 h | +2 h |

\* = 1 µmol/kg;
TA = test article

Terminal blood, liver, lungs, kidneys and spleen were collected and treated as described in Example 2.

Example 9: Dose Response Induction of Microvascular Stasis by mG-CSF In Vivo

The effect of recombinant murine granulocyte colony stimulating factor (mG-CSF) on induction of vascular stasis in a mouse model of sickle cell disease was assessed.

Townes sickle (SS) mice (n=4/group, 2 males and 2 females) were implanted with a Dorsal Skin Fold Chamber (DSFC) approximately 50 minutes before being challenged. After the start of DSFC implantation at −20 minutes (i.e., 20 minutes before challenge), 20-23 flowing venules in the DSFC window were selected and mapped using intravital microscopy. After baseline selection and mapping of flowing venules, at time 0, mice were challenged by infusion with mG-CSF, Hb, mG-CSF+Hb, or vehicle (saline) via the tail as set out in Table 7. Sterile saline was infused at a volume of 5 mL/kg (5 µL/g body weight) via the tail vein and Hb was administered at 1 µmol/kg body weight. Recombinant mG-CSF (R&D Systems™) was prepared at 0.2, 1.0, and 2.0 µg/ml, respectively, and infused at a volume of 5 mL/kg (5 µL/g body weight) via the tail vein to achieve a dose of 1, 5, or 10 µg/kg as indicated.

TABLE 7

Methodology

| Group | Mice | N | DSFC | VOC trigger (t = 0) | mG-CSF dose | Stasis measurement time * | Blood sampling time |
|---|---|---|---|---|---|---|---|
| 1 | SS | 4 | Yes | Vehicle | — | +1 h | +2 h |
| 2 | SS | 4 | yes | mG-CSF | 1 µg/kg | +1 h | +2 h |
| 3 | SS | 4 | yes | mG-CSF | 5 µg/kg | +1 h | +2 h |
| 4 | SS | 4 | yes | mG-CSF | 10 µg/kg | +1 h | +2 h |
| 5 | SS | 4 | yes | Hb ** | — | +1 h | +2 h |
| 6 | SS | 4 | yes | Hb ** + mG-CSF | 10 µg/kg | +1 h | +2 h |

\* = with respect to mG-CSF infusion;
\*\* = 1 µmol/kg

Figure 10:
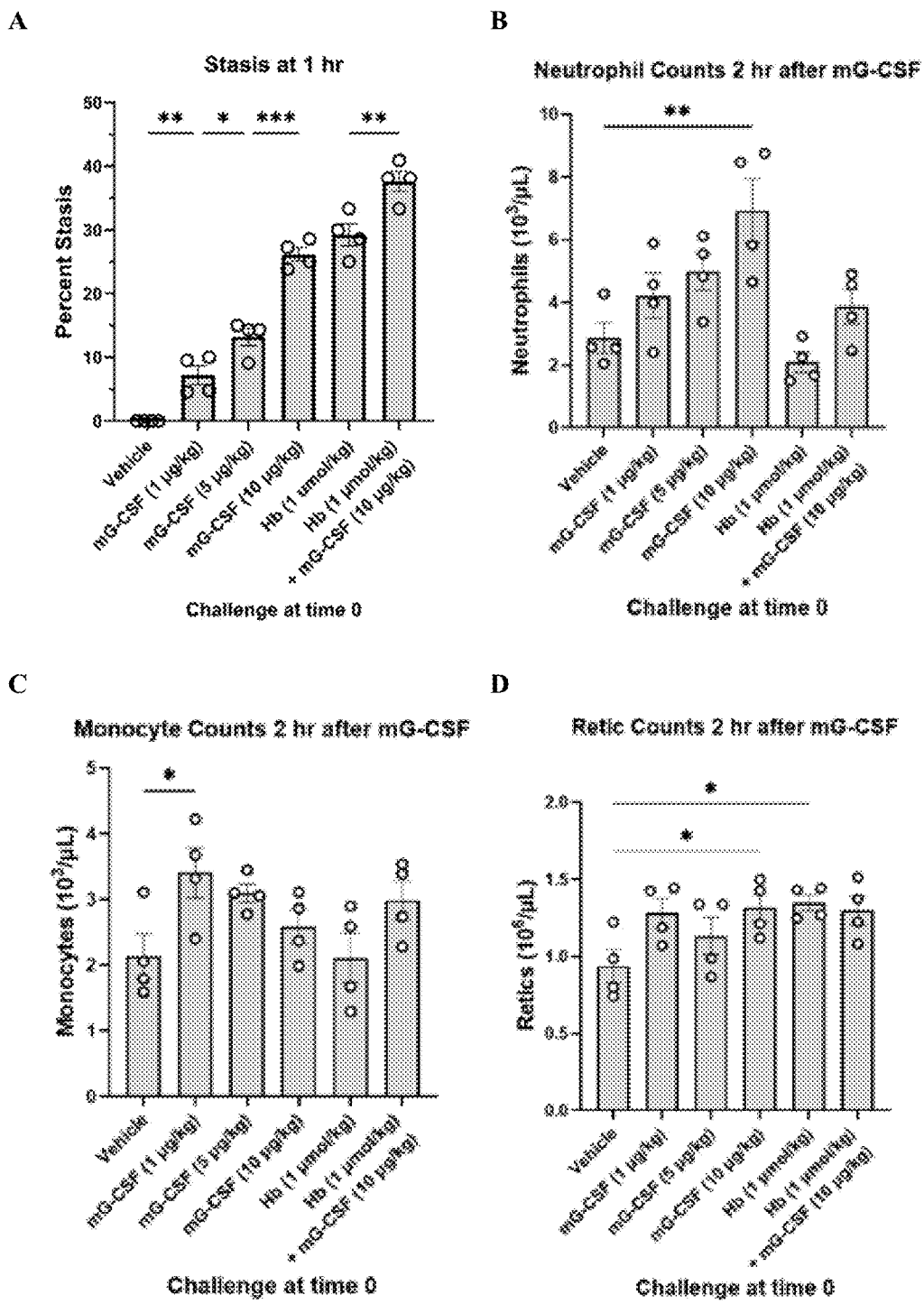
FIG. 10 is a graphical representation showing dose response effect of mG-CSF administration on (A) induction of microvascular stasis 1 hour after mG-CSF administration and (B) neutrophil counts, (C) monocyte counts and (D) reticulocyte counts 2 hours after mG-CSF administration. The number of static venules were expressed as percent stasis (% static venules/total venules). Bars are means±SEM. *$P<0.05$, $p<0.01$, *$p<0.001$, (A) one-way ANOVA with selected pairwise comparisons and Šidák's multiple comparisons test and (B) one-way ANOVA with Dunnett's multiple comparisons test.

Stasis was measured 1 h after challenge. As shown in FIG. 10A, SS mice exhibited a significant dose responsive increase in microvascular stasis at one hour after infusion as the mG-CSF dose was increased from 0 to 10 µg/kg.

Blood was collected 2 hours after the infusion challenge and induction of microvascular stasis. No significant effect on white blood cell count, lymphocyte count, red blood cell count, hemoglobin levels and hematocrit was observed 2 hours after mG-CSF administration (data not shown). Infusion of mG-CSF at select doses increased neutrophils (10 µg/kg), monocytes (1 µg/kg), and reticulocytes (10 µg/kg) in HbSS mice two hours after infusion (FIG. 10B-10D).

Example 10: Prevention and Treatment of mG-CSF Induced Vascular Stasis by Inhibition of G-CSF Signaling The therapeutic effect of administration of an anti-G-CSFR antibody on mG-CSF induced vascular stasis in a mouse model of sickle cell disease was assessed.

Townes SS mice or normal control AA mice (n=4/group, 2 male, 2 female) were infused with VR81, isotype control antibody, or vehicle (saline) via the tail vein prior to measurement of stasis induced by mG-CSF. The normal control AA mice have the normal human adult beta globin replacing the βS globin.

A summary of the methodology is provided in Table 8. Briefly, all mice were implanted with a Dorsal Skin Fold Chamber (DSFC) at −50 minutes. After the start of DSFC implantation at −20 minutes, 20-23 flowing venules in the DSFC window were selected and mapped using intravital microscopy. After baseline selection and mapping of flowing venules, at time 0, mice were challenged by infusion with mG-CSF (10 µg/kg) to induce microvascular stasis, or vehicle (saline) control via the tail.

The test article was administered at either 7 days before or 40 minutes after mG-CSF infusion (Table 8) and induction of microvascular stasis.

TABLE 8

Methodology

| Group | Mice | N | DSFC | Test Article (TA) | TA Dose (mg/kg)* | mG-CSF (t = 0) *** | VR81 dosing time ** | Stasis measurement time ** | Blood sampling time ** |
|---|---|---|---|---|---|---|---|---|---|
| Prophylactic Treatment before Stasis Induction ||||||||||
| 1 | AA | 4 | yes | Vehicle | — | Vehicle | −7 days | +1 h | +2 h |
| 2 | AA | 4 | yes | Vehicle | — | 10 µg/kg | −7 days | +1 h | +2 h |
| 3 | SS | 4 | yes | Vehicle | — | Vehicle | −7 days | +1 h | +2 h |
| 4 | SS | 4 | yes | Vehicle | — | 10 µg/kg | −7 days | +1 h | +2 h |
| 5 | SS | 4 | yes | VR81 | 10 | 10 µg/kg | −7 days | +1 h | +2 h |
| 6 | SS | 4 | yes | isotype control | 10 | 10 µg/kg | −7 days | +1 h | +2 h |
| Acute Treatment after Stasis Induction ||||||||||
| 7 | SS | 4 | yes | Vehicle | — | 10 µg/kg | +0.5 h | 0.5 h + 1.5 h | +2 h |
| 8 | SS | 4 | yes | VR81 | 10 | 10 µg/kg | +0.5 h | 0.5 h + 1.5 h | +2 h |
| 9 | SS | 4 | yes | isotype control | 10 | 10 µg/kg | +0.5 h | 0.5 h + 1.5 h | +2 h |

Figure 11:
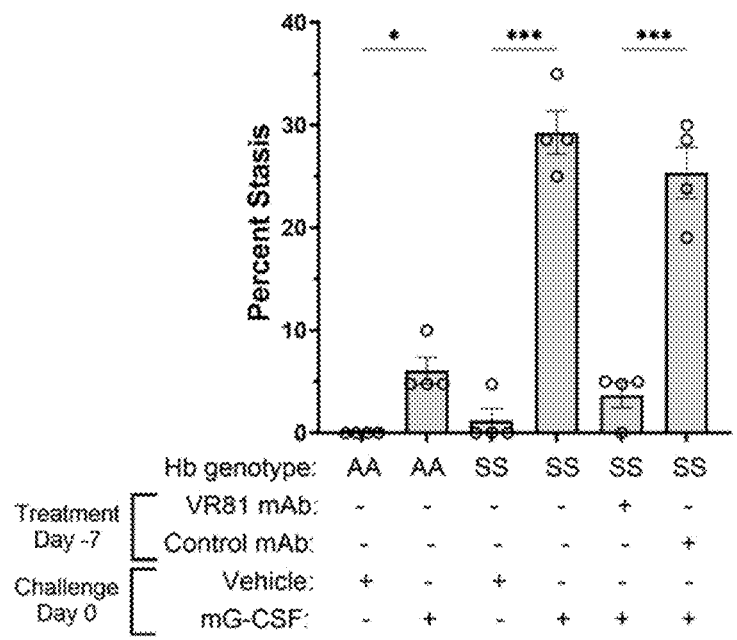
FIG. 11 is a graphical representation showing efficacy of VR81 in (A) preventing and (B) treating mG-CSF induced stasis in Townes sickle mice by reduction in vascular stasis. The number of static venules were expressed as percent stasis (% static venules/total venules). (A) Bars are means±SEM. *$P<0.05$, *$p<0.001$, one-way ANOVA with selected pairwise comparisons and Šidák's multiple comparisons test and (B) Bars are means±SEM. **$P<0.0001$, two-way ANOVA with Tukey's multiple comparisons test.
Figure 11:
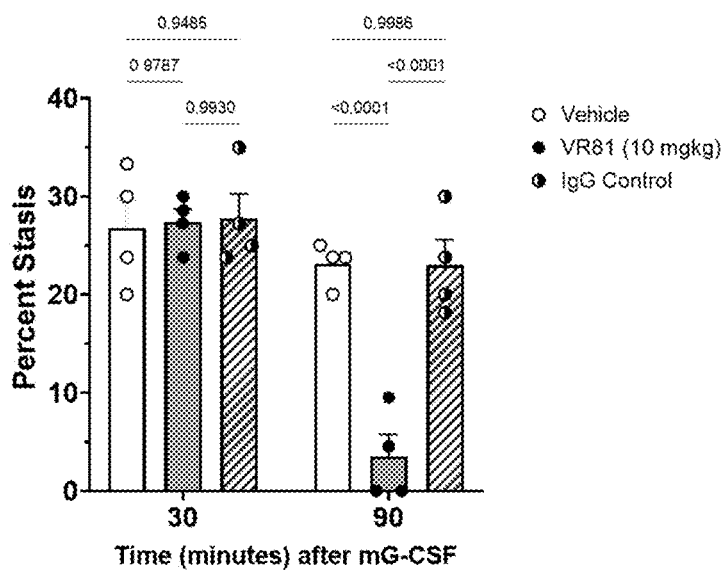

*= Vehicle and TA = 5 µl/g body wt and 10 µg/g body wt; therefore use 10 µg/5 µl = 2 mg/ml TA
** = with respect to mG-CSF injection (t = 0)
*** = mG-CSF: 5 µl/g body wt and 10 ng/g body wt; therefore use 10 ng/5 µl = 2 µg/ml mG-CSF The same vessels that were selected and mapped at baseline were re-examined for stasis (no flow) 1 hour after mG-CSF or vehicle infusion and the percent stasis (% venules with no flow) was calculated. As shown in FIG. 11A, administration of VR81 7 days prior to induction of stasis with mG-CSF significantly reduced percent stasis compared to treatment with vehicle control. Administration of VR81 after induction of stasis with mG-CSF also significantly reduced percent stasis compared to treatment with vehicle control (FIG. 11B).

Blood was collected 2 hours after mG-CSF administration (i.e., +2 h). No significant difference in red blood cell counts, hemoglobin levels, hematocrit, reticulocyte, monocyte, or neutrophil counts was observed in SS mice treated with VR81 7 days prior to induction of vascular stasis with mG-CSF compared to mice treated with isotype control (data not shown). Administration of VR81 7 days prior to induction vascular stasis with mG-CSF significantly reduced (p<0.05) white blood cell and lymphocyte counts compared to mice treated with isotype control (data not shown).

Treatment of mG-CSF induced stasis with VR81 significantly reduced white blood cell counts (p<0.01) and lymphocyte counts (p<0.001) compared to isotype control (data not shown). No significant difference in red blood cell counts, hemoglobin levels, hematocrit, reticulocyte, monocyte, or neutrophil counts was observed in SS mice treated with VR81 following induction of vascular stasis with mG-CSF compared to mice treated with isotype control (data not shown).

Example 11: Long Term Efficacy of Inhibition of G-CSF Signaling in Townes Sickle Cell Mice VR81 was evaluated for long-term efficacy in Townes SS mice. VR81 (1 mg/kg) or saline vehicle was injected weekly for 21 weeks subcutaneously into Townes HbSS and normal control HbAA mice (n=6/group; 3 males and 3 females) to examine its long-term efficacy.

A summary of the methodology is provided in Table 9. Briefly, treatment was administered from 5 weeks of age until the mice were sacrificed at 26 weeks of age. To enhance sickle cell disease pathophysiology, half of the Townes HbSS and the HbAA mice were exposed to hypoxia/reoxygenation (H/R; 10% $O_2$ for 6 hours) every five weeks beginning at 10 weeks of age. The 4th and last H/R was given at 25 weeks of age, 7 days prior to sacrifice. The last test article injection was given immediately prior to collection of a 24-hour urine sample and 48 hours prior to sacrifice.

TABLE 9

Methodology

| | Mouse strain | Test article | SC dose (mg/kg) | SC dosing regimen | Hypoxia/Re-oxygenation | Mouse number group |
|---|---|---|---|---|---|---|
| 1 | SS | VR81 | 1 | once per wk starting at 5 wks | — | 6 |
| 2 | SS | vehicle | — | once per wk starting at 5 wks | — | 6 |
| 3 | SS | VR81 | 1 | once per wk starting at 5 wks | every 5 wks beginning at 10 wks | 6 |

TABLE 9-continued

Methodology

| Mouse strain | Test article | SC dose (mg/kg) | SC dosing regimen | Hypoxia/Re-oxygenation | Mouse number group |
|---|---|---|---|---|---|
| 4 SS | vehicle | — | once per wk starting at 5 wks | every 5 wks beginning at 10 wks | 6 |
| 5 AA | VR81 | 1 | once per wk starting at 5 wks | every 5 wks beginning at 10 wks | 6 |
| 6 AA | vehicle | — | once per wk starting at 5 wks | every 5 wks beginning at 10 wks | 6 |

There was a trend towards an improvement (higher) in urine osmolality in HbSS mice, but the increase did not reach statistical significance (data not shown).

Figure 12:
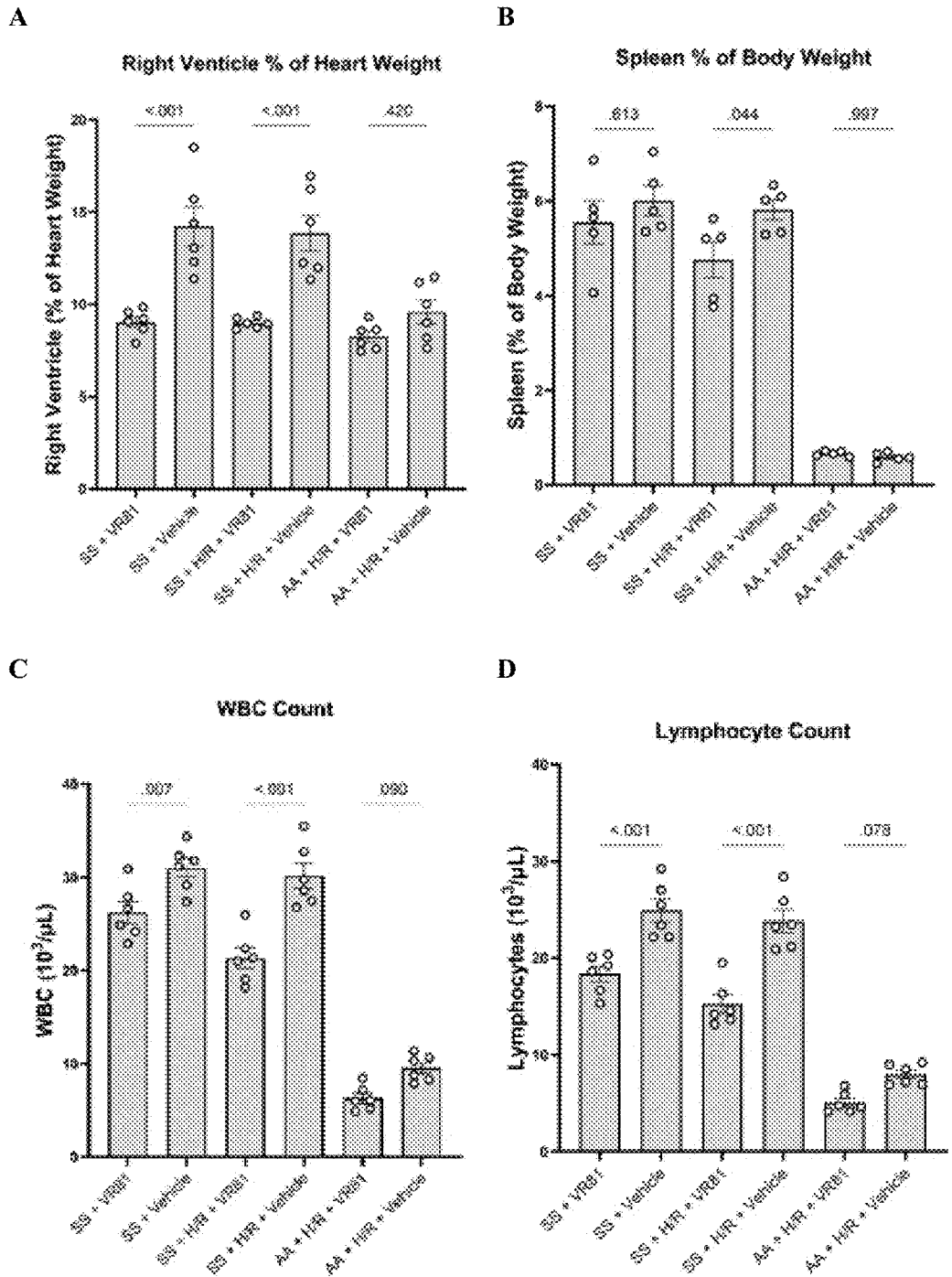
FIG. 12 is a series of graphical representations showing the effect of long term VR81 treatment in Townes SS or control AA mice with or without H/R treatment. Significant effects of long term VR81 treatment were observed on (A) right ventricle and (B) spleen weight as % of body weight, (C) white blood cell (D) lymphocyte, (E) neutrophil and (F) monocyte count; and expression of hepatic (G) CSF3R mRNA, (H) VCAM-1 mRNA and (I) NRF2L2 mRNA levels. Bars are means±SEM. One-way ANOVA with selected pairwise comparisons and Šidák's multiple comparisons test.
Figure 12:
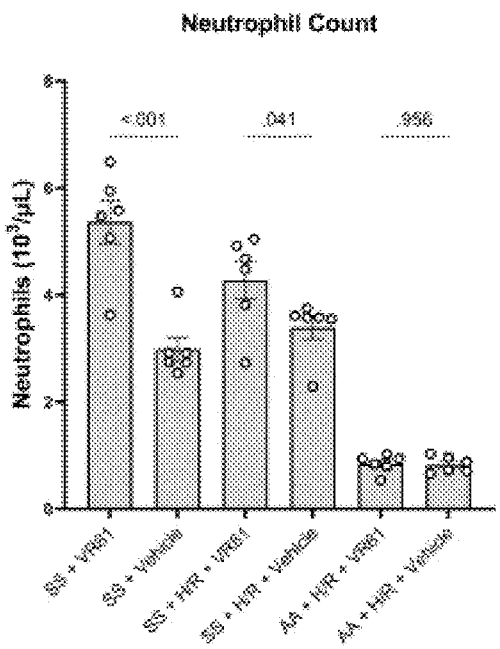
Figure 12:
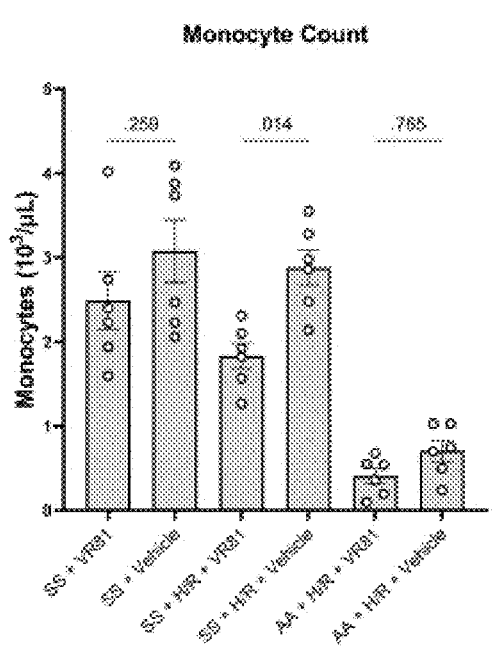
Figure 12:
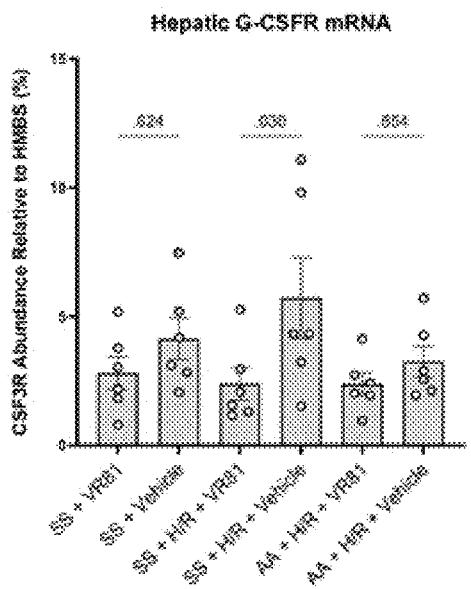
Figure 12:
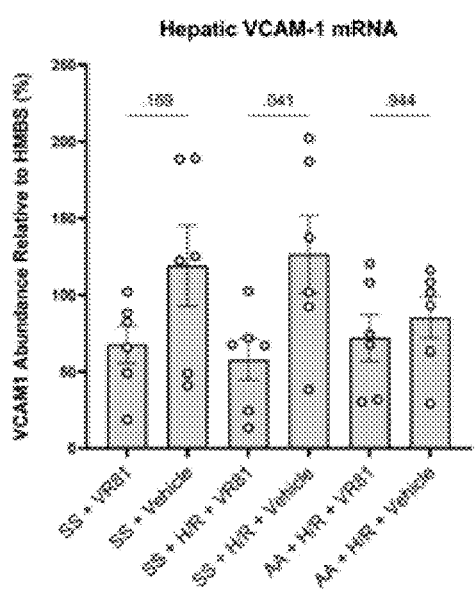
Figure 12:
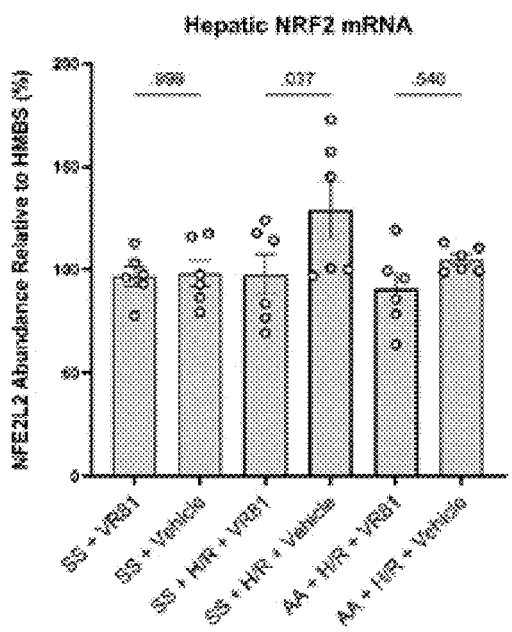

As shown in FIG. 12A, long term VR81 treatment of SS mice with or without H/R significantly reduced right ventricle weight (as % of body weight) compared to treatment with vehicle alone. Right ventricle weights decreased to the same level as HbAA mice. No effect on ventricle weight was observed in control AA mice. VR81 treatment also significantly reduced spleen weight (as % of body weight) in SS mice subjected to H/R compared to treatment with vehicle alone (FIG. 12B). No significant effect on spleen weight was observed in AA control mice or SS mice not subjected to H/R. Long term VR81 treatment had no significant effect on urine osmolality, or heart, lung, or kidney weights (as % of body weight) compared to mice treated with vehicle control (data not shown).

Long term VR81 treatment significantly reduced white blood cell and lymphocyte counts in SS mice in the presence and absence of H/R treatment compared to mice treated with vehicle control (FIG. 12C and FIG. 12D). No significant effect was observed in AA control mice. Neutrophil counts were significantly elevated in SS mice treated with long term VR81 with and without H/R treatment compared to vehicle treated mice (FIG. 12E), however no effect was observed in AA control mice. Long term VR81 treatment significantly reduced monocyte counts in SS mice with H/R treatment compared to vehicle treated mice (FIG. 12F). No significant effect was observed in other treatment groups. Long term VR81 treatment had no significant effect on red blood cell counts, hemoglobin levels, hematocrit or reticulocyte counts compared to vehicle treated mice (data not shown).

Hepatic mRNA for proteins of interest were measured by droplet digital PCR (ddPCR) and expressed relative to control HMBS mRNA. As shown in FIG. 12G, long term VR81 treatment significantly reduced Csf3r (G-CSFR) abundance in SS mice with H/R compared to vehicle control treated mice. No significant effect was observed in other treatment groups. A significant decrease in VCAM-1 and NRF2L2 mRNA abundance was observed in SS mice with H/R treatment following long term VR81 treatment compared to mice treated with vehicle control (FIG. 12H and FIG. 12I). No significant effect was observed in other treatment groups. No significant effect in ICAM-1, E-Selectin, Tissue Factor F3, or HMOX1 mRNA abundance was observed following long term VR81 treatment in SS or AA mice with or without H/R treatment.

The invention claimed is:

1. A method for treating or preventing or delaying progression or reducing or inhibiting or hindering development of a complication associated with sickle cell disease in a subject suffering from sickle cell disease, wherein the complication associated with sickle cell disease affects the cardiovascular system, the method comprising administering to the subject a protein comprising an antigen binding domain of an antibody that specifically binds to granulocyte colony stimulating factor (G-CSF) receptor (G-CSFR) and inhibits G-CSF signaling, wherein the antigen binding domain comprises:
  (i) a heavy chain variable region ($V_H$) comprising the amino acid sequence set forth in SEQ ID NO: 4 and a light chain variable region ($V_L$) comprising the amino acid sequence set forth in SEQ ID NO: 5; and/or
  (ii) a $V_H$ comprising a complementarity determining region (CDR) 1 comprising the sequence set forth in SEQ ID NO: 6; a CDR2 comprising the sequence set forth in SEQ ID NO: 7; and a CDR3 comprising the sequence set forth in SEQ ID NO: 8; and a $V_L$ comprising a CDR1 comprising the sequence set forth in SEQ ID NO: 9; a CDR2 comprising the sequence set forth in SEQ ID NO: 10; and a CDR3 comprising the sequence set forth in SEQ ID NO: 11.

2. The method of claim 1, wherein the complication associated with sickle cell disease is a vasculopathy.

3. The method of claim 2, wherein the vasculopathy is associated with vaso-occlusion or hemolysis-endothelial dysfunction.

4. The method of claim 3, wherein the subject has or is suffering from a complication of the vaso-occlusion.

5. The method of claim 4, wherein the complication of the vaso-occlusion is a vaso-occlusive crisis, acute chest syndrome, osteonecrosis, progressive retinopathy, chronic renal failure, pulmonary hypertension, priapism, splenic sequestration and/or stroke.

6. The method of claim 1, wherein the complication associated with sickle cell disease is a vaso-occlusive crisis and/or acute chest syndrome.

7. The method of claim 6, wherein the subject has or is suffering from pain associated with vaso-occlusive crisis and/or pain associated with acute chest syndrome.

8. The method of claim 1, wherein the sickle cell disease is selected from the group consisting of sickle cell anemia (HbSS), hemoglobin sickle cell disease (HbSC), hemoglobin sickle-beta-thalassemia (HbS beta-thalassemia), sickle cell-hemoglobin D disease (HbSD), sickle cell-hemoglobin E disease (HbSE) and sickle cell-hemoglobin O disease (HbSO).

9. The method of claim 1, wherein the method reduces and/or prevents and/or inhibits:
   (i) neutrophil adhesion to endothelial cells and transmigration;
   (ii) neutrophil-platelet aggregate formation;
   (iii) neutrophil extracellular trap (NET) formation;
   (iv) reactive oxygen species formation;
   (v) von Willebrand factor secretion from endothelial cells;
   (vi) neutrophil activation;
   (vii) neutrophil extracellular trap (NET) activation; and/or
   (viii) endothelial cell activation.

10. The method of claim 1, wherein the protein is administered in an amount sufficient to have one or more of the following effects:
   (i) reduce or prevent an increase in percent vascular stasis;
   (ii) reduce or prevent an increase in blood flow;
   (iii) reduce or inhibit expression of E-selectin on endothelial cells;
   (iv) reduce or inhibit expression of vascular cell adhesion molecule 1 (VCAM-1) on endothelial cells;
   (v) reduce or inhibit expression of intercellular adhesion molecule 1 (ICAM-1) on endothelial cells;
   (vi) reduce or inhibit expression of P-selectin on endothelial cells;
   (vii) increase or upregulate expression of heme-oxygenase-1 (HO-1) on endothelial cells;
   (viii) increase or upregulate expression of NF-E2-related factor 2 (NRF2) on endothelial cells; and
   (ix) reduce or prevent an increase in neutrophil infiltration and/or accumulation in the subject's liver.

11. The method of claim 1, wherein the protein is selected from the group consisting of:
   (i) a single chain Fv fragment (scFv);
   (ii) a dimeric scFv (di-scFv);
   (iii) a diabody;
   (iv) a triabody;
   (v) a tetrabody;
   (vi) a Fab;
   (vii) a F (ab')$_2$;
   (viii) a Fv;
   (ix) one of (i) to (viii) linked to a constant region of an antibody, Fc or a heavy chain constant domain ($C_H$) 2 and/or $C_H$3;
   (x) one of (i) to (ix) linked to albumin or a functional fragment or variants thereof or a protein that binds to albumin; and
   (xi) an antibody.

12. The method of claim 1, wherein the protein comprising an antigen binding domain of an antibody that specifically binds to G-CSFR and comprises:
   (i) a $V_H$ comprising the sequence encoded by the nucleic acid comprising SEQ ID NO: 21 and a $V_L$ comprising the sequence encoded by the nucleic acid comprising SEQ ID NO: 22;
   (ii) a $V_H$ comprising three CDRs of a $V_H$ comprising the sequence encoded by the nucleic acid comprising SEQ ID NO: 21 and a $V_L$ comprising three CDRs of a $V_L$ comprising the sequence encoded by the nucleic acid comprising SEQ ID NO: 22; or
   (iii) a $V_H$ comprising:
      (a) a CDR1 comprising the sequence encoded by the nucleic acid comprising SEQ ID NO: 23;
      (b) a CDR2 comprising the sequence encoded by the nucleic acid comprising SEQ ID NO: 24; and
      (c) a CDR3 comprising the sequence encoded by the nucleic acid comprising SEQ ID NO: 25; and
   a $V_L$ comprising:
      (a) a CDR1 comprising the sequence encoded by the nucleic acid comprising SEQ ID NO: 26;
      (b) a CDR2 comprising the sequence encoded by the nucleic acid comprising SEQ ID NO: 27; and
      (c) a CDR3 comprising the sequence encoded by the nucleic acid comprising SEQ ID NO: 28.

13. The method of claim 1, wherein the protein comprising an antigen binding domain of an antibody that specifically binds to G-CSFR and inhibits G-CSF signaling is administered in combination with a standard of care therapy, wherein the standard of care therapy comprises one or more or all of the following:
   (a) blood transfusion;
   (b) stem cell or bone marrow transplantation;
   (c) hemoglobin S (HbS) polymerization inhibitor;
   (d) crizanlizumab;
   (e) antimetabolite;
   (f) L-glutamine;
   (g) analgesic; and
   (h) antibiotics,
   wherein:
   (i) the blood transfusion is a red blood cell transfusion; and/or
   (ii) the antimetabolite is hydroxyurea.

* * * * *